(12) United States Patent
Kyle et al.

(10) Patent No.: US 7,767,699 B2
(45) Date of Patent: Aug. 3, 2010

(54) THERAPEUTIC AGENTS USEFUL FOR TREATING PAIN

(75) Inventors: Donald J. Kyle, Newtown, PA (US); Qun Sun, Princeton, NJ (US); Xiaoming Zhou, Plainsboro, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 1171 days.

(21) Appl. No.: 11/317,832

(22) Filed: Dec. 22, 2005

(65) Prior Publication Data

US 2006/0235055 A1    Oct. 19, 2006

Related U.S. Application Data

(63) Continuation of application No. PCT/US2004/021246, filed on Jul. 1, 2004.

(60) Provisional application No. 60/484,881, filed on Jul. 3, 2003.

(51) Int. Cl.
A61K 31/4439 (2006.01)
C07D 401/04 (2006.01)
C07D 401/12 (2006.01)

(52) U.S. Cl. .................. 514/343; 546/278.4; 546/279.1

(58) Field of Classification Search ............. 546/278.4, 546/279.1; 514/343
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,039,680 A | 8/1991 | Imperato et al. |
| 5,059,595 A | 10/1991 | Le Grazie |
| 5,073,543 A | 12/1991 | Marshall et al. |
| 5,075,341 A | 12/1991 | Mendelson et al. |
| 5,120,548 A | 6/1992 | McClelland et al. |
| 5,198,459 A | 3/1993 | Imperato et al. |
| 5,232,934 A | 8/1993 | Downs |
| 5,294,624 A | 3/1994 | Fuse et al. |
| 5,354,556 A | 10/1994 | Sparks et al. |
| 5,556,837 A | 9/1996 | Nestler et al. |
| 5,556,838 A | 9/1996 | Mayer et al. |
| 5,574,052 A | 11/1996 | Rose et al. |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 5,762,925 A | 6/1998 | Sagen |
| 6,109,269 A | 8/2000 | Rise et al. |
| 6,136,839 A | 10/2000 | Isakson et al. |
| 6,156,908 A | 12/2000 | Drauz et al. |
| 6,204,284 B1 | 3/2001 | Beer et al. |
| 6,248,756 B1 | 6/2001 | Anthony et al. |
| 6,492,541 B2 | 12/2002 | Drauz et al. |
| 6,656,957 B1 | 12/2003 | Allgeier et al. |
| 2004/0044003 A1 | 3/2004 | Kyle et al. |
| 2004/0053914 A1 | 3/2004 | Gharagozloo et al. |
| 2004/0102450 A1 | 5/2004 | Ewing et al. |
| 2004/0106625 A1 | 6/2004 | Kyle et al. |
| 2004/0127501 A1 | 7/2004 | Chen et al. |
| 2004/0259931 A1 | 12/2004 | Goodfellow et al. |

FOREIGN PATENT DOCUMENTS

| | | |
|---|---|---|
| EP | 0477409.6-2101 | 4/2007 |
| WO | WO 92-02502 | 2/1992 |
| WO | WO 98-20867 | 5/1998 |
| WO | WO 99-37304 | 7/1999 |
| WO | WO 00-47553 | 8/2000 |
| WO | WO 01-17992 | 3/2001 |
| WO | WO 01-96331 | 12/2001 |

OTHER PUBLICATIONS

*Controlled Drug Bioavailability*, vol. 1, Drug Product Design and Performance (Smolen and Ball, eds., 1984).
Berkow et al., "Seizure Disorders," *The Merck Manual of Medical Information*, pp. 345-350 (1997).
Berkow et al., "Stroke," *The Merck Manual of Medical Information*, pp. 352-355 (1997).
Buchwald et al., "Long-term, continuous intravenous heparin administration by an implantable infusion pump in ambulatory patients with recurrent venous thrombosis," *Surgery* 88:507 (1980).

(Continued)

*Primary Examiner*—Patricia L Morris
(74) *Attorney, Agent, or Firm*—Dechert LLP

(57) ABSTRACT

The invention provides a compound of formula (I):

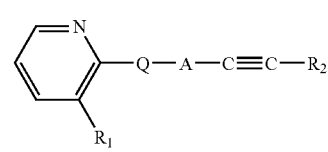

(I)

(where $R_1$, Q, A and $R_2$ are disclosed herein) or a pharmaceutically acceptable salt thereof (a "Pyridine-alkynyl Compound"); pharmaceutical compositions comprising an effective amount of a Pyridine-alkynyl Compound; and methods for treating or preventing a condition such as pain, urinary incontinence, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, amyotrophic lateral sclerosis, dementia, retinopathy, a muscle spasm, a migraine, vomiting, dyskinesia or depression in an animal comprising administering to an animal in need thereof an effective amount of a Pyridine-alkynyl Compound.

27 Claims, No Drawings

OTHER PUBLICATIONS

Chiamulera et al., "Reinforcing and Locomotor Stimulant Effects of Cocaine are Absent in mGluR5 Null Mutant Rice," *Nature Neurosci.* 4(9):873-874 (2001).

Wong et al., "Metabotropic Glutamate Receptors and Epileptogenesis," *Epilepsy Currents* 2(3):81-85 (2002).

Cooke, "Glycopyrrolate in Bladder Dysfunction," *SA Medical J.* 63:3 (1983).

D'Amour et al., "A Method for Determining Loss of Pain Sensation," *J. Pharmacol. Exp. Ther.* 72:74-79 (1941).

Di Marzo et al., "Endovanilloid Signaling in Pain," *Current Opinion in Neurobiology* 12:372-379 (2002).

Dogrul et al., "Peripheral and Spinal Antihyperalgesic Activity of SIB-1757, A Metabotropic Glutamate Receptor (mGluR$_5$) Antagonist, in Experimental Neuropathic Pain in Rats," *Neurosci. Lett.* 292(2):115-118 (2000).

During et al., "Controlled Release of Dopamine from a Polymeric Brain Implant: In Vivo Characterization," *Ann. Neurol.* 25:351 (1989).

Foley, "Pain" *Cecil Textbook of Medicine*, pp. 100-107 (1996).

Fundytus et al, "Antisense Oligonucleotide Knockdown of mGluR$_1$ Alleviates Hyperalgesia and Allodynia Associated with Chronic Inflammation," *Pharmacol., Biochem. & Behavior* 73:401-410 (2002).

Fundytus et al., "In vivo Antinociceptive Activity of Anti-Rat mGluR$_1$ and mGluR$_5$ Antibodies in Rats," *NeuroReport* 9:731-735 (1998).

Fundytus et al., "Knockdown of Spinal Metabotropic Glutamate Receptor I (mGluR$_1$) Alleviates Pain and Restores Opioid Efficacy after Nerve Injury in Rats," *Brit. J. Pharmacol.* 132:354-367 (2001).

Fundytus et al., "Effect of activity at metabotropic, as well as ionotropic (NMDA), glutamae receptors on morphine dependence," *Brit. J. Pharmacol.* 113:1215-1220 (1994).

Fundytus, "Glutamate Receptors and Nociception Implications for the Drug-Treatment of Pain," *CNS Drugs* 15:29-58 (2001).

Genin et al. "Synthesis and Structure—Activity Relationship of the (Alkylamino)piperidine-Containing BHAP Class of Non-Nucleoside Reverse Transcriptase Inhibitors: Effect of 3-Alkylpyridine Ring Substitution," *J Med Chem* 42:4140-4149 (1999).

Geri et al. "Reactions of Nitrogen Nucleohiles with 1-Bromoallenes: Regioselective Synthesis of Propargylamines," *Gazz. Chim. Ital.* 124:241-248 (1994).

Brunton, "Agents for Control of Gastric Acidity and Treatment of Peptic Ulcers," *Goodman and Gillman's the Pharmaceutical Basis of Therapeutics*, pp. 506, 901-915 (J. Hardman and L. Limbird Eds., 9$^{th}$ ed. (1996).

Goodson, in *Medical Applications of Controlled Release*, vol. 2, pp. 115-138 (1984).

Grupp et al., "Protection against Hypoxia-reoxygenation in the Absence of Poly (ADP-ribose) Synthetase in Isolated Working Hearts," *J. Mol. Cell Cardiol.* 31:297-303 (1999).

Hanson, *Analgesic, Antipyretic and Anti-Inflammatory Drugs in Remington: The Science and Practice of Pharmacy* vol. II 1196-1221 (A.R. Gennaro ed. 19th ed. 1995).

Hargreaves et al., "A New and Sensitive Method for Measuring Thermal Nociception in Cutaneous Hyperalgesia," *Pain* 32(1):77-88 (1988).

Hay et al. "Palladium-Catalyzed Hydroarylation of Propiolamides. A Regio-and Stereocontrolled Method for Preparing 3,3-Diarylacrylamides," *J. Org. Chem.* 63:5050-5058 (1998).

Herzog et al., "Urinary Incontinence: Medical and Psychosocial Aspects," *Annu. Rev. Gerontol. Geriatr.* 9:74-119 (1989).

Howard et al. "Intracerebral drug delivery in rats with lesion-induced memory deficits," *J. Neurosurg.* 71:105 (1989).

Insel, "Analgesic-Antipyretic and Anti-inflammatory Agents and Drugs Employed in the Treatment of Gout," in *Goodman & Gilman's The Pharmacological Basis of Therapeutics* 617-57 (Perry B. Molinhoff and Raymond W. Ruddon eds., 9$^{th}$ ed 1996).

Jhamandas et al. "Spinal Amino Acid Release and Precipitated Withdrawal in Rats Chronically Infused with Spinal Morphine," *J. Neurosci.* 16:2758-2766 (1996).

Kim, "An Experimental Model for Peripheral Neuropathy Produced by Segmental Spinal Nerve Ligation in the Rat," *Pain* 50(3):355-363 (1992).

Weber et al. "Enantiopure 4- and 5-Aminopiperidin-2-ones: Regiocontrolled Synthesis and Conformational Characterization as Bioactive B-Turn Mimetics," *J. Org. Chem.* 65:7406-7416 (2000).

Langer, "New Methods of Drug Delivery," *Science* 249:1527-1533 (1990).

Levin et al., "Direct Measurement of the Anticholinergic Activity of a Series of Pharmacological Compounds on the Canine and Rabbit Urinary Bladder," *J. Urology* 128:396-398 (1982).

Levy et al. "Inhibition of Calcification of Bioprosthetic Heart Valvews by Local Controlled-Release Diphosphonate," *Science* 228:190 (1985).

Liu et al. "Synthesis of chiral oxacyclic dienes via ruthenium-catalyzed enyne metathesis: useful building blocks for chiral tricyclic oxygen derivatives," *Tetrahedron* 58:5627-5637 (2002).

Martin et al. "The Synthesis and Biological Evaluation of Non-Peptidic Matrix Metalloproteinase Inhibitors," *Bioorg. Med. Chem. Lett.* 9:2887-2892 (1999).

*Medical Applications of Controlled Release* (Langer and Wise eds., 1974).

Mirakhur et al., "Glycopyrrolate: Pharmacology and Clinical Use," *Anaesthesia* 38:1195-1204 (1983).

Bartho et al., "Involvement of capsaicin-sensitive neurones in hyperalgesia and enhanced opioid antinociception in inflammation," *Naunyn-Schmiedeberg's Archives Pharmacol.* 342:666-670 (1990).

Nicolaou et al. "An Intramolecular Diels—Alder Strategy to Forskolin,", *J. Chem. Soc., Chem. Comm.* 7:421 (1985).

Ossowska et al., "Blockade of the Metabotropic Glutamate Receptor Subtype 5 (mGluR5) Produces Antiparkinsonian-Like Effects in Rats," *Neuropharmacol.* 41:413-420 (2001).

Langer and Peppas, "Chemical and Physical Structure of Polymers as Carriers for Controlled Release of Bioactive Agents: A Review," *J. Macromol. Sci. Rev. Macromol. Chem.* 23:61 (1983).

Radebough et al., "Preformulation," *Remington's Pharmaceutical Sciences* 1447-1676 (Alfonso R. Gennaro ed., 19th ed. 1995).

Resnick, "Urinary Incontinence," *Lancet* 346:94-99 (1995).

Rutjes et al, "A Stereodivergent Approach to Substituted 4-Hydroxypiperidines," *J. Org. Chem.* 67:7869-7871 (2002).

Sabatini et al. "8-Methyl-7-substituted-1,6-naphthyridine-3-carboxylic Acids as New 6-Desfluoroquinolone Antibacterials [1]"., *J. Heterocyclic Chem.* 36:953-957 (1999).

Sanchez et al. "Quinolone Antibacterial Agenets. Synthesis and Structure-Activity Relationships of 8-Substituted Quinoline-3-carboxylic Acids and 1,8-Naphthyridine-3-carboxylic Acids," *J. Med. Chem.* 31:983-991 (1988).

Saudek et al. "A Preliminary Trial of the Programable Implantable Medication System for Insulin Delivery," *New Engl. J. Med.* 321:574 (1989).

Schlaeger et al, "Transient Transfection in Mammalian Cells," *New Dev. New Appl. Anim. Cell Techn.*, Proc. ESACT Meet., 15$^{th}$a (1998), 105-112 and 117-120.

Sefton, "Implantable Pumps," *CRC Crit. Ref. Biomed. Eng.* 14:201 (1987).

Seltzer et al., "A Novel Behavioral Model of Neuropathic Pain Disorders Produced in Rats by Partial Sciatic Nerve Injury," *Pain* 43:205-218 (1990).

Sharif et al. "Attenuation of mophine tolerance after antisense oligonucleotide knock-down of spinal mGluR1," *Brit. J. Pharmacol.* 136:865-872 (2002).

Spooren et al., "Novel Allosteric Antagonists Shed Light on mGlu$_5$ Receptors and CNS Disorders," *Trends Pharmacol. Sci.* 22(7):331-337 (2001).

Stein, "Unilateral Inflammation of the Hindpaw in Rats as a Model of Prolonged Noxious Stimulation: Alterations in Behavior and Nociceptive Thresholds," *Pharmacol. Biochem. Behavior* 31:451-455 (1988).

Tatarczynska et al., "Potential Anxiolytic- and Antidepressant-Like Effects of MPEP, A Potent, Selective and Systemically Active mGlu5 Receptor Antagonist," *Brit. J. Pharmacol.* 132(7):1423-1430 (2001).

Treat et al., *Liposomes in the Therapy of Infectious Disease and Cancer*, pp. 317-327 and 353-365 (1989).

Treit, "Animal Models for the Study of Anti-anxiety Agents: A Review," *Neurosci. Biobehavioral Revs.* 9(2):203-222 (1985).

Tsou et al.., "6-Substituted-4-(3-bromophenylamino)quinazolines as Putative Irreversible Inhibitors of the Epidermal Growth Factor Receptor and Human Epidermal Growth Factor Receptor Tyrosine Kinases with Enhanced Antitumor Activity," *J. Med. Chem.* 44:2719-2734 (2001).

Walker et al., "Metabotropic Glutamate Receptor Subtype 5 (mGlu5) and Nociceptive Function. I. Selective Blockade of mGlu5 Receptors in Models of Acute, Persistent and Chronic Pain," *Neuropharmacol.* 40:1-9 (2000).

Wein, "Pharmacology of Incontinence," *Urologic Clinics of North America* 22(3):557-577 (1995).

THERAPEUTIC AGENTS USEFUL FOR TREATING PAIN

This application is a continuation of and claims the benefit of International patent application no. PCT/US2004/021246, filed Jul. 1, 2004, which claims the benefit of U.S. provisional application No. 60/484,881, filed Jul. 3, 2003, the disclosure of each application being incorporated by reference herein in its entirety.

1. FIELD OF THE INVENTION

The present invention relates to Pyridine-alkynyl Compounds, compositions comprising an effective amount of a Pyridine-alkynyl Compound and methods for treating or preventing a condition such as pain, urinary incontinence (UI), an addictive disorder, Parkinson's disease, parkinsonism, anxiety, epilepsy, a seizure, stroke, a pruritic condition, psychosis, a cognitive disorder, a memory deficit, restricted brain function, Huntington's chorea, amyotrophic lateral sclerosis (ALS), dementia, retinopathy, a muscle spasm, a migraine, vomiting, dyskinesia, or depression comprising administering to an animal in need thereof an effective amount of a Pyridine-alkynyl Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or cental nervous system and is maintained by aberrant somatosensory processing. There is a large body of evidence relating activity at both Group I metabotropic glutamate receptors, i.e., metabotropic glutamate receptor 1 ("mGluR1") and metabotropic glutamate receptor 5 ("mGluR5") (M. E. Fundytus, *CNS Drugs* 15:29-58 (2001)), and vanilloid receptors ("VR1") (V. Di Marzo et al., *Current Opinion in Neurobiology* 12:372-379 (2002)) to pain processing. Inhibiting mGluR1 or mGluR5 reduces pain, as shown by in vivo treatment with antibodies selective for either mGluR1 or mGluR5, where neuropathic pain in rats was attenuated (M. E. Fundytus et al., *NeuroReport* 9:731-735 (1998)). It has also been shown that antisense oligonucleotide knockdown of mGluR1 alleviates both neuropathic and inflammatory pain (M. E. Fundytus et al., *Brit. J. Pharmacol.* 132:354-367 (2001); M. E. Fundytus et al., *Pharmacol., Biochem. & Behavior* 73:401-410 (2002)). Small molecule antagonists for mGluR5-attenuated pain in in vivo animal models are disclosed in, e.g., K. Walker et al., *Neuropharmacol.* 40:1-9 (2000) and A. Dogrul et al., *Neurosci. Let.* 292:115-118 (2000)).

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g. gabapentin, carbamazepine, valproic acid, topiramate, phenyloin), NMDA antagonists (e.g. ketamine, dextromethorphan), topical lidocaine (for post-herpetic neuralgia), and tricyclic antidepressants (e.g. fluoxetine, sertraline and amitriptyline).

UI is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, *Urol. Clin. N. Am.* 22:557-577 (1995); Levin et al., *J. Urol.* 128:396-398 (1982); Cooke et al., *S. Afr. Med. J.* 63:3 (1983); R. K. Mirakhur et al., *Anaesthesia* 38:1195-1204 (1983)). These drugs are not effective, however, in all patients having uninhibited bladder contractions.

None of the existing commercial drug treatments for UI has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. *The Merck Manual of Medical Information* 631-634 (R. Berkow ed., 1997).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the addictive substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid tolerance. U.S. Pat. No. 6,204,284 to Beer et al. discloses racemic (±)-1-(3,4-dichlorophenyl)-3-azabicyclo [3.1.0]hexane for use in the prevention or relief of a withdrawal syndrome resulting from addiction to drugs and for the treatment of chemical dependencies. Glutamate release is enhanced during opioid withdrawal (K. Jhamandas et al., *J. Neurosience* 16:2758-2766 (1996)). Recent evidence suggests a role for Group I mGluRs in opioid tolerance and dependence. An interaction between opioids and mGluRs was demonstrated when it was shown that an antagonist at Group I mGluRs significantly attenuated withdrawal symptoms in opioid-dependent rats (M. E. Fundytus et al., *Brit. J.*

Pharmacol. 113:1215-1220 (1994)). More recent results show that antisense oligonucleotide knockdown of mGluR1 reduces protein kinase C activity (M. E. Fundytus et al., Brit. J. Pharmacol. 132:354-367 (2001)), which may be associated in the development of opioid tolerance and dependence (see also M. E. Fundytus, CNS Drugs 15:29-58, (2001)). Very recently, it has been shown that antisense oligonucleotide knockdown of mGluR1 attenuates the development of opioid tolerance (R. N. Sharif et al., Brit. J. Pharmacol. 136:865-872 (2002)). Selective antagonists of the mGluR5 receptor have also been shown to exert anti-dependence activity in vivo (C. Chiamulera et al., Nature Neurosci. 4:873-874 (2001)).

Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks. Antagonists of the mGluR5 receptor have also been shown to exert anxiolytic and anti-depressant activity in in vivo animal models (E. Tatarczynska et al., Brit. J. Pharmacol. 132(7):1423-1430 (2001) and P. J. M. Will et al., Trends Pharmacol. Sci. 22(7):331-37 (2001)).

Examples of drugs for treating a seizure and epilepsy include carbamazepine, ethosuximide, gabapentin, lamotrigine, phenobarbital, phenyloin, primidone, valproic acid, trimethadione, benzodiazepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345-350 (R. Berkow ed., 1997).

Symptoms of strokes vary depending on what part of the brain is affected. Symptoms include loss of or abnormal sensations in an arm or leg or one side of the body, weakness or paralysis of an arm or leg or one side of the body, partial loss of vision or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352-355 (R. Berkow ed., 1997).

Pruritus is an unpleasant sensation that prompts scratching. Conventionally, pruritus is treated by phototherapy with ultraviolet B or PUVA or with therapeutic agents such as naltrexone, nalmefene, danazol, and tricyclic antidepressants.

Selective antagonists of mGluR5 have been shown to exert analgesic activity in in vivo animal models (K. Walker et al., Neuropharmacol. 40:1-9 (2000) and A. Dogrul et al., Neurosci. Let. 292(2):115-118 (2000)).

Selective antagonists of the mGluR5 receptor have also been shown to exert anti-Parkinson activity in vivo (K. J. Ossowska et al., Neuropharmacol. 41(4):413-20 (2001) and P. J. M. Will et al., Trends Pharmacol. Sci. 22(7):331-37 (2001)).

Selective antagonists of the mGluR5 receptor have also been shown to exert anti-dependence activity in vivo (C. Chiamulera et al., Nature Neurosci. 4(9):873-74 (2001)).

U.S. Pat. Nos. 6,156,908 and 6,492,541 B2 to Drauz et al. each disclose a procedure for the manufacture of 3-amino-2-oxo-pyrrolidines.

U.S. Pat. No. 6,248,756 B1 to Anthony et al. discloses nitrogen-heterocyclic compounds useful as farnesyl-protein transferase inhibitors.

International Publication No. WO 92/02502 by Smith Kline & French Laboratories Ltd. discloses N-hydrocarbyl-4-substituted piperidines useful as calcium blocking agents.

International Publication No. WO 99/37304 by Rohne-Poulenc Rorer Pharmaceuticals, Inc. discloses oxoazaheterocyclic compounds useful for inhibiting factor Xa.

International Publication No. WO 00/47553 by Cor Therapeutics, Inc. discloses alkynyl compounds useful for inhibiting factor Xa.

International Publication No. WO 01/17992 by Merck & Co. discloses pyrrolidine compounds useful for inhibiting prenyl-protein transferase.

International Publication No. WO 01/96331 by Bristol-Myers Squibb Co. discloses lactam compounds useful for inhibiting factor Xa.

There remains, however, a clear need in the art for new drugs useful for treating or preventing pain, UI, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

Citation of any reference in Section 2 of this application is not to be construed as an admission that such reference is prior art to the present application.

3. SUMMARY OF THE INVENTION

The present invention encompasses compounds of formula (I):

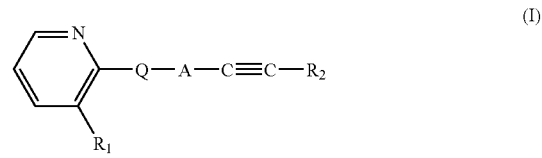

(I)

and pharmaceutically acceptable salts thereof, where:
R₁ is -halo, —CH₃, —CF₃, —NO₂, —CN, or —H;
Q is:

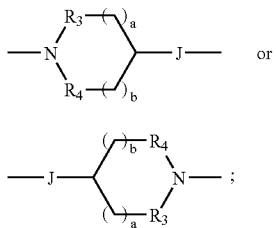

R₃ and R₄ are independently —CH₂—, —CH(CH₃)— or —C(O)—;
J is —N(H)— or —O—;
A is —C(O)— or —CH₂—;
R₂ is —(C₁-C₆)alkyl, —(C₃-C₈)cycloalkyl, -phenyl, -naphthyl, —(C₁₄)aryl, -(5- to 10-membered)heteroaryl, -(3- to 7-membered)heterocycle, or -(7- to 10-membered) bicycloheterocycle, each of which is unsubstituted or substituted with one or more R₅ groups;
R₅ is -halo, —(C₁-C₆)alkyl, —(C₁-C₆)alkoxy or —OC(halo)₃;
a and b are independently 0, 1 or 2; and
each halo is independently —F, —Cl, —Br or —I.

A compound of formula (I) or a pharmaceutically acceptable salt thereof (a "Pyridine-alkynyl Compound") is useful for treating or preventing pain, UI, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, ALS, dementia, retinopathy, a muscle spasm, a migraine, vomiting, dyskinesia, or depression (each being a "Condition") in an animal.

The invention also relates to compositions comprising an effective amount of a Pyridine-alkynyl Compound and a pharmaceutically acceptable carrier or excipient. The compositions are useful for treating or preventing a Condition in an animal.

The invention further relates to methods for treating a Condition comprising administering to an animal in need thereof an effective amount of a Pyridine-alkynyl Compound.

The invention further relates to methods for preventing a Condition comprising administering to an animal in need thereof an effective amount of a Pyridine-alkynyl Compound.

The invention still further relates to methods for inhibiting mGluR5 function in a cell, comprising contacting a cell capable of expressing mGluR5 with an effective amount of a Pyridine-alkynyl Compound.

The invention still further relates to methods for inhibiting mGluR1 function in a cell, comprising contacting a cell capable of expressing mGluR1 with an effective amount of a Pyridine-alkynyl Compound.

The invention still further relates to a method for preparing a composition comprising the step of admixing a Pyridine-alkynyl Compound and a pharmaceutically acceptable carrier or excipient.

The invention still further relates to a kit comprising a container containing an effective amount of a Pyridine-alkynyl Compound. The kit may further comprise printed instructions for using the Pyridine-alkynyl Compound to treat any of the aforementioned indications.

The present invention can be understood more fully by reference to the following detailed description and illustrative examples, which are intended to exemplify non-limiting embodiments of the invention.

4. DETAILED DESCRIPTION OF THE INVENTION

The present invention encompasses compounds of formula (I):

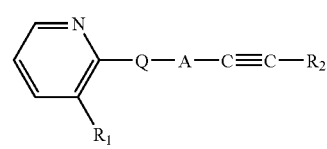

and pharmaceutically acceptable salts thereof, where:
R₁ is -halo, —CH₃, —CF₃, —NO₂, —CN, or —H;
Q is:

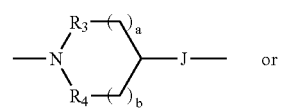

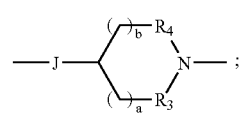

R₃ and R₄ are independently —CH₂—, —CH(CH₃)— or —C(O)—;
J is —N(H)— or —O—;
A is —C(O)— or —CH₂—;
R₂ is —(C₁-C₆)alkyl, —(C₃-C₈)cycloalkyl, -phenyl, -naphthyl, —(C₁₄)aryl, -(5- to 10-membered)heteroaryl, -(3- to 7-membered)heterocycle, or -(7- to 10-membered) bicycloheterocycle, each of which is unsubstituted or substituted with one or more R₅ groups;
R₅ is -halo, —(C₁-C₆)alkyl, —(C₁-C₆)alkoxy or —OC(halo)₃;
a and b are independently 0, 1 or 2; and
each halo is independently —F, —Cl, —Br or —I.

In one embodiment, in the compound of formula (I); A is —C(O)—.
In another embodiment, A is —CH₂—.
In another embodiment, R₁ is —F, —Cl, —CH₃, —CF₃, —NO₂, —CN, or —H.
In another embodiment, R₁ is —F, —Cl, —CH₃, —CF₃, —NO₂, or —H.
In another embodiment, a is 0 and b is 0.
In another embodiment, a is 0 and b is 1.
In another embodiment, a is 0 and b is 2.
In another embodiment, a is 1 and b is 0.
In another embodiment, a is 1 and b is 1.
In another embodiment, a is 1 and b is 2.
In another embodiment, a is 2 and b is 0.
In another embodiment, a is 2 and b is 1.
In another embodiment, a is 2 and b is 2.
In another embodiment, a is 0 and b is 0, or a is 0 and b is 1, or a is 1 and b is 0.

In another embodiment, a is 0 and b is 0, or a is 1 and b is 1, or a is 1 and b is 2, or a is 2 and b is 1, or a is 2 and b is 2.

In another embodiment, a is 0 and b is 0, or a is 0 and b is 1, or a is 1 and b is 0, or a is 1 and b is 2, or a is 2 and b is 1, or a is 2 and b is 2.

In another embodiment, a is 0 and b is 0, or a is 0 and b is 1, or a is 1 and b is 0, or a is 2 and b is 2.

In another embodiment, A is —C(O)—; and a is 0 and b is 0, or a is 1 and b is 1, or a is 1 and b is 2, or a is 2 and b is 1, or a is 2 and b is 2.

In another embodiment, J is —O—; and a is 0 and b is 0, or a is 1 and b is 1, or a is 1 and b is 2, or a is 2 and b is 1, or a is 2 and b is 2.

In another embodiment, $R_3$ and $R_4$ are each —$CH_2$—.

In another embodiment, $R_3$ is —$CH_2$— and $R_4$ is —CH($CH_3$)—.

In another embodiment, $R_3$ is —$CH_2$—, $R_4$ is —CH($CH_3$)—, and the carbon atom to which the $R_4$ methyl group of —CH($CH_3$)— is attached is in the (R) configuration.

In another embodiment, $R_3$ is —$CH_2$—, $R_4$ is —CH($CH_3$)—, and the carbon atom to which the $R_4$ methyl group of —CH($CH_3$)— is attached is in the (S) configuration.

In another embodiment, $R_3$ is —$CH_2$— and $R_4$ is —C(O)—.

In another embodiment, $R_3$ is —CH($CH_3$)— and $R_4$ is —$CH_2$—.

In another embodiment, $R_3$ is —CH($CH_3$)—, $R_4$ is —$CH_2$—, and the carbon atom to which the $R_3$ methyl group of —CH($CH_3$)— is attached is in the (R) configuration.

In another embodiment, $R_3$ is —CH($CH_3$)—, $R_4$ is —$CH_2$—, and the carbon atom to which the $R_3$ methyl group of —CH($CH_3$)— is attached is in the (S) configuration.

In another embodiment, $R_3$ and $R_4$ are each —CH($CH_3$)—.

In another embodiment, $R_3$ and $R_4$ are each —CH($CH_3$)—, the carbon atom to which the $R_3$ methyl group of —CH($CH_3$)— is attached is in the (R) configuration, and the carbon atom to which the $R_4$ methyl group of —CH($CH_3$)— is attached is in the (R) configuration.

In another embodiment, $R_3$ and $R_4$ are each —CH($CH_3$)—, the carbon atom to which the $R_3$ methyl group of —CH($CH_3$)— is attached is in the (S) configuration, and the carbon atom to which the $R_4$ methyl group of —CH($CH_3$)— is attached is in the (R) configuration.

In another embodiment, $R_3$ and $R_4$ are each —CH($CH_3$)—, the carbon atom to which the $R_3$ methyl group of —CH($CH_3$)— is attached is in the (R) configuration, and the carbon atom to which the $R_4$ methyl group of —CH($CH_3$)— is attached is in the (S) configuration.

In another embodiment, $R_3$ and $R_4$ are each —CH($CH_3$)—, the carbon atom to which the $R_3$ methyl group of —CH($CH_3$)— is attached is in the (S) configuration, and the carbon atom to which the $R_4$ methyl group of —CH($CH_3$)— is attached is in the (S) configuration.

In another embodiment, $R_3$ is —CH($CH_3$)— and $R_4$ is —C(O)—.

In another embodiment, $R_3$ is —C(O)— and $R_4$ is —$CH_2$—.

In another embodiment, $R_3$ is —C(O)— and $R_4$ is —CH($CH_3$)—.

In another embodiment, $R_3$ is —C(O)—, $R_4$ is —CH($CH_3$)—, and the carbon atom to which the $R_4$ methyl group of —CH($CH_3$)— is attached is in the (R) configuration.

In another embodiment, $R_3$ is —C(O)—, $R_4$ is —CH($CH_3$)—, and the carbon atom to which the $R_4$ methyl group of —CH($CH_3$)— is attached is in the (S) configuration.

In another embodiment, $R_3$ and $R_4$ are each —C(O)—.

In another embodiment, at least one of $R_3$ or $R_4$ is —CH($CH_3$)—.

In another embodiment, at least one of $R_3$ or $R_4$ is —CH($CH_3$)— and the carbon atom to which the $R_3$ and/or $R_4$ methyl group of —CH($CH_3$)— is attached is in the (R) configuration.

In another embodiment, at least one of $R_3$ or $R_4$ is —CH($CH_3$)— and the carbon atom to which the $R_3$ and/or $R_4$ methyl group of —CH($CH_3$)— is attached is in the (S) configuration.

In another embodiment, at least one of $R_3$ or $R_4$ is —C(O)—.

In another embodiment, when $R_3$ is —C(O)— or —CH($CH_3$)—, $R_4$ is —C(O)— or —CH($CH_3$)—.

In another embodiment, when $R_3$ is —($CH_2$)— or —CH($CH_3$)—, $R_4$ is —($CH_2$)— or —CH($CH_3$)—.

In another embodiment, J is —N(H)—.

In another embodiment, J is —O—.

In another embodiment, $R_2$ is substituted with one to three $R_5$ groups.

In another embodiment, $R_2$ is substituted with one or two $R_5$ groups.

In another embodiment, $R_2$ is unsubstituted.

In another embodiment, $R_2$ is —($C_1$-$C_6$)alkyl or —($C_3$-$C_8$)cycloalkyl, each of which is unsubstituted or substituted with one or more $R_5$ groups.

In another embodiment, $R_2$ is —($C_1$-$C_6$)alkyl which is unsubstituted or substituted with one or more $R_5$ groups.

In another embodiment, $R_2$ is —($C_1$-$C_6$)alkyl which is unsubstituted.

In another embodiment, $R_2$ is —($C_1$-$C_4$)alkyl which is unsubstituted or substituted with one or more $R_5$ groups.

In another embodiment, $R_2$ is —($C_1$-$C_4$)alkyl which is unsubstituted.

In another embodiment, $R_2$ is —($C_3$-$C_8$)cycloalkyl which is unsubstituted or substituted with one or more $R_5$ groups.

In another embodiment, $R_2$ is —($C_3$-$C_8$)cycloalkyl which is unsubstituted.

In another embodiment, $R_2$ is -cyclohexyl which is unsubstituted or substituted with one or more $R_5$ groups.

In another embodiment, $R_2$ is -cyclohexyl substituted in its 4-position with an $R_5$ group.

In another embodiment, $R_2$ is -cyclohexyl substituted in its 4-position with a —($C_1$-$C_6$)alkyl group.

In another embodiment, $R_2$ is -cyclohexyl substituted in its 4-position with a —($C_1$-$C_4$)alkyl group.

In another embodiment, $R_2$ is -cyclohexyl which is unsubstituted.

In another embodiment, $R_2$ is -phenyl, -naphthyl, or —($C_{14}$)aryl, each of which is unsubstituted or substituted with one or more $R_5$ groups.

In another embodiment, $R_2$ is unsubstituted -phenyl.

In another embodiment, $R_2$ is -phenyl substituted with one or more $R_5$ groups.

In another embodiment, $R_2$ is -phenyl substituted in its 4-position with an $R_5$ group.

In another embodiment, $R_2$ is -phenyl substituted in its 4-position with a —($C_1$-$C_6$)alkyl group.

In another embodiment, $R_2$ is -phenyl substituted in its 4-position with a —($C_1$-$C_4$)alkyl group.

In another embodiment, $R_2$ is -(3- to 7-membered)heterocycle or -(7- to 10-membered) bicycloheterocycle, each of which is unsubstituted or substituted with one or more $R_5$ groups.

In another embodiment, $R_2$ is -(3- to 7-membered)heterocycle which is unsubstituted or substituted with one or more $R_5$ groups.

In another embodiment, R₂ is -(3- to 7-membered)heterocycle which is unsubstituted.

In another embodiment, R₂ is -piperazinyl which is unsubstituted or substituted with one or more R₅ groups.

In another embodiment, R₂ is -piperazinyl, one nitrogen atom of which is bonded to the carbon atom of the carbon-carbon triple bond that is not bonded to -A-, the other nitrogen atom of which is substituted with a R₅ group.

In another embodiment, R₂ is -piperazinyl, one nitrogen atom of which is bonded to the carbon atom of the carbon-carbon triple bond that is not bonded to -A-, the other nitrogen atom of which is substituted with a —(C₁-C₆)alkyl group.

In another embodiment, R₂ is -piperazinyl, one nitrogen atom of which is bonded to the carbon atom of the carbon-carbon triple bond that is not bonded to -A-, the other nitrogen atom of which is substituted with a —(C₁-C₄)alkyl group.

In another embodiment, R₂ is -piperazinyl, one nitrogen atom of which is bonded to the carbon atom of the carbon-carbon triple bond that is not bonded to -A-, the other nitrogen atom of which is substituted with a methyl group.

In another embodiment, R₂ is -piperazinyl which is unsubstituted.

In another embodiment, R₂ is -piperazinyl which is unsubstituted, one nitrogen atom of which is bonded to the carbon atom of the carbon-carbon triple bond that is not bonded to -A-.

In another embodiment, R₂ is -morpholinyl which is unsubstituted or substituted with one or more R₅ groups.

In another embodiment, R₂ is -morpholinyl, the nitrogen atom of which is bonded to the carbon atom of the carbon-carbon triple bond that is not bonded to -A-, the -morpholinyl being unsubstituted or substituted with one or more R₅ groups.

In another embodiment, R₂ is -morpholinyl which is unsubstituted.

In another embodiment, R₂ is -morpholinyl which is unsubstituted, the nitrogen atom of which is bonded to the carbon atom of the carbon-carbon triple bond that is not bonded to -A-.

In another embodiment, R₂ is -(7- to 10-membered) bicycloheterocycle which is unsubstituted or substituted with one or more R₅ groups.

In another embodiment, R₂ is -(7- to 10-membered) bicycloheterocycle which is unsubstituted.

In another embodiment, R₂ is benzothiazole, benzimidazole or benzoxazole, which is unsubstituted or substituted with one or more R₅ groups.

In another embodiment, R₅ is —F, —Cl, —I, —(C₁-C₆)alkyl, —(C₁-C₆)alkoxy, —OCF₃, —OCF₂Cl, —OCCl₂F, —OCCl₃, or —OCI₃.

In another embodiment, R₅ is —F, —Cl, —I, —Br, methyl, ethyl, isopropyl, tert-butyl, —OCH₃ or —OCF₃.

In another embodiment, R₅ is —F, —Cl, —I, methyl, ethyl, isopropyl, tert-butyl, —OCH₃ or —OCF₃.

In another embodiment, A is —C(O)— and Q is:

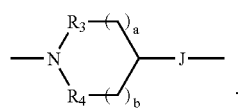

In another embodiment, A is —C(O)— and Q is:

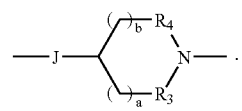

In another embodiment, A is —C(O)— and Q is:

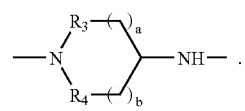

In another embodiment, A is —C(O)— and Q is:

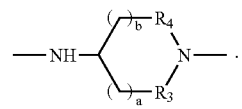

In another embodiment, A is —C(O)— and Q is:

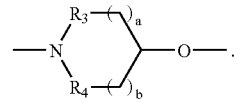

In another embodiment, A is —C(O)— and Q is:

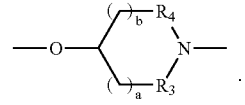

In another embodiment, A is —CH₂— and Q is:

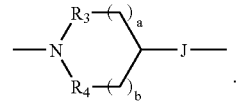

In another embodiment, A is —CH₂— and Q is:

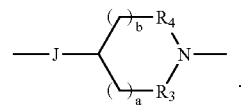

In another embodiment, A is —CH$_2$— and Q is:

[chemical structure: —N(R$_3$-()$_a$)(R$_4$-()$_b$)—NH—]

In another embodiment, A is —CH$_2$— and Q is:

[chemical structure: —NH—()$_b$R$_4$—N—()$_a$R$_3$—]

In another embodiment, A is —CH$_2$— and Q is:

[chemical structure: —N(R$_3$-()$_a$)(R$_4$-()$_b$)—O—]

In another embodiment, A is —CH$_2$— and Q is:

[chemical structure: —O—()$_b$R$_4$—N—()$_a$R$_3$—]

In another embodiment, a is 0, b is 0, and R$_3$ and R$_4$ are each —CH$_2$—.

In another embodiment, a is 1, b is 1, and R$_3$ and R$_4$ are each —CH$_2$—.

In another embodiment, a is 2, b is 2, and R$_3$ and R$_4$ are each —CH$_2$—.

In another embodiment, A is —CH$_2$—, a is 0, b is 0, and R$_3$ and R$_4$ are independently —CH$_2$— or —CH(CH$_3$)—.

In another embodiment, A is —CH$_2$—, a is 0, b is 0, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (R) configuration.

In another embodiment, A is —CH$_2$—, a is 0, b is 0, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (S) configuration.

In another embodiment, A is —CH$_2$—, a is 1, b is 1, and R$_3$ and R$_4$ are independently —CH$_2$— or —CH(CH$_3$)—.

In another embodiment, A is —CH$_2$—, a is 1, b is 1, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (R) configuration.

In another embodiment, A is —CH$_2$—, a is 1, b is 1, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (S) configuration.

In another embodiment, A is —CH$_2$—, a is 2, b is 2, and R$_3$ and R$_4$ are independently —CH$_2$— or —CH(CH$_3$)—.

In another embodiment, A is —CH$_2$—, a is 2, b is 2, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (R) configuration.

In another embodiment, A is —CH$_2$—, a is 2, b is 2, R$_3$ and R$_4$ are independently —CH$_2$— or —CH(CH$_3$)—, and each carbon atom to which the R$_3$ and/or R$_4$ methyl group of —CH(CH$_3$)— is attached, if present, is in the (S) configuration.

In another embodiment, A is —CH$_2$—, a is 1, b is 0, and R$_4$ is —CH$_2$— or —CH(CH$_3$)—.

In another embodiment, A is —CH$_2$—, a is 1, b is 0, R$_4$ is —CH$_2$— or —CH(CH$_3$)—, and the carbon atom to which the R$_4$ methyl group of —CH(CH$_3$)— is attached, if present, is in the (R) configuration.

In another embodiment, A is —CH$_2$—, a is 1, b is 0, R$_4$ is —CH$_2$— or —CH(CH$_3$)—, and the carbon atom to which the R$_4$ methyl group of —CH(CH$_3$)— is attached, if present, is in the (S) configuration.

In another embodiment, A is —CH$_2$—, a is 0, b is 1, and R$_3$ is —CH$_2$— or —CH(CH$_3$)—.

In another embodiment, A is —CH$_2$—, a is 0, b is 1, R$_3$ is —CH$_2$— or —CH(CH$_3$)—, and the carbon atom to which the R$_3$ methyl group of —CH(CH$_3$)— is attached, if present, is in the (R) configuration.

In another embodiment, A is —CH$_2$—, a is 0, b is 1, R$_3$ is —CH$_2$— or —CH(CH$_3$)—, and the carbon atom to which the R$_3$ methyl group of —CH(CH$_3$)— is attached, if present, is in the (S) configuration.

In another embodiment, A is —CH$_2$—, a is 2, b is 1, and R$_4$ is —CH$_2$— or —CH(CH$_3$)—.

In another embodiment, A is —CH$_2$—, a is 2, b is 1, R$_4$ is —CH$_2$— or —CH(CH$_3$)—, and the carbon atom to which the R$_4$ methyl group of —CH(CH$_3$)— is attached, if present, is in the (R) configuration.

In another embodiment, A is —CH$_2$—, a is 2, b is 1, R$_4$ is —CH$_2$— or —CH(CH$_3$)—, and the carbon atom to which the R$_4$ methyl group of —CH(CH$_3$)— is attached, if present, is in the (S) configuration.

In another embodiment, A is —CH$_2$—, a is 1, b is 2, and R$_3$ is —CH$_2$— or —CH(CH$_3$)—.

In another embodiment, A is —CH$_2$—, a is 1, b is 2, R$_3$ is —CH$_2$— or —CH(CH$_3$)—, and the carbon atom to which the R$_3$ methyl group of —CH(CH$_3$)— is attached, if present, is in the (R) configuration.

In another embodiment, A is —CH$_2$—, a is 1, b is 2, R$_3$ is —CH$_2$— or —CH(CH$_3$)—, and the carbon atom to which the R$_3$ methyl group of —CH(CH$_3$)— is attached, if present, is in the (S) configuration.

In another embodiment A is —C(O)— and R$_1$ is -halo.

In another embodiment A is —C(O)—; R$_1$ is -halo; and R$_3$ is —C(O)—.

In another embodiment A is —C(O)—; R$_1$ is -halo; and R$_4$ is —C(O)—.

In another embodiment A is —C(O)—; R$_1$ is -halo; and R$_2$ is —(C$_1$-C$_6$)alkyl which is unsubstituted or substituted with one or more R$_5$ groups.

In another embodiment A is —C(O)—; R$_1$ is -halo; and R$_2$ is —(C$_1$-C$_6$)alkyl.

In another embodiment A is —C(O)—; $R_1$ is -halo; and $R_2$ is —($C_1$-$C_4$)alkyl which is unsubstituted or substituted with one or more $R_5$ groups.

In another embodiment A is —C(O)—; $R_1$ is -halo; and $R_2$ is —($C_1$-$C_4$)alkyl.

In another embodiment A is —C(O)—; $R_1$ is -halo; and $R_2$ is —($C_3$-$C_8$)cycloalkyl which is unsubstituted or substituted with one or more $R_5$ groups.

In another embodiment A is —C(O)—; $R_1$ is -halo; and $R_2$ is —($C_3$-$C_8$)cycloalkyl.

In another embodiment A is —C(O)—; $R_1$ is -halo; and $R_2$ is -phenyl which is unsubstituted or substituted with one or more $R_5$ groups.

In another embodiment A is —C(O)—; $R_1$ is -halo; and $R_2$ is -phenyl.

In another embodiment A is —C(O)—; $R_1$ is -halo; and $R_2$ is -naphthyl which is unsubstituted or substituted with one or more $R_5$ groups.

In another embodiment A is —C(O)—; $R_1$ is -halo; and $R_2$ is -naphthyl.

In another embodiment A is —C(O)—; $R_1$ is -halo; and $R_2$ is —($C_{14}$)aryl which is unsubstituted or substituted with one or more $R_5$ groups.

In another embodiment A is —C(O)—; $R_1$ is -halo; and $R_2$ is —($C_{14}$)aryl.

In another embodiment A is —C(O)—; $R_1$ is -halo; and $R_2$ is -(5- to 10-membered)heteroaryl which is unsubstituted or substituted with one or more $R_5$ groups.

In another embodiment A is —C(O)—; $R_1$ is -halo; and $R_2$ is -(5- to 10-membered)heteroaryl.

In another embodiment A is —C(O)—; $R_1$ is -halo; and $R_2$ is -(3- to 7-membered)heterocycle which is unsubstituted or substituted with one or more $R_5$ groups.

In another embodiment A is —C(O)—; $R_1$ is -halo; and $R_2$ is -(3- to 7-membered)heterocycle.

In another embodiment A is —C(O)—; $R_1$ is -halo; and $R_2$ is -(7- to 10-membered) bicycloheterocycle which is unsubstituted or substituted with one or more $R_5$ groups.

In another embodiment A is —C(O)—; $R_1$ is -halo; and $R_2$ is -(7- to 10-membered) bicycloheterocycle.

In another embodiment A is —CH$_2$— and $R_1$ is -halo.

In another embodiment A is —CH$_2$—; $R_1$ is -halo; and $R_3$ is —C(O)—.

In another embodiment A is —CH$_2$—; $R_1$ is -halo; and $R_4$ is —C(O)—.

In another embodiment A is —CH$_2$—; $R_1$ is -halo; and $R_2$ is —($C_1$-$C_6$)alkyl which is unsubstituted or substituted with one or more $R_5$ groups.

In another embodiment A is —CH$_2$—; $R_1$ is -halo; and $R_2$ is —($C_1$-$C_6$)alkyl.

In another embodiment A is —CH$_2$—; $R_1$ is -halo; and $R_2$ is —($C_1$-$C_4$)alkyl which is unsubstituted or substituted with one or more $R_5$ groups.

In another embodiment A is —CH$_2$—; $R_1$ is -halo; and $R_2$ is —($C_1$-$C_4$)alkyl.

In another embodiment A is —CH$_2$—; $R_1$ is -halo; and $R_2$ is —($C_3$-$C_8$)cycloalkyl which is unsubstituted or substituted with one or more $R_5$ groups.

In another embodiment A is —CH$_2$—; $R_1$ is -halo; and $R_2$ is —($C_3$-$C_8$)cycloalkyl.

In another embodiment A is —CH$_2$—; $R_1$ is -halo; and $R_2$ is -phenyl which is unsubstituted or substituted with one or more $R_5$ groups.

In another embodiment A is —CH$_2$—; $R_1$ is -halo; and $R_2$ is -phenyl.

In another embodiment A is —CH$_2$—; $R_1$ is -halo; and $R_2$ is -naphthyl which is unsubstituted or substituted with one or more $R_5$ groups.

In another embodiment A is —CH$_2$—; $R_1$ is -halo; and $R_2$ is -naphthyl.

In another embodiment A is —CH$_2$—; $R_1$ is -halo; and $R_2$ is —($C_{14}$)aryl which is unsubstituted or substituted with one or more $R_5$ groups.

In another embodiment A is —CH$_2$—; $R_1$ is -halo; and $R_2$ is —($C_{14}$)aryl.

In another embodiment A is —CH$_2$—; $R_1$ is -halo; and $R_2$ is -(5- to 10-membered)heteroaryl which is unsubstituted or substituted with one or more $R_5$ groups.

In another embodiment A is —CH$_2$—; $R_1$ is -halo; and $R_2$ is -(5- to 10-membered)heteroaryl.

In another embodiment A is —CH$_2$—; $R_1$ is -halo; and $R_2$ is -(3- to 7-membered)heterocycle which is unsubstituted or substituted with one or more $R_5$ groups.

In another embodiment A is —CH$_2$—; $R_1$ is -halo; and $R_2$ is -(3- to 7-membered)heterocycle.

In another embodiment A is —CH$_2$—; $R_1$ is -halo; and $R_2$ is -(7- to 10-membered) bicycloheterocycle which is unsubstituted or substituted with one or more $R_5$ groups.

In another embodiment A is —CH$_2$—; $R_1$ is -halo; and $R_2$ is -(7- to 10-membered) bicycloheterocycle.

In another embodiment A is —C(O)— and $R_1$ is —CH$_3$.

In another embodiment A is —C(O)—; $R_1$ is —CH$_3$; and $R_3$ is —C(O)—.

In another embodiment A is —C(O)—; $R_1$ is —CH$_3$; and $R_4$ is —C(O)—.

In another embodiment A is —C(O)—; $R_1$ is —CH$_3$; and $R_2$ is —($C_1$-$C_6$)alkyl which is unsubstituted or substituted with one or more $R_5$ groups.

In another embodiment A is —C(O)—; $R_1$ is —CH$_3$; and $R_2$ is —($C_1$-$C_6$)alkyl.

In another embodiment A is —C(O)—; $R_1$ is —CH$_3$; and $R_2$ is —($C_1$-$C_4$)alkyl which is unsubstituted or substituted with one or more $R_5$ groups.

In another embodiment A is —C(O)—; $R_1$ is —CH$_3$; and $R_2$ is —($C_1$-$C_4$)alkyl.

In another embodiment A is —C(O)—; $R_1$ is —CH$_3$; and $R_2$ is —($C_3$-$C_8$)cycloalkyl which is unsubstituted or substituted with one or more $R_5$ groups.

In another embodiment A is —C(O)—; $R_1$ is —CH$_3$; and $R_2$ is —($C_3$-$C_8$)cycloalkyl.

In another embodiment A is —C(O)—; $R_1$ is —CH$_3$; and $R_2$ is -phenyl which is unsubstituted or substituted with one or more $R_5$ groups.

In another embodiment A is —C(O)—; $R_1$ is —CH$_3$; and $R_2$ is -phenyl.

In another embodiment A is —C(O)—; $R_1$ is —CH$_3$; and $R_2$ is -naphthyl which is unsubstituted or substituted with one or more $R_5$ groups.

In another embodiment A is —C(O)—; $R_1$ is —CH$_3$; and $R_2$ is -naphthyl.

In another embodiment A is —C(O)—; $R_1$ is —CH$_3$; and $R_2$ is —($C_{14}$)aryl which is unsubstituted or substituted with one or more $R_5$ groups.

In another embodiment A is —C(O)—; $R_1$ is —CH$_3$; and $R_2$ is —($C_{14}$)aryl.

In another embodiment A is —C(O)—; $R_1$ is —CH$_3$; and $R_2$ is -(5- to 10-membered)heteroaryl which is unsubstituted or substituted with one or more $R_5$ groups.

In another embodiment A is —C(O)—; $R_1$ is —CH$_3$; and $R_2$ is -(5- to 10-membered)heteroaryl.

In another embodiment A is —C(O)—; $R_1$ is —$CH_3$; and $R_2$ is -(3- to 7-membered)heterocycle which is unsubstituted or substituted with one or more $R_5$ groups.

In another embodiment A is —C(O)—; $R_1$ is —$CH_3$; and $R_2$ is -(3- to 7-membered)heterocycle.

In another embodiment A is —C(O)—; $R_1$ is —$CH_3$; and $R_2$ is -(7- to 10-membered) bicycloheterocycle which is unsubstituted or substituted with one or more $R_5$ groups.

In another embodiment A is —C(O)—; $R_1$ is —$CH_3$; and $R_2$ is -(7- to 10-membered) bicycloheterocycle.

In another embodiment A is —$CH_2$— and $R_1$ is —$CH_3$.

In another embodiment A is —$CH_2$—; $R_1$ is —$CH_3$; and $R_3$ is —C(O)—.

In another embodiment A is —$CH_2$—; $R_1$ is —$CH_3$; and $R_4$ is —C(O)—.

In another embodiment A is —$CH_2$—; $R_1$ is —$CH_3$; and $R_2$ is —($C_1$-$C_6$)alkyl which is unsubstituted or substituted with one or more $R_5$ groups.

In another embodiment A is —$CH_2$—; $R_1$ is —$CH_3$; and $R_2$ is —($C_1$-$C_6$)alkyl.

In another embodiment A is —$CH_2$—; $R_1$ is —$CH_3$; and $R_2$ is —($C_1$-$C_4$)alkyl which is unsubstituted or substituted with one or more $R_5$ groups.

In another embodiment A is —$CH_2$—; $R_1$ is —$CH_3$; and $R_2$ is —($C_1$-$C_4$)alkyl.

In another embodiment A is —$CH_2$—; $R_1$ is —$CH_3$; and $R_2$ is —($C_3$-$C_8$)cycloalkyl which is unsubstituted or substituted with one or more $R_5$ groups.

In another embodiment A is —$CH_2$—; $R_1$ is —$CH_3$; and $R_2$ is —($C_3$-$C_8$)cycloalkyl.

In another embodiment A is —$CH_2$—; $R_1$ is —$CH_3$; and $R_2$ is -phenyl which is unsubstituted or substituted with one or more $R_5$ groups.

In another embodiment A is —$CH_2$—; $R_1$ is —$CH_3$; and $R_2$ is -phenyl.

In another embodiment A is —$CH_2$—; $R_1$ is —$CH_3$; and $R_2$ is -naphthyl which is unsubstituted or substituted with one or more $R_5$ groups.

In another embodiment A is —$CH_2$—; $R_1$ is —$CH_3$; and $R_2$ is -naphthyl.

In another embodiment A is —$CH_2$—; $R_1$ is —$CH_3$; and $R_2$ is —($C_{14}$)aryl which is unsubstituted or substituted with one or more $R_5$ groups.

In another embodiment A is —$CH_2$—; $R_1$ is —$CH_3$; and $R_2$ is —($C_{14}$)aryl.

In another embodiment A is —$CH_2$—; $R_1$ is —$CH_3$; and $R_2$ is -(5- to 10-membered)heteroaryl which is unsubstituted or substituted with one or more $R_5$ groups.

In another embodiment A is —$CH_2$—; $R_1$ is —$CH_3$; and $R_2$ is -(5- to 10-membered)heteroaryl.

In another embodiment A is —$CH_2$—; $R_1$ is —$CH_3$; and $R_2$ is -(3- to 7-membered)heterocycle which is unsubstituted or substituted with one or more $R_5$ groups.

In another embodiment A is —$CH_2$—; $R_1$ is —$CH_3$; and $R_2$ is -(3- to 7-membered)heterocycle.

In another embodiment A is —$CH_2$—; $R_1$ is —$CH_3$; and $R_2$ is -(7- to 10-membered) bicycloheterocycle which is unsubstituted or substituted with one or more $R_5$ groups.

In another embodiment A is —$CH_2$—; $R_1$ is —$CH_3$; and $R_2$ is -(7- to 10-membered) bicycloheterocycle.

In another embodiment A is —C(O)— and $R_1$ is —$CF_3$.

In another embodiment A is —C(O)—; $R_1$ is —$CF_3$; and $R_3$ is —C(O)—.

In another embodiment A is —C(O)—; $R_1$ is —$CF_3$; and $R_4$ is —C(O)—.

In another embodiment A is —C(O)—; $R_1$ is —$CF_3$; and $R_2$ is —($C_1$-$C_6$)alkyl which is unsubstituted or substituted with one or more $R_5$ groups.

In another embodiment A is —C(O)—; $R_1$ is —$CF_3$; and $R_2$ is —($C_1$-$C_6$)alkyl.

In another embodiment A is —C(O)—; $R_1$ is —$CF_3$; and $R_2$ is —($C_1$-$C_4$)alkyl which is unsubstituted or substituted with one or more $R_5$ groups.

In another embodiment A is —C(O)—; $R_1$ is —$CF_3$; and $R_2$ is —($C_1$-$C_4$)alkyl.

In another embodiment A is —C(O)—; $R_1$ is —$CF_3$; and $R_2$ is —($C_3$-$C_8$)cycloalkyl which is unsubstituted or substituted with one or more $R_5$ groups.

In another embodiment A is —C(O)—; $R_1$ is —$CF_3$; and $R_2$ is —($C_3$-$C_8$)cycloalkyl.

In another embodiment A is —C(O)—; $R_1$ is —$CF_3$; and $R_2$ is -phenyl which is unsubstituted or substituted with one or more $R_5$ groups.

In another embodiment A is —C(O)—; $R_1$ is —$CF_3$; and $R_2$ is -phenyl.

In another embodiment A is —C(O)—; $R_1$ is —$CF_3$; and $R_2$ is -naphthyl which is unsubstituted or substituted with one or more $R_5$ groups.

In another embodiment A is —C(O)—; $R_1$ is —$CF_3$; and $R_2$ is -naphthyl.

In another embodiment A is —C(O)—; $R_1$ is —$CF_3$; and $R_2$ is —($C_{14}$)aryl which is unsubstituted or substituted with one or more $R_5$ groups.

In another embodiment A is —C(O)—; $R_1$ is —$CF_3$; and $R_2$ is —($C_{14}$)aryl.

In another embodiment A is —C(O)—; $R_1$ is —$CF_3$; and $R_2$ is -(5- to 10-membered)heteroaryl which is unsubstituted or substituted with one or more $R_5$ groups.

In another embodiment A is —C(O)—; $R_1$ is —$CF_3$; and $R_2$ is -(5- to 10-membered)heteroaryl.

In another embodiment A is —C(O)—; $R_1$ is —$CF_3$; and $R_2$ is -(3- to 7-membered)heterocycle which is unsubstituted or substituted with one or more $R_5$ groups.

In another embodiment A is —C(O)—; $R_1$ is —$CF_3$; and $R_2$ is -(3- to 7-membered)heterocycle.

In another embodiment A is —C(O)—; $R_1$ is —$CF_3$; and $R_2$ is -(7- to 10-membered) bicycloheterocycle which is unsubstituted or substituted with one or more $R_5$ groups.

In another embodiment A is —C(O)—; $R_1$ is —$CF_3$; and $R_2$ is -(7- to 10-membered) bicycloheterocycle.

In another embodiment A is —$CH_2$— and $R_1$ is —$CF_3$.

In another embodiment A is —$CH_2$—; $R_1$ is —$CF_3$; and $R_3$ is —C(O)—.

In another embodiment A is —$CH_2$—; $R_1$ is —$CF_3$; and $R_4$ is —C(O)—.

In another embodiment A is —$CH_2$—; $R_1$ is —$CF_3$; and $R_2$ is —($C_1$-$C_6$)alkyl which is unsubstituted or substituted with one or more $R_5$ groups.

In another embodiment A is —$CH_2$—; $R_1$ is —$CF_3$; and $R_2$ is —($C_1$-$C_6$)alkyl.

In another embodiment A is —$CH_2$—; $R_1$ is —$CF_3$; and $R_2$ is —($C_1$-$C_4$)alkyl which is unsubstituted or substituted with one or more $R_5$ groups.

In another embodiment A is —$CH_2$—; $R_1$ is —$CF_3$; and $R_2$ is —($C_1$-$C_4$)alkyl.

In another embodiment A is —$CH_2$—; $R_1$ is —$CF_3$; and $R_2$ is —($C_3$-$C_8$)cycloalkyl which is unsubstituted or substituted with one or more $R_5$ groups.

In another embodiment A is —$CH_2$—; $R_1$ is —$CF_3$; and $R_2$ is —($C_3$-$C_8$)cycloalkyl.

In another embodiment A is —CH$_2$—; R$_1$ is —CF$_3$; and R$_2$ is -phenyl which is unsubstituted or substituted with one or more R$_5$ groups.

In another embodiment A is —CH$_2$—; R$_1$ is —CF$_3$; and R$_2$ is -phenyl.

In another embodiment A is —CH$_2$—; R$_1$ is —CF$_3$; and R$_2$ is -naphthyl which is unsubstituted or substituted with one or more R$_5$ groups.

In another embodiment A is —CH$_2$—; R$_1$ is —CF$_3$; and R$_2$ is -naphthyl.

In another embodiment A is —CH$_2$—; R$_1$ is —CF$_3$; and R$_2$ is —(C$_{14}$)aryl which is unsubstituted or substituted with one or more R$_5$ groups.

In another embodiment A is —CH$_2$—; R$_1$ is —CF$_3$; and R$_2$ is —(C$_{14}$)aryl.

In another embodiment A is —CH$_2$—; R$_1$ is —CF$_3$; and R$_2$ is -(5- to 10-membered)heteroaryl which is unsubstituted or substituted with one or more R$_5$ groups.

In another embodiment A is —CH$_2$—; R$_1$ is —CF$_3$; and R$_2$ is -(5- to 10-membered)heteroaryl.

In another embodiment A is —CH$_2$—; R$_1$ is —CF$_3$; and R$_2$ is -(3- to 7-membered)heterocycle which is unsubstituted or substituted with one or more R$_5$ groups.

In another embodiment A is —CH$_2$—; R$_1$ is —CF$_3$; and R$_2$ is -(3- to 7-membered)heterocycle.

In another embodiment A is —CH$_2$—; R$_1$ is —CF$_3$; and R$_2$ is -(7- to 10-membered) bicycloheterocycle which is unsubstituted or substituted with one or more R$_5$ groups.

In another embodiment A is —CH$_2$—; R$_1$ is —CF$_3$; and R$_2$ is -(7- to 10-membered) bicycloheterocycle.

In another embodiment A is —C(O)— and R$_1$ is —NO$_2$.

In another embodiment A is —C(O)—; R$_1$ is —NO$_2$; and R$_3$ is —C(O)—.

In another embodiment A is —C(O)—; R$_1$ is —NO$_2$; and R$_4$ is —C(O)—.

In another embodiment A is —C(O)—; R$_1$ is —NO$_2$; and R$_2$ is —(C$_1$-C$_6$)alkyl which is unsubstituted or substituted with one or more R$_5$ groups.

In another embodiment A is —C(O)—; R$_1$ is —NO$_2$; and R$_2$ is —(C$_1$-C$_6$)alkyl.

In another embodiment A is —C(O)—; R$_1$ is —NO$_2$; and R$_2$ is —(C$_1$-C$_4$)alkyl which is unsubstituted or substituted with one or more R$_5$ groups.

In another embodiment A is —C(O)—; R$_1$ is —NO$_2$; and R$_2$ is —(C$_1$-C$_4$)alkyl.

In another embodiment A is —C(O)—; R$_1$ is —NO$_2$; and R$_2$ is —(C$_3$-C$_8$)cycloalkyl which is unsubstituted or substituted with one or more R$_5$ groups.

In another embodiment A is —C(O)—; R$_1$ is —NO$_2$; and R$_2$ is —(C$_3$-C$_8$)cycloalkyl.

In another embodiment A is —C(O)—; R$_1$ is —NO$_2$; and R$_2$ is -phenyl which is unsubstituted or substituted with one or more R$_5$ groups.

In another embodiment A is —C(O)—; R$_1$ is —NO$_2$; and R$_2$ is -phenyl.

In another embodiment A is —C(O)—; R$_1$ is —NO$_2$; and R$_2$ is -naphthyl which is unsubstituted or substituted with one or more R$_5$ groups.

In another embodiment A is —C(O)—; R$_1$ is —NO$_2$; and R$_2$ is -naphthyl.

In another embodiment A is —C(O)—; R$_1$ is —NO$_2$; and R$_2$ is —(C$_{14}$)aryl which is unsubstituted or substituted with one or more R$_5$ groups.

In another embodiment A is —C(O)—; R$_1$ is —NO$_2$; and R$_2$ is —(C$_{14}$)aryl.

In another embodiment A is —C(O)—; R$_1$ is —NO$_2$; and R$_2$ is -(5- to 10-membered)heteroaryl which is unsubstituted or substituted with one or more R$_5$ groups.

In another embodiment A is —C(O)—; R$_1$ is —NO$_2$; and R$_2$ is -(5- to 10-membered)heteroaryl.

In another embodiment A is —C(O)—; R$_1$ is —NO$_2$; and R$_2$ is -(3- to 7-membered)heterocycle which is unsubstituted or substituted with one or more R$_5$ groups.

In another embodiment A is —C(O)—; R$_1$ is —NO$_2$; and R$_2$ is -(3- to 7-membered)heterocycle.

In another embodiment A is —C(O)—; R$_1$ is —NO$_2$; and R$_2$ is -(7- to 10-membered) bicycloheterocycle which is unsubstituted or substituted with one or more R$_5$ groups.

In another embodiment A is —C(O)—; R$_1$ is —NO$_2$; and R$_2$ is -(7- to 10-membered) bicycloheterocycle.

In another embodiment A is —CH$_2$— and R$_1$ is —NO$_2$.

In another embodiment A is —CH$_2$—; R$_1$ is —NO$_2$; and R$_3$ is —C(O)—.

In another embodiment A is —CH$_2$—; R$_1$ is —NO$_2$; and R$_4$ is —C(O)—.

In another embodiment A is —CH$_2$—; R$_1$ is —NO$_2$; and R$_2$ is —(C$_1$-C$_6$)alkyl which is unsubstituted or substituted with one or more R$_5$ groups.

In another embodiment A is —CH$_2$—; R$_1$ is —NO$_2$; and R$_2$ is —(C$_1$-C$_6$)alkyl.

In another embodiment A is —CH$_2$—; R$_1$ is —NO$_2$; and R$_2$ is —(C$_1$-C$_4$)alkyl which is unsubstituted or substituted with one or more R$_5$ groups.

In another embodiment A is —CH$_2$—; R$_1$ is —NO$_2$; and R$_2$ is —(C$_1$-C$_4$)alkyl.

In another embodiment A is —CH$_2$—; R$_1$ is —NO$_2$; and R$_2$ is —(C$_3$-C$_8$)cycloalkyl which is unsubstituted or substituted with one or more R$_5$ groups.

In another embodiment A is —CH$_2$—; R$_1$ is —NO$_2$; and R$_2$ is —(C$_3$-C$_8$)cycloalkyl.

In another embodiment A is —CH$_2$—; R$_1$ is —NO$_2$; and R$_2$ is -phenyl which is unsubstituted or substituted with one or more R$_5$ groups.

In another embodiment A is —CH$_2$—; R$_1$ is —NO$_2$; and R$_2$ is -phenyl.

In another embodiment A is —CH$_2$—; R$_1$ is —NO$_2$; and R$_2$ is -naphthyl which is unsubstituted or substituted with one or more R$_5$ groups.

In another embodiment A is —CH$_2$—; R$_1$ is —NO$_2$; and R$_2$ is -naphthyl.

In another embodiment A is —CH$_2$—; R$_1$ is —NO$_2$; and R$_2$ is —(C$_{14}$)aryl which is unsubstituted or substituted with one or more R$_5$ groups.

In another embodiment A is —CH$_2$—; R$_1$ is —NO$_2$; and R$_2$ is —(C$_{14}$)aryl.

In another embodiment A is —CH$_2$—; R$_1$ is —NO$_2$; and R$_2$ is -(5- to 10-membered)heteroaryl which is unsubstituted or substituted with one or more R$_5$ groups.

In another embodiment A is —CH$_2$—; R$_1$ is —NO$_2$; and R$_2$ is -(5- to 10-membered)heteroaryl.

In another embodiment A is —CH$_2$—; R$_1$ is —NO$_2$; and R$_2$ is -(3- to 7-membered)heterocycle which is unsubstituted or substituted with one or more R$_5$ groups.

In another embodiment A is —CH$_2$—; R$_1$ is —NO$_2$; and R$_2$ is -(3- to 7-membered)heterocycle.

In another embodiment A is —CH$_2$—; R$_1$ is —NO$_2$; and R$_2$ is -(7- to 10-membered) bicycloheterocycle which is unsubstituted or substituted with one or more R$_5$ groups.

In another embodiment A is —CH$_2$—; R$_1$ is —NO$_2$; and R$_2$ is -(7- to 10-membered) bicycloheterocycle.

In another embodiment A is —C(O)— and R$_1$ is —CN.

In another embodiment A is —C(O)—; R$_1$ is —CN; and R$_3$ is —C(O)—.

In another embodiment A is —C(O)—; R$_1$ is —CN; and R$_4$ is —C(O)—.

In another embodiment A is —C(O)—; R$_1$ is —CN; and R$_2$ is —(C$_1$-C$_6$)alkyl which is unsubstituted or substituted with one or more R$_5$ groups.

In another embodiment A is —C(O)—; R$_1$ is —CN; and R$_2$ is —(C$_1$-C$_6$)alkyl.

In another embodiment A is —C(O)—; R$_1$ is —CN; and R$_2$ is —(C$_1$-C$_4$)alkyl which is unsubstituted or substituted with one or more R$_5$ groups.

In another embodiment A is —C(O)—; R$_1$ is —CN; and R$_2$ is —(C$_1$-C$_4$)alkyl.

In another embodiment A is —C(O)—; R$_1$ is —CN; and R$_2$ is —(C$_3$-C$_8$)cycloalkyl which is unsubstituted or substituted with one or more R$_5$ groups.

In another embodiment A is —C(O)—; R$_1$ is —CN; and R$_2$ is —(C$_3$-C$_8$)cycloalkyl.

In another embodiment A is —C(O)—; R$_1$ is —CN; and R$_2$ is -phenyl which is unsubstituted or substituted with one or more R$_5$ groups.

In another embodiment A is —C(O)—; R$_1$ is —CN; and R$_2$ is -phenyl.

In another embodiment A is —C(O)—; R$_1$ is —CN; and R$_2$ is -naphthyl which is unsubstituted or substituted with one or more R$_5$ groups.

In another embodiment A is —C(O)—; R$_1$ is —CN; and R$_2$ is -naphthyl.

In another embodiment A is —C(O)—; R$_1$ is —CN; and R$_2$ is —(C$_{14}$)aryl which is unsubstituted or substituted with one or more R$_5$ groups.

In another embodiment A is —C(O)—; R$_1$ is —CN; and R$_2$ is —(C$_{14}$)aryl.

In another embodiment A is —C(O)—; R$_1$ is —CN; and R$_2$ is -(5- to 10-membered)heteroaryl which is unsubstituted or substituted with one or more R$_5$ groups.

In another embodiment A is —C(O)—; R$_1$ is —CN; and R$_2$ is -(5- to 10-membered)heteroaryl.

In another embodiment A is —C(O)—; R$_1$ is —CN; and R$_2$ is -(3- to 7-membered)heterocycle which is unsubstituted or substituted with one or more R$_5$ groups.

In another embodiment A is —C(O)—; R$_1$ is —CN; and R$_2$ is -(3- to 7-membered)heterocycle.

In another embodiment A is —C(O)—; R$_1$ is —CN; and R$_2$ is -(7- to 10-membered) bicycloheterocycle which is unsubstituted or substituted with one or more R$_5$ groups.

In another embodiment A is —C(O)—; R$_1$ is —CN; and R$_2$ is -(7- to 10-membered) bicycloheterocycle.

In another embodiment A is —CH$_2$— and R$_1$ is —CN.

In another embodiment A is —CH$_2$—; R$_1$ is —CN; and R$_3$ is —C(O)—.

In another embodiment A is —CH$_2$—; R$_1$ is —CN; and R$_4$ is —C(O)—.

In another embodiment A is —CH$_2$—; R$_1$ is —CN; and R$_2$ is —(C$_1$-C$_6$)alkyl which is unsubstituted or substituted with one or more R$_5$ groups.

In another embodiment A is —CH$_2$—; R$_1$ is —CN; and R$_2$ is —(C$_1$-C$_6$)alkyl.

In another embodiment A is —CH$_2$—; R$_1$ is —CN; and R$_2$ is —(C$_1$-C$_4$)alkyl which is unsubstituted or substituted with one or more R$_5$ groups.

In another embodiment A is —CH$_2$—; R$_1$ is —CN; and R$_2$ is —(C$_1$-C$_4$)alkyl.

In another embodiment A is —CH$_2$—; R$_1$ is —CN; and R$_2$ is —(C$_3$-C$_8$)cycloalkyl which is unsubstituted or substituted with one or more R$_5$ groups.

In another embodiment A is —CH$_2$—; R$_1$ is —CN; and R$_2$ is —(C$_3$-C$_8$)cycloalkyl.

In another embodiment A is —CH$_2$—; R$_1$ is —CN; and R$_2$ is -phenyl which is unsubstituted or substituted with one or more R$_5$ groups.

In another embodiment A is —CH$_2$—; R$_1$ is —CN; and R$_2$ is -phenyl.

In another embodiment A is —CH$_2$—; R$_1$ is —CN; and R$_2$ is -naphthyl which is unsubstituted or substituted with one or more R$_5$ groups.

In another embodiment A is —CH$_2$—; R$_1$ is —CN; and R$_2$ is -naphthyl.

In another embodiment A is —CH$_2$—; R$_1$ is —CN; and R$_2$ is —(C$_{14}$)aryl which is unsubstituted or substituted with one or more R$_5$ groups.

In another embodiment A is —CH$_2$—; R$_1$ is —CN; and R$_2$ is —(C$_{14}$)aryl.

In another embodiment A is —CH$_2$—; R$_1$ is —CN; and R$_2$ is -(5- to 10-membered)heteroaryl which is unsubstituted or substituted with one or more R$_5$ groups.

In another embodiment A is —CH$_2$—; R$_1$ is —CN; and R$_2$ is -(5- to 10-membered)heteroaryl.

In another embodiment A is —CH$_2$—; R$_1$ is —CN; and R$_2$ is -(3- to 7-membered)heterocycle which is unsubstituted or substituted with one or more R$_5$ groups.

In another embodiment A is —CH$_2$—; R$_1$ is —CN; and R$_2$ is -(3- to 7-membered)heterocycle.

In another embodiment A is —CH$_2$—; R$_1$ is —CN; and R$_2$ is -(7- to 10-membered) bicycloheterocycle which is unsubstituted or substituted with one or more R$_5$ groups.

In another embodiment A is —CH$_2$—; R$_1$ is —CN; and R$_2$ is -(7- to 10-membered) bicycloheterocycle.

In another embodiment A is —C(O)— and R$_1$ is —H.

In another embodiment A is —C(O)—; R$_1$ is —H; and R$_3$ is —C(O)—.

In another embodiment A is —C(O)—; R$_1$ is —H; and R$_4$ is —C(O)—.

In another embodiment A is —C(O)—; R$_1$ is —H; and R$_2$ is —(C$_1$-C$_6$)alkyl which is unsubstituted or substituted with one or more R$_5$ groups.

In another embodiment A is —C(O)—; R$_1$ is —H; and R$_2$ is —(C$_1$-C$_6$)alkyl.

In another embodiment A is —C(O)—; R$_1$ is —H; and R$_2$ is —(C$_1$-C$_4$)alkyl which is unsubstituted or substituted with one or more R$_5$ groups.

In another embodiment A is —C(O)—; R$_1$ is —H; and R$_2$ is —(C$_1$-C$_4$)alkyl.

In another embodiment A is —CH$_2$—; R$_1$ is —CN; and R$_2$ is —(C$_3$-C$_8$)cycloalkyl which is unsubstituted or substituted with one or more R$_5$ groups.

In another embodiment A is —CH$_2$—; R$_1$ is —CN; and R$_2$ is —(C$_3$-C$_8$)cycloalkyl.

In another embodiment A is —CH$_2$—; R$_1$ is —CN; and R$_2$ is -phenyl which is unsubstituted or substituted with one or more R$_5$ groups.

In another embodiment A is —CH$_2$—; R$_1$ is —CN; and R$_2$ is -phenyl.

In another embodiment A is —C(O)—; R$_1$ is —H; and R$_2$ is -naphthyl which is unsubstituted or substituted with one or more R$_5$ groups.

In another embodiment A is —C(O)—; R$_1$ is —H; and R$_2$ is -naphthyl.

In another embodiment A is —C(O)—; R$_1$ is —H; and R$_2$ is —(C$_{14}$)aryl which is unsubstituted or substituted with one or more R$_5$ groups.

In another embodiment A is —C(O)—; R$_1$ is —H; and R$_2$ is —(C$_{14}$)aryl.

In another embodiment A is —C(O)—; $R_1$ is —H; and $R_2$ is -(5- to 10-membered)heteroaryl which is unsubstituted or substituted with one or more $R_5$ groups.

In another embodiment A is —C(O)—; $R_1$ is —H; and $R_2$ is -(5- to 10-membered)heteroaryl.

In another embodiment A is —C(O)—; $R_1$ is —H; and $R_2$ is -(3- to 7-membered)heterocycle which is unsubstituted or substituted with one or more $R_5$ groups.

In another embodiment A is —C(O)—; $R_1$ is —H; and $R_2$ is -(3- to 7-membered)heterocycle.

In another embodiment A is —C(O)—; $R_1$ is —H; and $R_2$ is -(7- to 10-membered) bicycloheterocycle which is unsubstituted or substituted with one or more $R_5$ groups.

In another embodiment A is —C(O)—; $R_1$ is —H; and $R_2$ is -(7- to 10-membered) bicycloheterocycle.

In another embodiment A is —$CH_2$— and $R_1$ is —H.

In another embodiment A is —$CH_2$—; $R_1$ is —H; and $R_3$ is —C(O)—.

In another embodiment A is —$CH_2$—; $R_1$ is —H; and $R_4$ is —C(O)—.

In another embodiment A is —$CH_2$—; $R_1$ is —H; and $R_2$ is —($C_1$-$C_6$)alkyl which is unsubstituted or substituted with one or more $R_5$ groups.

In another embodiment A is —$CH_2$—; $R_1$ is —H; and $R_2$ is —($C_1$-$C_6$)alkyl.

In another embodiment A is —$CH_2$—; $R_1$ is —H; and $R_2$ is —($C_1$-$C_4$)alkyl which is unsubstituted or substituted with one or more $R_5$ groups.

In another embodiment A is —$CH_2$—; $R_1$ is —H; and $R_2$ is —($C_1$-$C_4$)alkyl.

In another embodiment A is —$CH_2$—; $R_1$ is —H; and $R_2$ is —($C_3$-$C_8$)cycloalkyl which is unsubstituted or substituted with one or more $R_5$ groups.

In another embodiment A is —$CH_2$—; $R_1$ is —H; and $R_2$ is —($C_3$-$C_8$)cycloalkyl.

In another embodiment A is —$CH_2$—; $R_1$ is —H; and $R_2$ is -phenyl which is unsubstituted or substituted with one or more $R_5$ groups.

In another embodiment A is —$CH_2$—; $R_1$ is —H; and $R_2$ is -phenyl.

In another embodiment A is —$CH_2$—; $R_1$ is —H; and $R_2$ is -naphthyl which is unsubstituted or substituted with one or more $R_5$ groups.

In another embodiment A is —$CH_2$—; $R_1$ is —H; and $R_2$ is -naphthyl.

In another embodiment A is —$CH_2$—; $R_1$ is —H; and $R_2$ is —($C_{14}$)aryl which is unsubstituted or substituted with one or more $R_5$ groups.

In another embodiment A is —$CH_2$—; $R_1$ is —H; and $R_2$ is —($C_{14}$)aryl.

In another embodiment A is —$CH_2$—; $R_1$ is —H; and $R_2$ is -(5- to 10-membered)heteroaryl which is unsubstituted or substituted with one or more $R_5$ groups.

In another embodiment A is —$CH_2$—; $R_1$ is —H; and $R_2$ is -(5- to 10-membered)heteroaryl.

In another embodiment A is —$CH_2$—; $R_1$ is —H; and $R_2$ is -(3- to 7-membered)heterocycle which is unsubstituted or substituted with one or more $R_5$ groups.

In another embodiment A is —$CH_2$—; $R_1$ is —H; and $R_2$ is -(3- to 7-membered)heterocycle.

In another embodiment A is —$CH_2$—; $R_1$ is —H; and $R_2$ is -(7- to 10-membered) bicycloheterocycle which is unsubstituted or substituted with one or more $R_5$ groups.

In another embodiment A is —$CH_2$—; $R_1$ is —H; and $R_2$ is -(7- to 10-membered) bicycloheterocycle.

Illustrative Pyridine-alkynyl Compounds are listed below in Tables 1 and 2:

TABLE 1

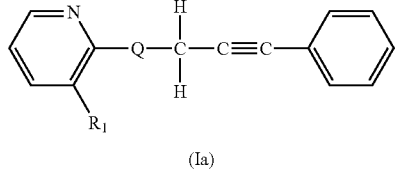

(Ia)

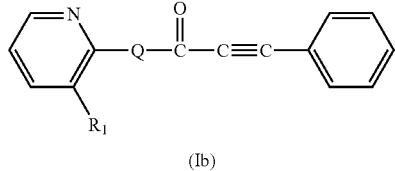

(Ib)

and pharmaceutically acceptable salts thereof, where

| Compound | Q | $R_1$ |
|---|---|---|
| AAA(Ia) or (Ib) | —NH—⬦N— | H |
| AAB(Ia) or (Ib) | —NH—⬦N— | $NO_2$ |
| AAC(Ia) or (Ib) | —NH—⬦N— | CN |
| AAD(Ia) or (Ib) | —NH—⬦N— | F |
| AAE(Ia) or (Ib) | —NH—⬦N— | Cl |
| AAF(Ia) or (Ib) | —NH—⬦N— | $CF_3$ |
| AAG(Ia) or (Ib) | —NH—⬦N— | $CH_3$ |
| AAH(Ia) or (Ib) | —NH—⬦($CH_3$)N— | H |
| AAI(Ia) or (Ib) | —NH—⬦($CH_3$)N— | $NO_2$ |
| AAJ(Ia) or (Ib) | —NH—⬦($CH_3$)N— | CN |
| AAK(Ia) or (Ib) | —NH—⬦($CH_3$)N— | F |

TABLE 1-continued

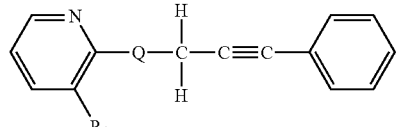

(Ia)

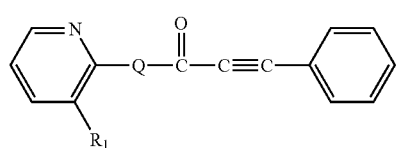

(Ib)

and pharmaceutically acceptable salts thereof, where

| Compound | Q | R₁ |
| --- | --- | --- |
| AAL(Ia) or (Ib) | —NH—[2-methylazetidin-3-yl] | Cl |
| AAM(Ia) or (Ib) | —NH—[2-methylazetidin-3-yl] | CF₃ |
| AAN(Ia) or (Ib) | —NH—[2-methylazetidin-3-yl] | CH₃ |
| AAO(Ia) or (Ib) | —NH—[2,4-dimethylazetidin-3-yl] | H |
| AAP(Ia) or (Ib) | —NH—[2,4-dimethylazetidin-3-yl] | NO₂ |
| AAQ(Ia) or (Ib) | —NH—[2,4-dimethylazetidin-3-yl] | CN |
| AAR(Ia) or (Ib) | —NH—[2,4-dimethylazetidin-3-yl] | F |

TABLE 1-continued

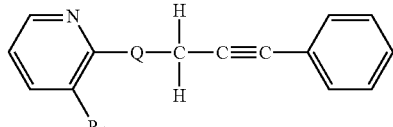

(Ia)

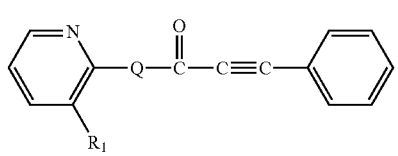

(Ib)

and pharmaceutically acceptable salts thereof, where

| Compound | Q | R₁ |
| --- | --- | --- |
| AAS(Ia) or (Ib) | —NH—[2,4-dimethylazetidin-3-yl] | Cl |
| AAT(Ia) or (Ib) | —NH—[2,4-dimethylazetidin-3-yl] | CF₃ |
| AAU(Ia) or (Ib) | —NH—[2,4-dimethylazetidin-3-yl] | CH₃ |
| AAV(Ia) or (Ib) | —NH—[2-oxoazetidin-3-yl] | H |
| AAW(Ia) or (Ib) | —NH—[2-oxoazetidin-3-yl] | NO₂ |
| AAX(Ia) or (Ib) | —NH—[2-oxoazetidin-3-yl] | CN |
| AAY(Ia) or (Ib) | —NH—[2-oxoazetidin-3-yl] | F |

TABLE 1-continued

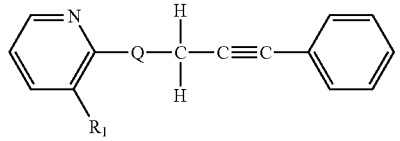

(Ia)

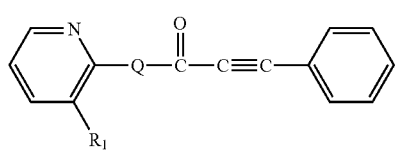

(Ib)

and pharmaceutically acceptable salts thereof, where

| Compound | Q | $R_1$ |
|---|---|---|
| AAZ(Ia) or (Ib) | 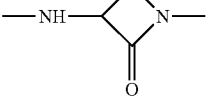 | Cl |
| ABA(Ia) or (Ib) | 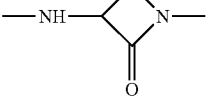 | $CF_3$ |
| ABB(Ia) or (Ib) | 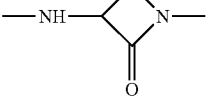 | $CH_3$ |
| ABC(Ia) or (Ib) | 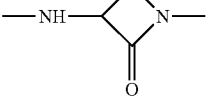 | H |
| ABD(Ia) or (Ib) | 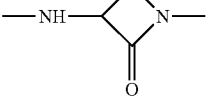 | $NO_2$ |
| ABE(Ia) or (Ib) | 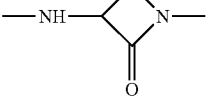 | CN |
| ABF(Ia) or (Ib) | 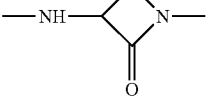 | F |

TABLE 1-continued

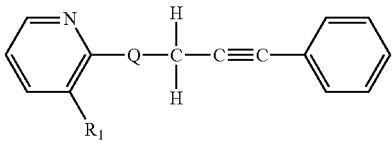

(Ia)

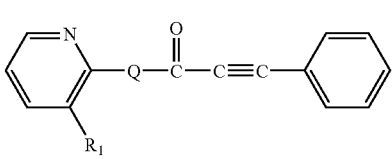

(Ib)

and pharmaceutically acceptable salts thereof, where

| Compound | Q | $R_1$ |
|---|---|---|
| ABG(Ia) or (Ib) | 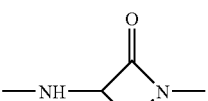 | Cl |
| ABH(Ia) or (Ib) | 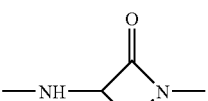 | $CF_3$ |
| ABI(Ia) or (Ib) | 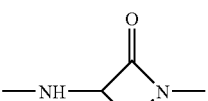 | $CH_3$ |
| ABJ(Ia) or (Ib) | 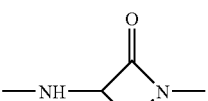 | H |
| ABK(Ia) or (Ib) | 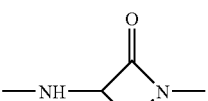 | $NO_2$ |
| ABL(Ia) or (Ib) | 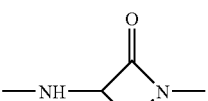 | CN |

TABLE 1-continued

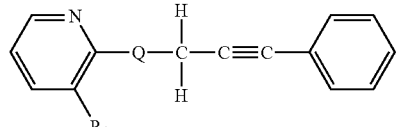

(Ia)

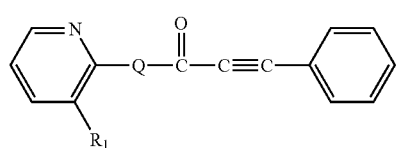

(Ib)

and pharmaceutically acceptable salts thereof, where

| Compound | Q | R₁ |
|---|---|---|
| ABM(Ia) or (Ib) | —NH-(2-methyl-1-methyl-azetidin-3-one-yl) | F |
| ABN(Ia) or (Ib) | —NH-(2-methyl-1-methyl-azetidin-3-one-yl) | Cl |
| ABO(Ia) or (Ib) | —NH-(2-methyl-1-methyl-azetidin-3-one-yl) | CF₃ |
| ABP(Ia) or (Ib) | —NH-(2-methyl-1-methyl-azetidin-3-one-yl) | CH₃ |
| ABQ(Ia) or (Ib) | —NH-(1-methylpyrrolidin-3-yl) | H |
| ABR(Ia) or (Ib) | —NH-(1-methylpyrrolidin-3-yl) | NO₂ |
| ABS(Ia) or (Ib) | —NH-(1-methylpyrrolidin-3-yl) | CN |
| ABT(Ia) or (Ib) | —NH-(1-methylpyrrolidin-3-yl) | F |

TABLE 1-continued

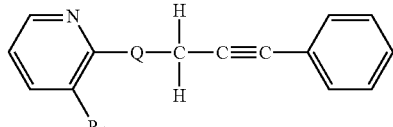

(Ia)

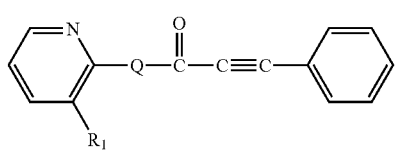

(Ib)

and pharmaceutically acceptable salts thereof, where

| Compound | Q | R₁ |
|---|---|---|
| ABU(Ia) or (Ib) | —NH-(1-methylpyrrolidin-3-yl) | Cl |
| ABV(Ia) or (Ib) | —NH-(1-methylpyrrolidin-3-yl) | CF₃ |
| ABW(Ia) or (Ib) | —NH-(1-methylpyrrolidin-3-yl) | CH₃ |
| ABX(Ia) or (Ib) | —NH-(1-methyl-2-oxopyrrolidin-4-yl) | H |
| ABY(Ia) or (Ib) | —NH-(1-methyl-2-oxopyrrolidin-4-yl) | NO₂ |
| ABZ(Ia) or (Ib) | —NH-(1-methyl-2-oxopyrrolidin-4-yl) | CN |
| ACA(Ia) or (Ib) | —NH-(1-methyl-2-oxopyrrolidin-4-yl) | F |
| ACB(Ia) or (Ib) | —NH-(1-methyl-2-oxopyrrolidin-4-yl) | Cl |
| ACC(Ia) or (Ib) | —NH-(1-methyl-2-oxopyrrolidin-4-yl) | CF₃ |
| ACD(Ia) or (Ib) | —NH-(1-methyl-2-oxopyrrolidin-4-yl) | CH₃ |

TABLE 1-continued

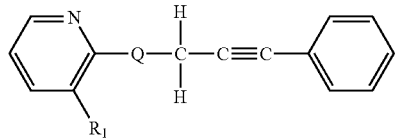

(Ia)

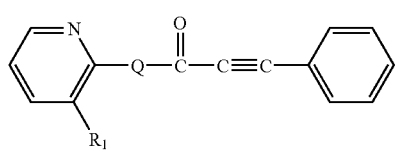

(Ib)

and pharmaceutically acceptable salts thereof, where

| Compound | Q | $R_1$ |
|---|---|---|
| ACE(Ia) or (Ib) | —NH— (3-amino-1-methyl-pyrrolidin-2-one) | H |
| ACF(Ia) or (Ib) | —NH— (3-amino-1-methyl-pyrrolidin-2-one) | $NO_2$ |
| ACG(Ia) or (Ib) | —NH— (3-amino-1-methyl-pyrrolidin-2-one) | CN |
| ACH(Ia) or (Ib) | —NH— (3-amino-1-methyl-pyrrolidin-2-one) | F |
| ACI(Ia) or (Ib) | —NH— (3-amino-1-methyl-pyrrolidin-2-one) | Cl |
| ACJ(Ia) or (Ib) | —NH— (3-amino-1-methyl-pyrrolidin-2-one) | $CF_3$ |
| ACK(Ia) or (Ib) | —NH— (3-amino-1-methyl-pyrrolidin-2-one) | $CH_3$ |
| ACL(Ia) or (Ib) | —NH— (3-amino-1-methyl-succinimide) | H |

TABLE 1-continued

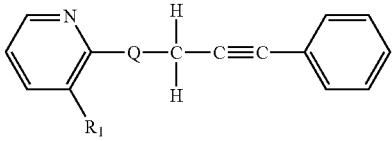

(Ia)

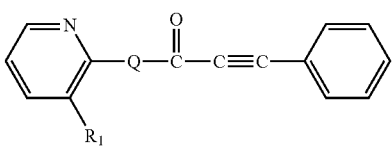

(Ib)

and pharmaceutically acceptable salts thereof, where

| Compound | Q | $R_1$ |
|---|---|---|
| ACM(Ia) or (Ib) | —NH— (3-amino-1-methyl-succinimide) | $NO_2$ |
| ACN(Ia) or (Ib) | —NH— (3-amino-1-methyl-succinimide) | CN |
| ACO(Ia) or (Ib) | —NH— (3-amino-1-methyl-succinimide) | F |
| ACP(Ia) or (Ib) | —NH— (3-amino-1-methyl-succinimide) | Cl |
| ACQ(Ia) or (Ib) | —NH— (3-amino-1-methyl-succinimide) | $CF_3$ |
| ACR(Ia) or (Ib) | —NH— (3-amino-1-methyl-succinimide) | $CH_3$ |
| ACS(Ia) or (Ib) | —NH— (4-amino-1,2-dimethyl-pyrrolidine) | H |
| ACT(Ia) or (Ib) | —NH— (4-amino-1,2-dimethyl-pyrrolidine) | $NO_2$ |

TABLE 1-continued

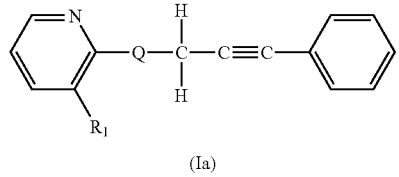

(Ia)

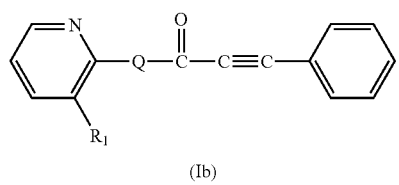

(Ib)

and pharmaceutically acceptable salts thereof, where

| Compound | Q | R₁ |
|---|---|---|
| ACU(Ia) or (Ib) | —NH—[2-methyl-1-methylpyrrolidin-4-yl] | CN |
| ACV(Ia) or (Ib) | —NH—[2-methyl-1-methylpyrrolidin-4-yl] | F |
| ACW(Ia) or (Ib) | —NH—[2-methyl-1-methylpyrrolidin-4-yl] | Cl |
| ACX(Ia) or (Ib) | —NH—[2-methyl-1-methylpyrrolidin-4-yl] | CF₃ |
| ACY(Ia) or (Ib) | —NH—[2-methyl-1-methylpyrrolidin-4-yl] | CH₃ |
| ACZ(Ia) or (Ib) | —NH—[2-methyl-1-methylpyrrolidin-3-yl] | H |
| ADA(Ia) or (Ib) | —NH—[2-methyl-1-methylpyrrolidin-3-yl] | NO₂ |
| ADB(Ia) or (Ib) | —NH—[2-methyl-1-methylpyrrolidin-3-yl] | CN |
| ADC(Ia) or (Ib) | —NH—[2-methyl-1-methylpyrrolidin-3-yl] | F |

TABLE 1-continued

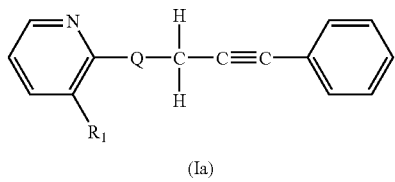

(Ia)

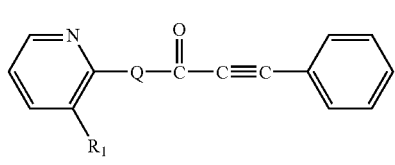

(Ib)

and pharmaceutically acceptable salts thereof, where

| Compound | Q | R₁ |
|---|---|---|
| ADD(Ia) or (Ib) | —NH—[2-methyl-1-methylpyrrolidin-3-yl] | Cl |
| ADE(Ia) or (Ib) | —NH—[2-methyl-1-methylpyrrolidin-3-yl] | CF₃ |
| ADF(Ia) or (Ib) | —NH—[2-methyl-1-methylpyrrolidin-3-yl] | CH₃ |
| ADG(Ia) or (Ib) | —NH—[2,5-dimethyl-1-methylpyrrolidin-3-yl] | H |
| ADH(Ia) or (Ib) | —NH—[2,5-dimethyl-1-methylpyrrolidin-3-yl] | NO₂ |
| ADI(Ia) or (Ib) | —NH—[2,5-dimethyl-1-methylpyrrolidin-3-yl] | CN |
| ADJ(Ia) or (Ib) | —NH—[2,5-dimethyl-1-methylpyrrolidin-3-yl] | F |

TABLE 1-continued

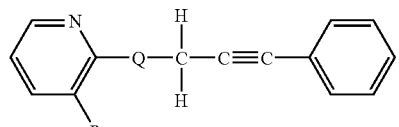

(Ia)

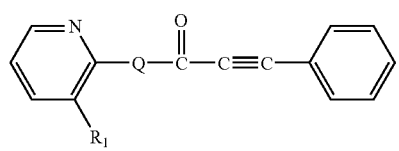

(Ib)

and pharmaceutically acceptable salts thereof, where

| Compound | Q | $R_1$ |
|---|---|---|
| ADK(Ia) or (Ib) | —NH— (pyrrolidine with N-CH3, 2-CH3, 5-CH3) | Cl |
| ADL(Ia) or (Ib) | —NH— (pyrrolidine with N-CH3, 2-CH3, 5-CH3) | $CF_3$ |
| ADM(Ia) or (Ib) | —NH— (pyrrolidine with N-CH3, 2-CH3, 5-CH3) | $CH_3$ |
| ADN(Ia) or (Ib) | —NH— (5-oxo-pyrrolidine with N-CH3, 2-CH3) | H |
| ADO(Ia) or (Ib) | —NH— (5-oxo-pyrrolidine with N-CH3, 2-CH3) | $NO_2$ |
| ADP(Ia) or (Ib) | —NH— (5-oxo-pyrrolidine with N-CH3, 2-CH3) | CN |
| ADQ(Ia) or (Ib) | —NH— (5-oxo-pyrrolidine with N-CH3, 2-CH3) | F |

TABLE 1-continued

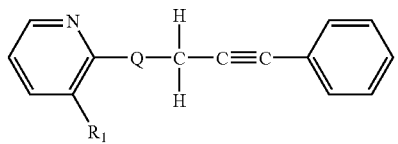

(Ia)

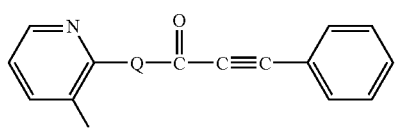

(Ib)

and pharmaceutically acceptable salts thereof, where

| Compound | Q | $R_1$ |
|---|---|---|
| ADR(Ia) or (Ib) | —NH— (5-oxo-pyrrolidine with N-CH3, 2-CH3) | Cl |
| ADS(Ia) or (Ib) | —NH— (5-oxo-pyrrolidine with N-CH3, 2-CH3) | $CF_3$ |
| ADT(Ia) or (Ib) | —NH— (5-oxo-pyrrolidine with N-CH3, 2-CH3) | $CH_3$ |
| ADU(Ia) or (Ib) | —NH— (5-oxo-pyrrolidine with N-CH3, 5-CH3) | H |
| ADV(Ia) or (Ib) | —NH— (5-oxo-pyrrolidine with N-CH3, 5-CH3) | $NO_2$ |
| ADW(Ia) or (Ib) | —NH— (5-oxo-pyrrolidine with N-CH3, 5-CH3) | CN |
| ADX(Ia) or (Ib) | —NH— (5-oxo-pyrrolidine with N-CH3, 5-CH3) | F |

TABLE 1-continued

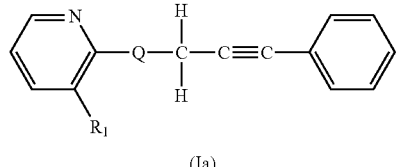

(Ia)

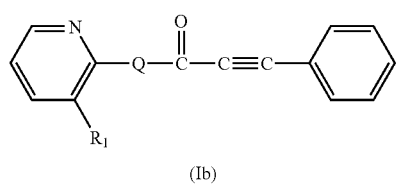

(Ib)

and pharmaceutically acceptable salts thereof, where

| Compound | Q | R₁ |
|---|---|---|
| ADY(Ia) or (Ib) | —NH— (3-amino-1,5-dimethylpyrrolidin-2-one) | Cl |
| ADZ(Ia) or (Ib) | —NH— (3-amino-1,5-dimethylpyrrolidin-2-one) | $CF_3$ |
| AEA(Ia) or (Ib) | —NH— (3-amino-1,5-dimethylpyrrolidin-2-one) | $CH_3$ |
| AEB(Ia) or (Ib) | —NH— (1-methylpiperidin-4-yl) | H |
| AEC(Ia) or (Ib) | —NH— (1-methylpiperidin-4-yl) | $NO_2$ |
| AED(Ia) or (Ib) | —NH— (1-methylpiperidin-4-yl) | CN |
| AEE(Ia) or (Ib) | —NH— (1-methylpiperidin-4-yl) | F |
| AEF(Ia) or (Ib) | —NH— (1-methylpiperidin-4-yl) | Cl |
| AEG(Ia) or (Ib) | —NH— (1-methylpiperidin-4-yl) | $CF_3$ |
| AEH(Ia) or (Ib) | —NH— (1-methylpiperidin-4-yl) | $CH_3$ |

TABLE 1-continued

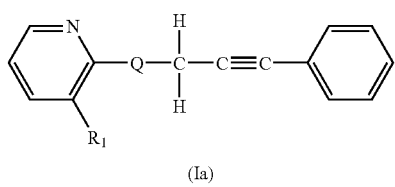

(Ia)

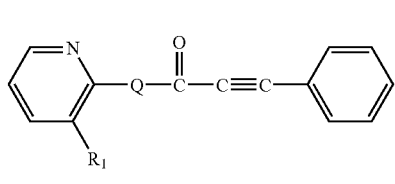

(Ib)

and pharmaceutically acceptable salts thereof, where

| Compound | Q | R₁ |
|---|---|---|
| AEI(Ia) or (Ib) | —NH— (1-methyl-2-oxopiperidin-4-yl) | H |
| AEJ(Ia) or (Ib) | —NH— (1-methyl-2-oxopiperidin-4-yl) | $NO_2$ |
| AEK(Ia) or (Ib) | —NH— (1-methyl-2-oxopiperidin-4-yl) | CN |
| AEL(Ia) or (Ib) | —NH— (1-methyl-2-oxopiperidin-4-yl) | F |
| AEM(Ia) or (Ib) | —NH— (1-methyl-2-oxopiperidin-4-yl) | Cl |
| AEN(Ia) or (Ib) | —NH— (1-methyl-2-oxopiperidin-4-yl) | $CF_3$ |
| AEO(Ia) or (Ib) | —NH— (1-methyl-2-oxopiperidin-4-yl) | $CH_3$ |

TABLE 1-continued

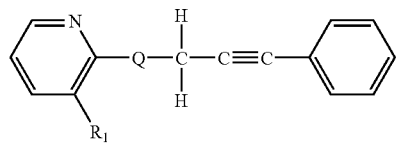

(Ia)

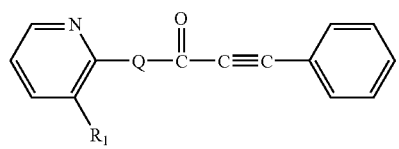

(Ib)

and pharmaceutically acceptable salts thereof, where

| Compound | Q | R₁ |
|---|---|---|
| AEP(Ia) or (Ib) | —NH— (4-amino-1-methylpiperidine-2,6-dione) | H |
| AEQ(Ia) or (Ib) | —NH— (4-amino-1-methylpiperidine-2,6-dione) | NO₂ |
| AER(Ia) or (Ib) | —NH— (4-amino-1-methylpiperidine-2,6-dione) | CN |
| AES(Ia) or (Ib) | —NH— (4-amino-1-methylpiperidine-2,6-dione) | F |
| AET(Ia) or (Ib) | —NH— (4-amino-1-methylpiperidine-2,6-dione) | Cl |
| AEU(Ia) or (Ib) | —NH— (4-amino-1-methylpiperidine-2,6-dione) | CF₃ |

TABLE 1-continued

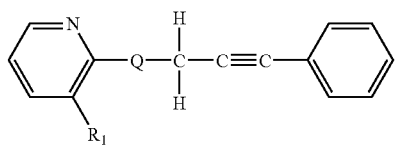

(Ia)

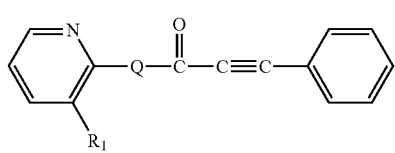

(Ib)

and pharmaceutically acceptable salts thereof, where

| Compound | Q | R₁ |
|---|---|---|
| AEV(Ia) or (Ib) | —NH— (4-amino-1-methylpiperidine-2,6-dione) | CH₃ |
| AEW(Ia) or (Ib) | —NH— (4-amino-1,2-dimethylpiperidine) | H |
| AEX(Ia) or (Ib) | —NH— (4-amino-1,2-dimethylpiperidine) | NO₂ |
| AEY(Ia) or (Ib) | —NH— (4-amino-1,2-dimethylpiperidine) | CN |
| AEZ(Ia) or (Ib) | —NH— (4-amino-1,2-dimethylpiperidine) | F |
| AFA(Ia) or (Ib) | —NH— (4-amino-1,2-dimethylpiperidine) | Cl |
| AFB(Ia) or (Ib) | —NH— (4-amino-1,2-dimethylpiperidine) | CF₃ |

TABLE 1-continued

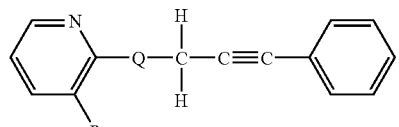

(Ia)

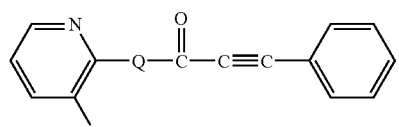

(Ib)

and pharmaceutically acceptable salts thereof, where

| Compound | Q | R₁ |
|---|---|---|
| AFC(Ia) or (Ib) | —NH—[2,6-dimethylpiperidin-4-yl, N-methyl] | CH₃ |
| AFD(Ia) or (Ib) | —NH—[2,6-dimethylpiperidin-4-yl, N-methyl] | H |
| AFE(Ia) or (Ib) | —NH—[2,6-dimethylpiperidin-4-yl, N-methyl] | NO₂ |
| AFF(Ia) or (Ib) | —NH—[2,6-dimethylpiperidin-4-yl, N-methyl] | CN |
| AFG(Ia) or (Ib) | —NH—[2,6-dimethylpiperidin-4-yl, N-methyl] | F |
| AFH(Ia) or (Ib) | —NH—[2,6-dimethylpiperidin-4-yl, N-methyl] | Cl |

TABLE 1-continued

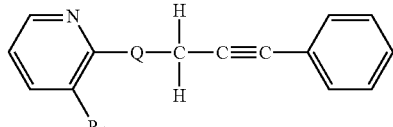

(Ia)

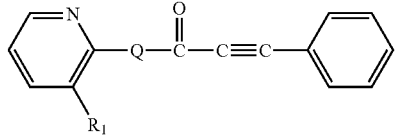

(Ib)

and pharmaceutically acceptable salts thereof, where

| Compound | Q | R₁ |
|---|---|---|
| AFI(Ia) or (Ib) | —NH—[2,6-dimethylpiperidin-4-yl, N-methyl] | CF₃ |
| AFJ(Ia) or (Ib) | —NH—[2,6-dimethylpiperidin-4-yl, N-methyl] | CH₃ |
| AFK(Ia) or (Ib) | —NH—[6-methyl-2-oxopiperidin-4-yl, N-methyl] | H |
| AFL(Ia) or (Ib) | —NH—[6-methyl-2-oxopiperidin-4-yl, N-methyl] | NO₂ |
| AFM(Ia) or (Ib) | —NH—[6-methyl-2-oxopiperidin-4-yl, N-methyl] | CN |
| AFN(Ia) or (Ib) | —NH—[6-methyl-2-oxopiperidin-4-yl, N-methyl] | F |

TABLE 1-continued

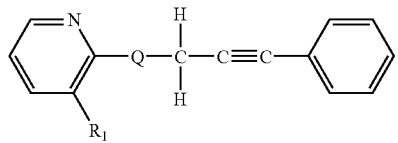

(Ia)

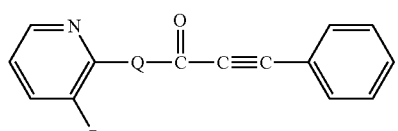

(Ib)

and pharmaceutically acceptable salts thereof, where

| Compound | Q | R₁ |
|---|---|---|
| AFO(Ia) or (Ib) | —NH–(4-amino-1,6-dimethyl-2-oxopiperidinyl) | Cl |
| AFP(Ia) or (Ib) | —NH–(4-amino-1,6-dimethyl-2-oxopiperidinyl) | CF₃ |
| AFQ(Ia) or (Ib) | —NH–(4-amino-1,6-dimethyl-2-oxopiperidinyl) | CH₃ |
| AFR(Ia) or (Ib) | —NH–(1-methylazepan-4-yl) | H |
| AFS(Ia) or (Ib) | —NH–(1-methylazepan-4-yl) | NO₂ |
| AFT(Ia) or (Ib) | —NH–(1-methylazepan-4-yl) | CN |
| AFU(Ia) or (Ib) | —NH–(1-methylazepan-4-yl) | F |

TABLE 1-continued

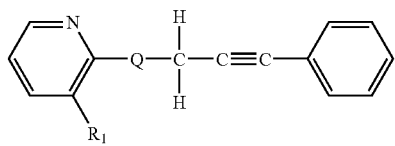

(Ia)

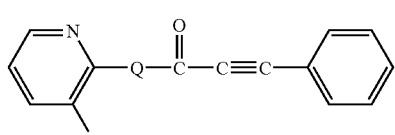

(Ib)

and pharmaceutically acceptable salts thereof, where

| Compound | Q | R₁ |
|---|---|---|
| AFV(Ia) or (Ib) | —NH–(1-methylazepan-4-yl) | Cl |
| AFW(Ia) or (Ib) | —NH–(1-methylazepan-4-yl) | CF₃ |
| AFX(Ia) or (Ib) | —NH–(1-methylazepan-4-yl) | CH₃ |
| AFY(Ia) or (Ib) | —NH–(1-methyl-2-oxoazepan-4-yl) | H |
| AFZ(Ia) or (Ib) | —NH–(1-methyl-2-oxoazepan-4-yl) | NO₂ |
| AGA(Ia) or (Ib) | —NH–(1-methyl-2-oxoazepan-4-yl) | CN |
| AGB(Ia) or (Ib) | —NH–(1-methyl-2-oxoazepan-4-yl) | F |

TABLE 1-continued

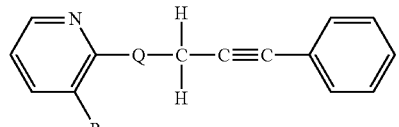

(Ia)

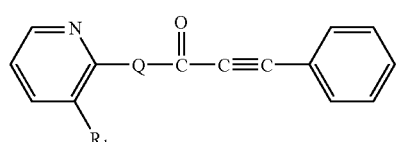

(Ib)

and pharmaceutically acceptable salts thereof, where

| Compound | Q | R₁ |
|---|---|---|
| AGC(Ia) or (Ib) | —NH—(4-amino-1-methylazepan-2-one) | Cl |
| AGD(Ia) or (Ib) | —NH—(4-amino-1-methylazepan-2-one) | CF₃ |
| AGE(Ia) or (Ib) | —NH—(4-amino-1-methylazepan-2-one) | CH₃ |
| AGF(Ia) or (Ib) | —NH—(4-amino-1-methylazepan-2-one) | H |
| AGG(Ia) or (Ib) | —NH—(4-amino-1-methylazepan-2-one) | NO₂ |
| AGH(Ia) or (Ib) | —NH—(4-amino-1-methylazepan-2-one) | CN |
| AGI(Ia) or (Ib) | —NH—(4-amino-1-methylazepan-2-one) | F |
| AGJ(Ia) or (Ib) | —NH—(4-amino-1-methylazepan-2-one) | Cl |

TABLE 1-continued

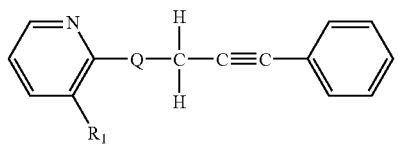

(Ia)

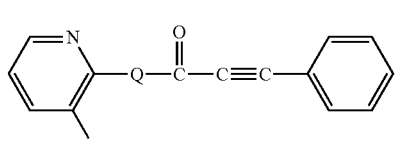

(Ib)

and pharmaceutically acceptable salts thereof, where

| Compound | Q | R₁ |
|---|---|---|
| AGK(Ia) or (Ib) | —NH—(5-amino-1-methylazepan-2-one) | CF₃ |
| AGL(Ia) or (Ib) | —NH—(5-amino-1-methylazepan-2-one) | CH₃ |
| AGM(Ia) or (Ib) | —NH—(4-amino-1-methylazepane-2,7-dione) | H |
| AGN(Ia) or (Ib) | —NH—(4-amino-1-methylazepane-2,7-dione) | NO₂ |
| AGO(Ia) or (Ib) | —NH—(4-amino-1-methylazepane-2,7-dione) | CN |
| AGP(Ia) or (Ib) | —NH—(4-amino-1-methylazepane-2,7-dione) | F |
| AGQ(Ia) or (Ib) | —NH—(4-amino-1-methylazepane-2,7-dione) | Cl |

TABLE 1-continued

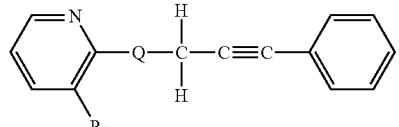

(Ia)

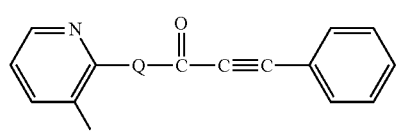

(Ib)

and pharmaceutically acceptable salts thereof, where

| Compound | Q | $R_1$ |
|---|---|---|
| AGR(Ia) or (Ib) | 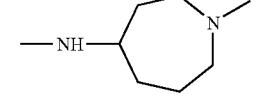 | $CF_3$ |
| AGS(Ia) or (Ib) | 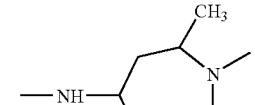 | $CH_3$ |
| AGT(Ia) or (Ib) | 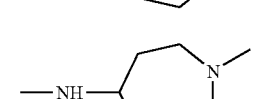 | H |
| AGU(Ia) or (Ib) |  | $NO_2$ |
| AGV(Ia) or (Ib) |  | CN |
| AGW(Ia) or (Ib) | 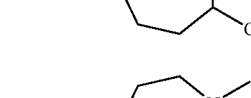 | F |
| AGX(Ia) or (Ib) |  | Cl |

TABLE 1-continued

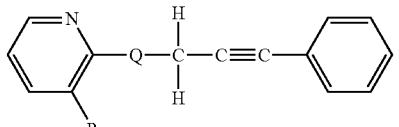

(Ia)

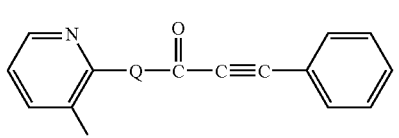

(Ib)

and pharmaceutically acceptable salts thereof, where

| Compound | Q | $R_1$ |
|---|---|---|
| AGY(Ia) or (Ib) | 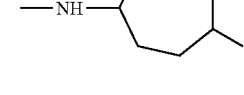 | $CF_3$ |
| AGZ(Ia) or (Ib) | | $CH_3$ |
| AHA(Ia) or (Ib) | | H |
| AHB(Ia) or (Ib) | | $NO_2$ |
| AHC(Ia) or (Ib) | | CN |
| AHD(Ia) or (Ib) | | F |
| AHE(Ia) or (Ib) | | Cl |
| AHF(Ia) or (Ib) | | $CF_3$ |

TABLE 1-continued

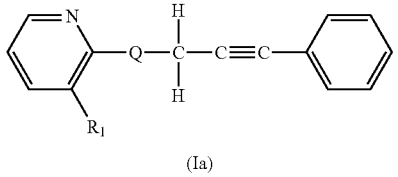

(Ia)

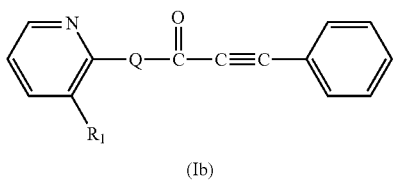

(Ib)

and pharmaceutically acceptable salts thereof, where

| Compound | Q | R₁ |
|---|---|---|
| AHG(Ia) or (Ib) | -NH-(4-amino-1,2-dimethylazepane) | CH₃ |
| AHH(Ia) or (Ib) | -NH-(4-amino-1,2,7-trimethylazepane...) | H |
| AHI(Ia) or (Ib) | -NH-(4-amino-1,2,7-trimethylazepane) | NO₂ |
| AHJ(Ia) or (Ib) | -NH-(4-amino-1,2,7-trimethylazepane) | CN |
| AHX(Ia) or (Ib) | -NH-(4-amino-1,2,7-trimethylazepane) | F |
| AHL(Ia) or (Ib) | -NH-(4-amino-1,2,7-trimethylazepane) | Cl |
| AHM(Ia) or (Ib) | -NH-(4-amino-1,2,7-trimethylazepane) | CF₃ |

TABLE 1-continued

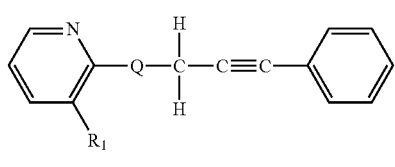

(Ia)

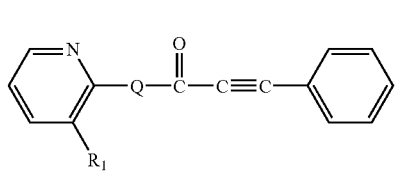

(Ib)

and pharmaceutically acceptable salts thereof, where

| Compound | Q | R₁ |
|---|---|---|
| AHN(Ia) or (Ib) | -NH-(4-amino-1,2,7-trimethylazepane) | CH₃ |
| AHO(Ia) or (Ib) | -NH-(4-amino-1-methyl-7-methyl-2-oxoazepane) | H |
| AHP(Ia) or (Ib) | -NH-(4-amino-1-methyl-7-methyl-2-oxoazepane) | NO₂ |
| AHQ(Ia) or (Ib) | -NH-(4-amino-1-methyl-7-methyl-2-oxoazepane) | CN |
| AHR(Ia) or (Ib) | -NH-(4-amino-1-methyl-7-methyl-2-oxoazepane) | F |
| AHS(Ia) or (Ib) | -NH-(4-amino-1-methyl-7-methyl-2-oxoazepane) | Cl |

TABLE 1-continued

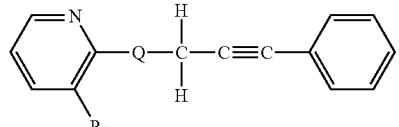

(Ia)

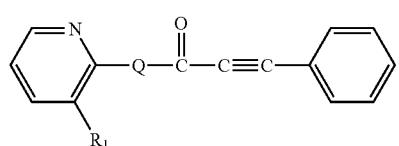

(Ib)

and pharmaceutically acceptable salts thereof, where

| Compound | Q | R₁ |
|---|---|---|
| AHT(Ia) or (Ib) | (4-NH, 7-methyl, 1-methyl-azepan-2-one) | CF₃ |
| AHU(Ia) or (Ib) | (4-NH, 7-methyl, 1-methyl-azepan-2-one) | CH₃ |
| AHV(Ia) or (Ib) | (4-NH, 7-methyl, 1-methyl-azepan-2-one) | H |
| AHW(Ia) or (Ib) | (4-NH, 7-methyl, 1-methyl-azepan-2-one) | NO₂ |
| AHX(Ia) or (Ib) | (4-NH, 7-methyl, 1-methyl-azepan-2-one) | CN |
| AHY(Ia) or (Ib) | (4-NH, 7-methyl, 1-methyl-azepan-2-one) | F |
| AHZ(Ia) or (Ib) | (4-NH, 7-methyl, 1-methyl-azepan-2-one) | Cl |

TABLE 1-continued

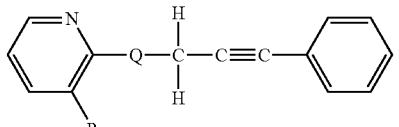

(Ia)

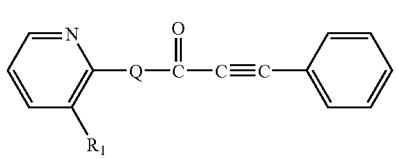

(Ib)

and pharmaceutically acceptable salts thereof, where

| Compound | Q | R₁ |
|---|---|---|
| AIA(Ia) or (Ib) | (7-methyl, 1-methyl-azepan-2-one-4-NH) | CF₃ |
| AIB(Ia) or (Ib) | (7-methyl, 1-methyl-azepan-2-one-4-NH) | CH₃ |
| AIC(Ia) or (Ib) | (1-methyl-azocan-4-yl-NH) | H |
| AID(Ia) or (Ib) | (1-methyl-azocan-4-yl-NH) | NO₂ |
| AIE(Ia) or (Ib) | (1-methyl-azocan-4-yl-NH) | CN |
| AIF(Ia) or (Ib) | (1-methyl-azocan-4-yl-NH) | F |
| AIG(Ia) or (Ib) | (1-methyl-azocan-4-yl-NH) | Cl |
| AIH(Ia) or (Ib) | (1-methyl-azocan-4-yl-NH) | CF₃ |

TABLE 1-continued

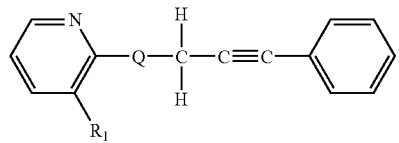

(Ia)

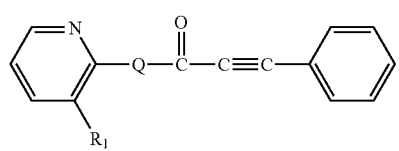

(Ib)

and pharmaceutically acceptable salts thereof, where

| Compound | Q | R₁ |
|---|---|---|
| AII(Ia) or (Ib) | —NH—[4-amino-1-methylazocane] | CH₃ |
| AIJ(Ia) or (Ib) | —NH—[4-amino-1-methyl-azocan-2-one] | H |
| AIK(Ia) or (Ib) | —NH—[4-amino-1-methyl-azocan-2-one] | NO₂ |
| AIL(Ia) or (Ib) | —NH—[4-amino-1-methyl-azocan-2-one] | CN |
| AIM(Ia) or (Ib) | —NH—[4-amino-1-methyl-azocan-2-one] | F |
| AIN(Ia) or (Ib) | —NH—[4-amino-1-methyl-azocan-2-one] | Cl |
| AIO(Ia) or (Ib) | —NH—[4-amino-1-methyl-azocan-2-one] | CF₃ |

TABLE 1-continued

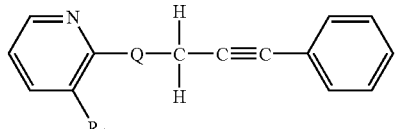

(Ia)

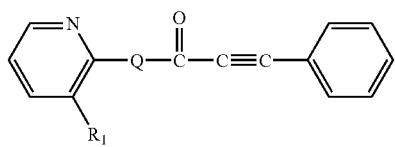

(Ib)

and pharmaceutically acceptable salts thereof, where

| Compound | Q | R₁ |
|---|---|---|
| AIP(Ia) or (Ib) | —NH—[4-amino-1-methyl-azocan-2-one] | CH₃ |
| AIQ(Ia) or (Ib) | —NH—[4-amino-1-methyl-azocane-2,8-dione] | H |
| AIR(Ia) or (Ib) | —NH—[4-amino-1-methyl-azocane-2,8-dione] | NO₂ |
| AIS(Ia) or (Ib) | —NH—[4-amino-1-methyl-azocane-2,8-dione] | CN |
| AIT(Ia) or (Ib) | —NH—[4-amino-1-methyl-azocane-2,8-dione] | F |
| AIU(Ia) or (Ib) | —NH—[4-amino-1-methyl-azocane-2,8-dione] | Cl |

TABLE 1-continued

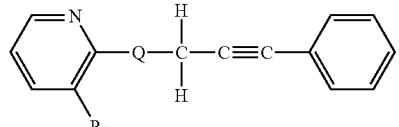

(Ia)

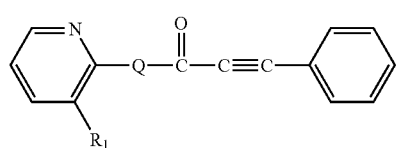

(Ib)

and pharmaceutically acceptable salts thereof, where

| Compound | Q | R₁ |
|---|---|---|
| AIV(Ia) or (Ib) | —NH— [azepane-2,7-dione, N-methyl] | CF₃ |
| AIW(Ia) or (Ib) | —NH— [azepane-2,7-dione, N-methyl] | CH₃ |
| AIX(Ia) or (Ib) | —NH— [azepane, 2-CH₃, N-methyl] | H |
| AIY(Ia) or (Ib) | —NH— [azepane, 2-CH₃, N-methyl] | NO₂ |
| AIZ(Ia) or (Ib) | —NH— [azepane, 2-CH₃, N-methyl] | CN |
| AJA(Ia) or (Ib) | —NH— [azepane, 2-CH₃, N-methyl] | F |
| AJB(Ia) or (Ib) | —NH— [azepane, 2-CH₃, N-methyl] | Cl |

TABLE 1-continued

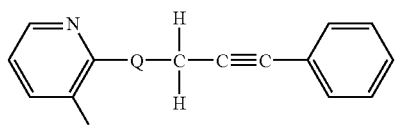

(Ia)

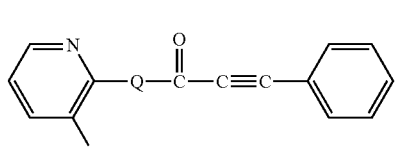

(Ib)

and pharmaceutically acceptable salts thereof, where

| Compound | Q | R₁ |
|---|---|---|
| AJC(Ia) or (Ib) | —NH— [azocane, 2-CH₃, N-methyl] | CF₃ |
| AJD(Ia) or (Ib) | —NH— [azocane, 2-CH₃, N-methyl] | CH₃ |
| AJE(Ia) or (Ib) | —NH— [azocane, 2-CH₃, 8-CH₃, N-methyl] | H |
| AJF(Ia) or (Ib) | —NH— [azocane, 2-CH₃, 8-CH₃, N-methyl] | NO₂ |
| AJG(Ia) or (Ib) | —NH— [azocane, 2-CH₃, 8-CH₃, N-methyl] | CN |
| AJH(Ia) or (Ib) | —NH— [azocane, 2-CH₃, 8-CH₃, N-methyl] | F |

TABLE 1-continued
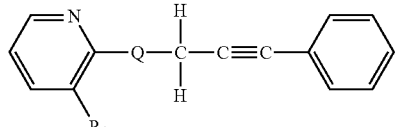
(Ia)
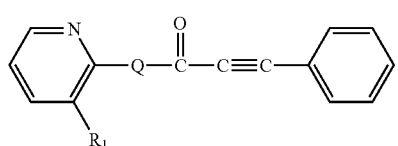
(Ib)
and pharmaceutically acceptable salts thereof, where
| Compound | Q | R₁ |
|---|---|---|
| AJI(Ia) or (Ib) |  | Cl |
| AJJ(Ia) or (Ib) | 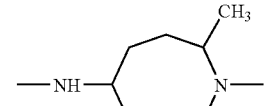 | CF₃ |
| AJK(Ia) or (Ib) |  | CH₃ |
| AJL(Ia) or (Ib) | 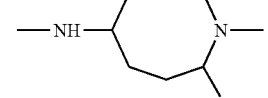 | H |
| AJM(Ia) or (Ib) |  | NO₂ |
| AJN(Ia) or (Ib) |  | CN |
| AJO(Ia) or (Ib) | 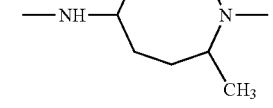 | F |
| AJP(Ia) or (Ib) | 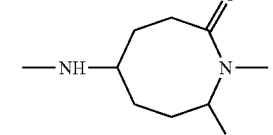 | Cl |
| AJQ(Ia) or (Ib) | 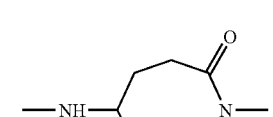 | CF₃ |
| AJR(Ia) or (Ib) | 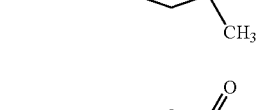 | CH₃ |
| AJS(Ia) or (Ib) | 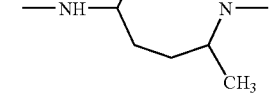 | H |
| AJT(Ia) or (Ib) | 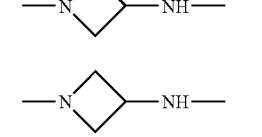 | NO₂ |
| AJU(Ia) or (Ib) |  | CN |
| AJV(Ia) or (Ib) |  | F |
TABLE 1-continued
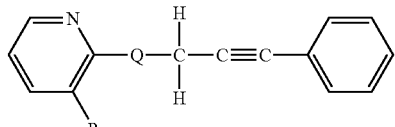
(Ia)
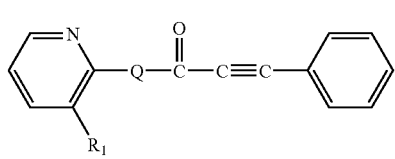
(Ib)

TABLE 1-continued

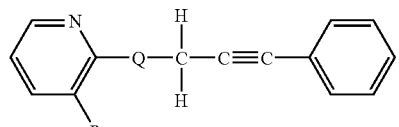

(Ia)

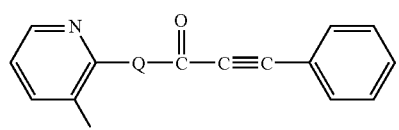

(Ib)

and pharmaceutically acceptable salts thereof, where

| Compound | Q | R₁ |
|---|---|---|
| AJW(Ia) or (Ib) | —N⟨azetidine⟩NH— | Cl |
| AJX(Ia) or (Ib) | —N⟨azetidine⟩NH— | CF₃ |
| AJY(Ia) or (Ib) | —N⟨azetidine⟩NH— | CH₃ |
| AJZ(Ia) or (Ib) | —N⟨2-CH₃-azetidine⟩NH— | H |
| AKA(Ia) or (Ib) | —N⟨2-CH₃-azetidine⟩NH— | NO₂ |
| AKB(Ia) or (Ib) | —N⟨2-CH₃-azetidine⟩NH— | CN |
| AKC(Ia) or (Ib) | —N⟨2-CH₃-azetidine⟩NH— | F |
| AKD(Ia) or (Ib) | —N⟨2-CH₃-azetidine⟩NH— | Cl |
| AKE(Ia) or (Ib) | —N⟨2-CH₃-azetidine⟩NH— | CF₃ |

TABLE 1-continued

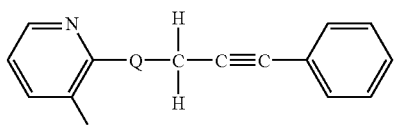

(Ia)

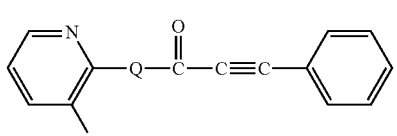

(Ib)

and pharmaceutically acceptable salts thereof, where

| Compound | Q | R₁ |
|---|---|---|
| AKF(Ia) or (Ib) | —N⟨2-CH₃-azetidine⟩NH— | CH₃ |
| AKG(Ia) or (Ib) | —N⟨2,4-diCH₃-azetidine⟩NH— | H |
| AKI(Ia) or (Ib) | —N⟨2,4-diCH₃-azetidine⟩NH— | NO₂ |
| AKI(Ia) or (Ib) | —N⟨2,4-diCH₃-azetidine⟩NH— | CN |
| AKJ(Ia) or (Ib) | —N⟨2,4-diCH₃-azetidine⟩NH— | F |
| AKK(Ia) or (Ib) | —N⟨2,4-diCH₃-azetidine⟩NH— | Cl |

TABLE 1-continued

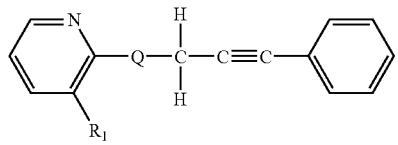

(Ia)

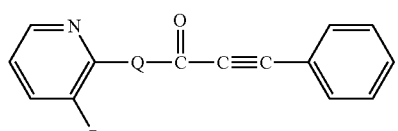

(Ib)

and pharmaceutically acceptable salts thereof, where

| Compound | Q | R₁ |
|---|---|---|
| AKL(Ia) or (Ib) | ![azetidine with 2,4-diCH3 and 3-NH] | CF₃ |
| AKM(Ia) or (Ib) | ![azetidine with 2,4-diCH3 and 3-NH] | CH₃ |
| AKN(Ia) or (Ib) | ![3-NH-azetidin-2-one] | H |
| AKO(Ia) or (Ib) | ![3-NH-azetidin-2-one] | NO₂ |
| AKP(Ia) or (Ib) | ![3-NH-azetidin-2-one] | CN |
| AKQ(Ia) or (Ib) | ![3-NH-azetidin-2-one] | F |
| AKR(Ia) or (Ib) | ![3-NH-azetidin-2-one] | Cl |

TABLE 1-continued

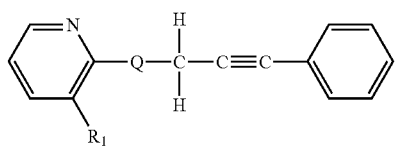

(Ia)

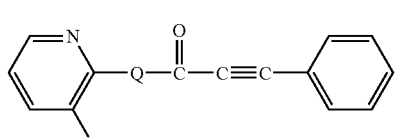

(Ib)

and pharmaceutically acceptable salts thereof, where

| Compound | Q | R₁ |
|---|---|---|
| AKS(Ia) or (Ib) | 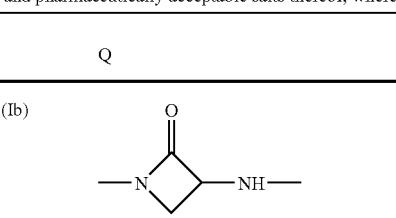 | CF₃ |
| AKT(Ia) or (Ib) | 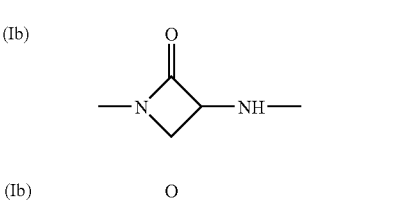 | CH₃ |
| AKU(Ia) or (Ib) | 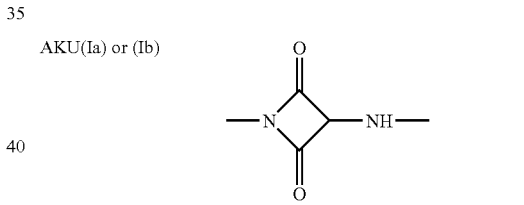 | H |
| AKV(Ia) or (Ib) | 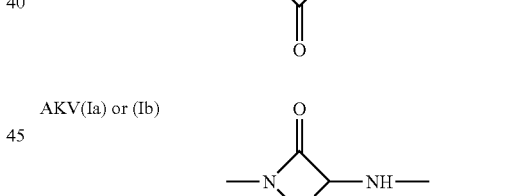 | NO₂ |
| AKW(Ia) or (Ib) | 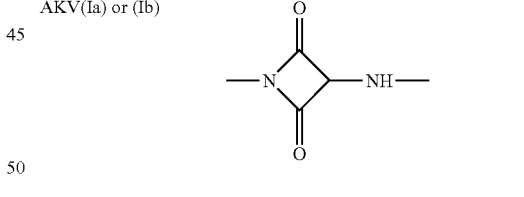 | CN |
| AKX(Ia) or (Ib) | 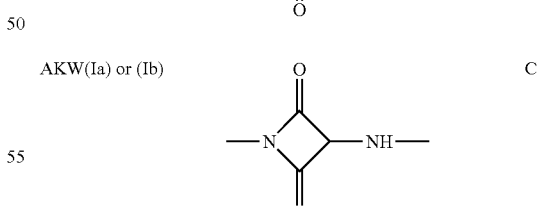 | F |

TABLE 1-continued

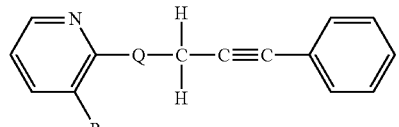

(Ia)

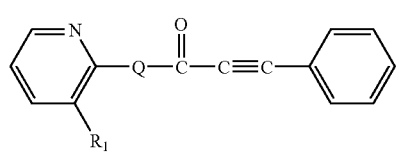

(Ib)

and pharmaceutically acceptable salts thereof, where

| Compound | Q | R₁ |
|---|---|---|
| AKY(Ia) or (Ib) | azetidine-2,4-dione (N-methyl, 3-NH-) | Cl |
| AKZ(Ia) or (Ib) | azetidine-2,4-dione (N-methyl, 3-NH-) | CF₃ |
| ALA(Ia) or (Ib) | azetidine-2,4-dione (N-methyl, 3-NH-) | CH₃ |
| ALB(Ia) or (Ib) | 4-methylazetidin-2-one (N-methyl, 3-NH-) | H |
| ALC(Ia) or (Ib) | 4-methylazetidin-2-one (N-methyl, 3-NH-) | NO₂ |
| ALD(Ia) or (Ib) | 4-methylazetidin-2-one (N-methyl, 3-NH-) | CN |

TABLE 1-continued

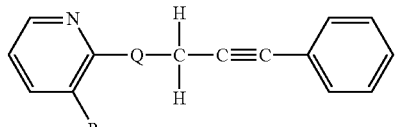

(Ia)

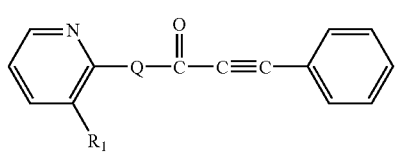

(Ib)

and pharmaceutically acceptable salts thereof, where

| Compound | Q | R₁ |
|---|---|---|
| ALE(Ia) or (Ib) | 4-methylazetidin-2-one (N-methyl, 3-NH-) | F |
| ALF(Ia) or (Ib) | 4-methylazetidin-2-one (N-methyl, 3-NH-) | Cl |
| ALG(Ia) or (Ib) | 4-methylazetidin-2-one (N-methyl, 3-NH-) | CF₃ |
| ALH(Ia) or (Ib) | 4-methylazetidin-2-one (N-methyl, 3-NH-) | CH₃ |
| ALI(Ia) or (Ib) | pyrrolidine (N-methyl, 3-NH-) | H |
| ALJ(Ia) or (Ib) | pyrrolidine (N-methyl, 3-NH-) | NO₂ |
| ALK(Ia) or (Ib) | pyrrolidine (N-methyl, 3-NH-) | CN |

TABLE 1-continued

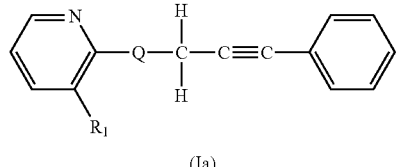

(Ia)

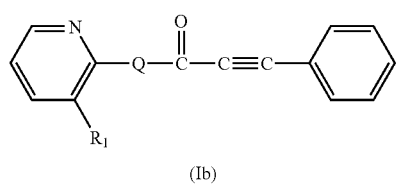

(Ib)

and pharmaceutically acceptable salts thereof, where

| Compound | Q | R$_1$ |
|---|---|---|
| ALL(Ia) or (Ib) | ![pyrrolidine-NH] | F |
| ALM(Ia) or (Ib) | ![pyrrolidine-NH] | Cl |
| ALN(Ia) or (Ib) | ![pyrrolidine-NH] | CF$_3$ |
| ALO(Ia) or (Ib) | ![pyrrolidine-NH] | CH$_3$ |
| ALP(Ia) or (Ib) | ![pyrrolidinone-NH] | H |
| ALQ(Ia) or (Ib) | ![pyrrolidinone-NH] | NO$_2$ |
| ALR(Ia) or (Ib) | ![pyrrolidinone-NH] | CN |
| ALS(Ia) or (Ib) | ![pyrrolidinone-NH] | F |

TABLE 1-continued

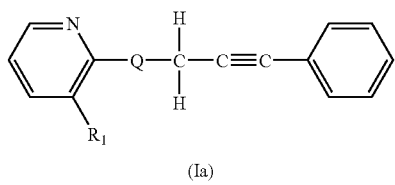

(Ia)

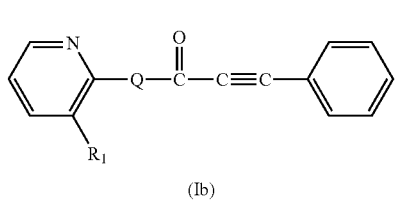

(Ib)

and pharmaceutically acceptable salts thereof, where

| Compound | Q | R$_1$ |
|---|---|---|
| ALT(Ia) or (Ib) | ![pyrrolidinone-NH] | Cl |
| ALU(Ia) or (Ib) | ![pyrrolidinone-NH] | CF$_3$ |
| ALV(Ia) or (Ib) | ![pyrrolidinone-NH] | CH$_3$ |
| ALW(Ia) or (Ib) | ![pyrrolidinone-NH] | H |
| ALX(Ia) or (Ib) | ![pyrrolidinone-NH] | NO$_2$ |
| ALY(Ia) or (Ib) | ![pyrrolidinone-NH] | CN |
| ALZ(Ia) or (Ib) | ![pyrrolidinone-NH] | F |

TABLE 1-continued

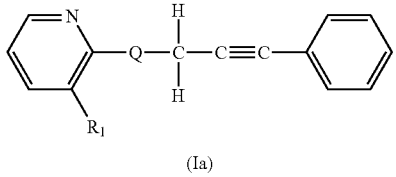

(Ia)

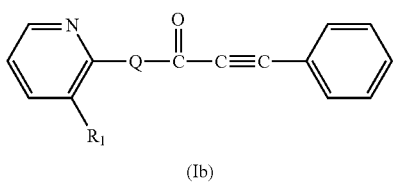

(Ib)

and pharmaceutically acceptable salts thereof, where

| Compound | Q | R₁ |
|---|---|---|
| AMA(Ia) or (Ib) | ![pyrrolidinone-NH] | Cl |
| AMB(Ia) or (Ib) | ![pyrrolidinone-NH] | CF₃ |
| AMC(Ia) or (Ib) | ![pyrrolidinone-NH] | CH₃ |
| AMD(Ia) or (Ib) | ![succinimide-NH] | H |
| AME(Ia) or (Ib) | ![succinimide-NH] | NO₂ |
| AMF(Ia) or (Ib) | ![succinimide-NH] | CN |
| AMG(Ia) or (Ib) | ![succinimide-NH] | F |

TABLE 1-continued

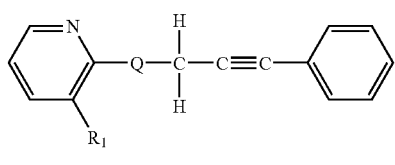

(Ia)

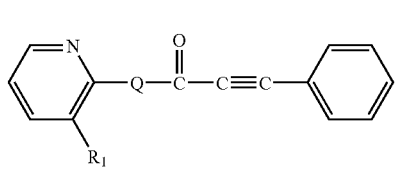

(Ib)

and pharmaceutically acceptable salts thereof, where

| Compound | Q | R₁ |
|---|---|---|
| AMH(Ia) or (Ib) | ![succinimide-NH] | Cl |
| AMI(Ia) or (Ib) | ![succinimide-NH] | CF₃ |
| AMJ(Ia) or (Ib) | ![succinimide-NH] | CH₃ |
| AMK(Ia) or (Ib) | ![methylpyrrolidine-NH] | H |
| AML(Ia) or (Ib) | ![methylpyrrolidine-NH] | NO₂ |
| AMM(Ia) or (Ib) | ![methylpyrrolidine-NH] | CN |

TABLE 1-continued

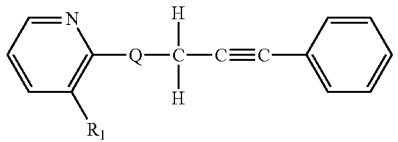

(Ia)

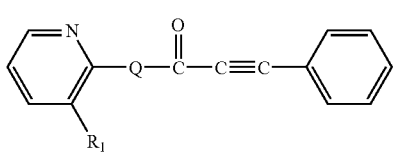

(Ib)

and pharmaceutically acceptable salts thereof, where

| Compound | Q | R₁ |
|---|---|---|
| AMN(Ia) or (Ib) | 2-methyl-4-(methylamino)pyrrolidin-1-yl | F |
| AMO(Ia) or (Ib) | 2-methyl-4-(methylamino)pyrrolidin-1-yl | Cl |
| AMP(Ia) or (Ib) | 2-methyl-4-(methylamino)pyrrolidin-1-yl | CF₃ |
| AMQ(Ia) or (Ib) | 2-methyl-4-(methylamino)pyrrolidin-1-yl | CH₃ |
| AMR(Ia) or (Ib) | 2-methyl-3-(methylamino)pyrrolidin-1-yl | H |
| AMS(Ia) or (Ib) | 2-methyl-3-(methylamino)pyrrolidin-1-yl | NO₂ |
| AMT(Ia) or (Ib) | 2-methyl-3-(methylamino)pyrrolidin-1-yl | CN |

TABLE 1-continued

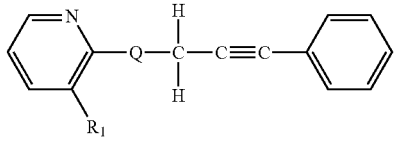

(Ia)

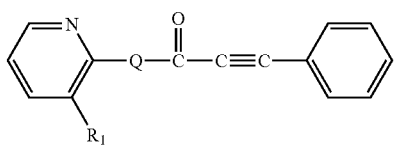

(Ib)

and pharmaceutically acceptable salts thereof, where

| Compound | Q | R₁ |
|---|---|---|
| AMU(Ia) or (Ib) | 2-methyl-3-(methylamino)pyrrolidin-1-yl | F |
| AMV(Ia) or (Ib) | 2-methyl-3-(methylamino)pyrrolidin-1-yl | Cl |
| AMW(Ia) or (Ib) | 2-methyl-3-(methylamino)pyrrolidin-1-yl | CF₃ |
| AMX(Ia) or (Ib) | 2-methyl-3-(methylamino)pyrrolidin-1-yl | CH₃ |
| AMY(Ia) or (Ib) | 2,5-dimethyl-3-(methylamino)pyrrolidin-1-yl | H |
| AMZ(Ia) or (Ib) | 2,5-dimethyl-3-(methylamino)pyrrolidin-1-yl | NO₂ |
| ANA(Ia) or (Ib) | 2,5-dimethyl-3-(methylamino)pyrrolidin-1-yl | CN |

TABLE 1-continued

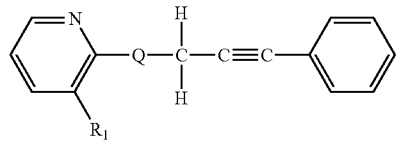

(Ia)

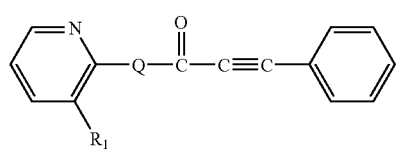

(Ib)

and pharmaceutically acceptable salts thereof, where

| Compound | Q | R₁ |
|---|---|---|
| ANB(Ia) or (Ib) | H₃C, H₃C-substituted N-methylpyrrolidinyl with NH | F |
| ANC(Ia) or (Ib) | H₃C, H₃C-substituted N-methylpyrrolidinyl with NH | Cl |
| AND(Ia) or (Ib) | H₃C, H₃C-substituted N-methylpyrrolidinyl with NH | CF₃ |
| ANE(Ia) or (Ib) | H₃C, H₃C-substituted N-methylpyrrolidinyl with NH | CH₃ |
| ANF(Ia) or (Ib) | H₃C-substituted N-pyrrolidinone with NH | H |
| ANG(Ia) or (Ib) | H₃C-substituted N-pyrrolidinone with NH | NO₂ |

TABLE 1-continued

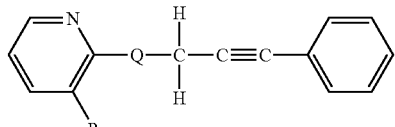

(Ia)

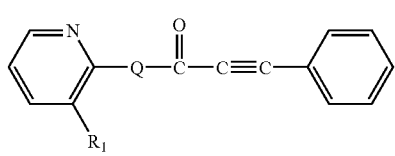

(Ib)

and pharmaceutically acceptable salts thereof, where

| Compound | Q | R₁ |
|---|---|---|
| ANH(Ia) or (Ib) | H₃C-substituted N-pyrrolidinone with NH | CN |
| ANI(Ia) or (Ib) | H₃C-substituted N-pyrrolidinone with NH | F |
| ANJ(Ia) or (Ib) | H₃C-substituted N-pyrrolidinone with NH | Cl |
| ANK(Ia) or (Ib) | H₃C-substituted N-pyrrolidinone with NH | CF₃ |
| ANL(Ia) or (Ib) | H₃C-substituted N-pyrrolidinone with NH | CH₃ |
| ANM(Ia) or (Ib) | H₃C-substituted N-pyrrolidinone with NH (alternate regiochemistry) | H |

TABLE 1-continued

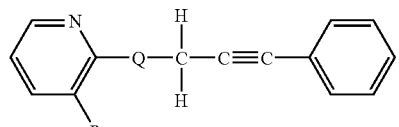

(Ia)

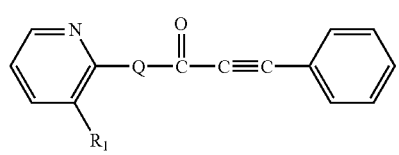

(Ib)

and pharmaceutically acceptable salts thereof, where

| Compound | Q | R₁ |
|---|---|---|
| ANN(Ia) or (Ib) | H₃C—[pyrrolidinone with NH] | NO₂ |
| ANO(Ia) or (Ib) | H₃C—[pyrrolidinone with NH] | CN |
| ANP(Ia) or (Ib) | H₃C—[pyrrolidinone with NH] | F |
| ANQ(Ia) or (Ib) | H₃C—[pyrrolidinone with NH] | Cl |
| ANR(Ia) or (Ib) | H₃C—[pyrrolidinone with NH] | CF₃ |
| ANS(Ia) or (Ib) | H₃C—[pyrrolidinone with NH] | CH₃ |

TABLE 1-continued

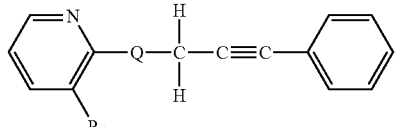

(Ia)

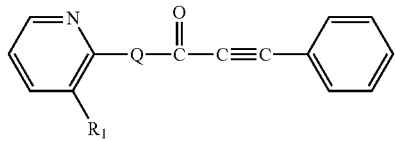

(Ib)

and pharmaceutically acceptable salts thereof, where

| Compound | Q | R₁ |
|---|---|---|
| ANT(Ia) or (Ib) | [piperidine-NH] | H |
| ANU(Ia) or (Ib) | [piperidine-NH] | NO₂ |
| ANV(Ia) or (Ib) | [piperidine-NH] | CN |
| ANW(Ia) or (Ib) | [piperidine-NH] | F |
| ANX(Ia) or (Ib) | [piperidine-NH] | Cl |
| ANY(Ia) or (Ib) | [piperidine-NH] | CF₃ |
| ANZ(Ia) or (Ib) | [piperidine-NH] | CH₃ |
| AOA(Ia) or (Ib) | [piperidinone-NH] | H |
| AOB(Ia) or (Ib) | [piperidinone-NH] | NO₂ |
| AOC(Ia) or (Ib) | [piperidinone-NH] | CN |

TABLE 1-continued

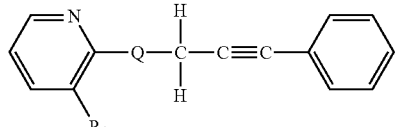

(Ia)

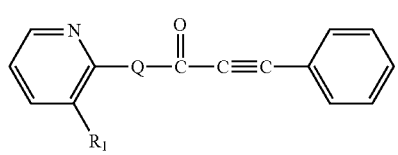

(Ib)

and pharmaceutically acceptable salts thereof, where

| Compound | Q | $R_1$ |
|---|---|---|
| AOD(Ia) or (Ib) | 2-oxopiperidin-4-yl-amino | F |
| AOE(Ia) or (Ib) | 2-oxopiperidin-4-yl-amino | Cl |
| AOF(Ia) or (Ib) | 2-oxopiperidin-4-yl-amino | $CF_3$ |
| AOG(Ia) or (Ib) | 2-oxopiperidin-4-yl-amino | $CH_3$ |
| AOH(Ia) or (Ib) | 2,6-dioxopiperidin-4-yl-amino | H |
| AOI(Ia) or (Ib) | 2,6-dioxopiperidin-4-yl-amino | $NO_2$ |
| AOJ(Ia) or (Ib) | 2,6-dioxopiperidin-4-yl-amino | CN |

TABLE 1-continued

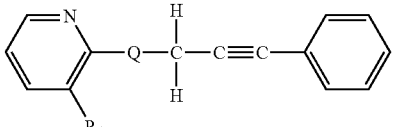

(Ia)

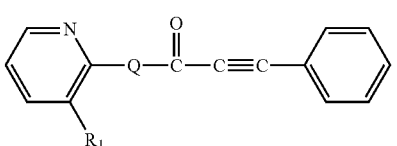

(Ib)

and pharmaceutically acceptable salts thereof, where

| Compound | Q | $R_1$ |
|---|---|---|
| AOK(Ia) or (Ib) | 2,6-dioxopiperidin-4-yl-amino | F |
| AOL(Ia) or (Ib) | 2,6-dioxopiperidin-4-yl-amino | Cl |
| AOM(Ia) or (Ib) | 2,6-dioxopiperidin-4-yl-amino | $CF_3$ |
| AON(Ia) or (Ib) | 2,6-dioxopiperidin-4-yl-amino | $CH_3$ |
| AOO(Ia) or (Ib) | 2-methylpiperidin-4-yl-amino | H |
| AOP(Ia) or (Ib) | 2-methylpiperidin-4-yl-amino | $NO_2$ |
| AOQ(Ia) or (Ib) | 2-methylpiperidin-4-yl-amino | CN |

TABLE 1-continued

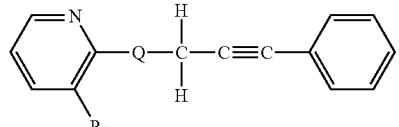

(Ia)

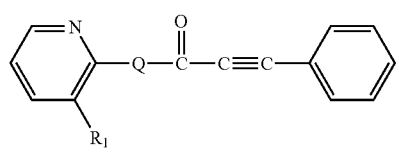

(Ib)

and pharmaceutically acceptable salts thereof, where

| Compound | Q | R₁ |
|---|---|---|
| AOR(Ia) or (Ib) | 2-methylpiperidin-4-yl (H₃C on C2) | F |
| AOS(Ia) or (Ib) | 2-methylpiperidin-4-yl | Cl |
| AOT(Ia) or (Ib) | 2-methylpiperidin-4-yl | CF₃ |
| AOU(Ia) or (Ib) | 2-methylpiperidin-4-yl | CH₃ |
| AOV(Ia) or (Ib) | 2,6-dimethylpiperidin-4-yl | H |
| AOW(Ia) or (Ib) | 2,6-dimethylpiperidin-4-yl | NO₂ |
| AOX(Ia) or (Ib) | 2,6-dimethylpiperidin-4-yl | CN |

TABLE 1-continued

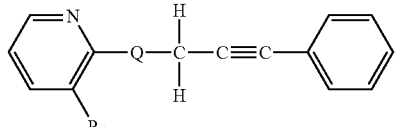

(Ia)

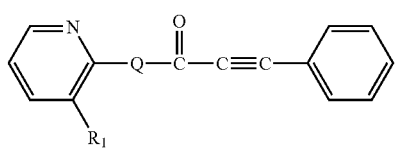

(Ib)

and pharmaceutically acceptable salts thereof, where

| Compound | Q | R₁ |
|---|---|---|
| AOY(Ia) or (Ib) | 2,6-dimethylpiperidin-4-yl | F |
| AOZ(Ia) or (Ib) | 2,6-dimethylpiperidin-4-yl | Cl |
| APA(Ia) or (Ib) | 2,6-dimethylpiperidin-4-yl | CF₃ |
| APB(Ia) or (Ib) | 2,6-dimethylpiperidin-4-yl | CH₃ |
| APC(Ia) or (Ib) | 6-methyl-2-oxopiperidin-4-yl | H |
| APD(Ia) or (Ib) | 6-methyl-2-oxopiperidin-4-yl | NO₂ |

TABLE 1-continued

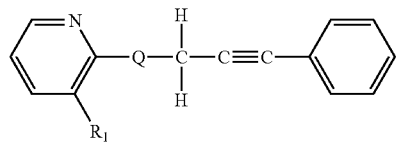

(Ia)

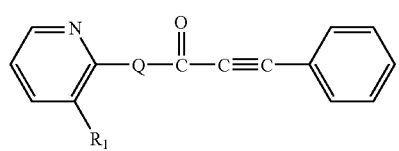

(Ib)

and pharmaceutically acceptable salts thereof, where

| Compound | Q | $R_1$ |
|---|---|---|
| APE(Ia) or (Ib) | 6-methyl-2-oxopiperidin-4-yl | CN |
| APF(Ia) or (Ib) | 6-methyl-2-oxopiperidin-4-yl | F |
| APG(Ia) or (Ib) | 6-methyl-2-oxopiperidin-4-yl | Cl |
| APH(Ia) or (Ib) | 6-methyl-2-oxopiperidin-4-yl | $CF_3$ |
| API(Ia) or (Ib) | 6-methyl-2-oxopiperidin-4-yl | $CH_3$ |
| APJ(Ia) or (Ib) | 1-methylazepan-4-yl | H |

TABLE 1-continued

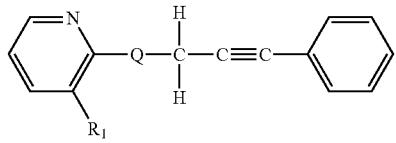

(Ia)

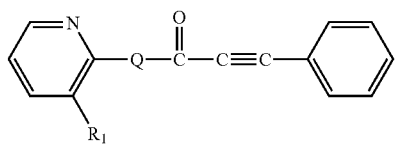

(Ib)

and pharmaceutically acceptable salts thereof, where

| Compound | Q | $R_1$ |
|---|---|---|
| APK(Ia) or (Ib) | 1-methylazepan-4-yl | $NO_2$ |
| APL(Ia) or (Ib) | 1-methylazepan-4-yl | CN |
| APM(Ia) or (Ib) | 1-methylazepan-4-yl | F |
| APN(Ia) or (Ib) | 1-methylazepan-4-yl | Cl |
| APO(Ia) or (Ib) | 1-methylazepan-4-yl | $CF_3$ |
| APP(Ia) or (Ib) | 1-methylazepan-4-yl | $CH_3$ |
| APQ(Ia) or (Ib) | 2-oxoazepan-4-yl | H |
| APR(Ia) or (Ib) | 2-oxoazepan-4-yl | $NO_2$ |

TABLE 1-continued

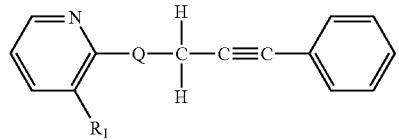

(Ia)

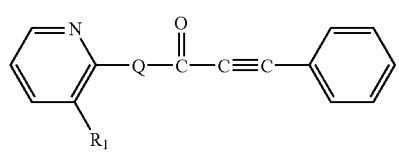

(Ib)

and pharmaceutically acceptable salts thereof, where

| Compound | Q | $R_1$ |
|---|---|---|
| APS(Ia) or (Ib) | 4-(methylamino)-1-methyl-azepan-2-one (via N) | CN |
| APT(Ia) or (Ib) | 4-(methylamino)-1-methyl-azepan-2-one (via N) | F |
| APU(Ia) or (Ib) | 4-(methylamino)-1-methyl-azepan-2-one (via N) | Cl |
| APV(Ia) or (Ib) | 4-(methylamino)-1-methyl-azepan-2-one (via N) | $CF_3$ |
| APW(Ia) or (Ib) | 4-(methylamino)-1-methyl-azepan-2-one (via N) | $CH_3$ |
| APX(Ia) or (Ib) | 4-(methylamino)-1-methyl-azepan-2-one (via N) | H |
| APY(Ia) or (Ib) | 4-(methylamino)-1-methyl-azepan-2-one (via N) | $NO_2$ |

TABLE 1-continued

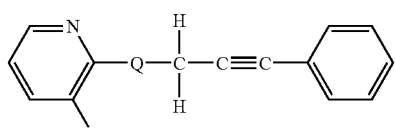

(Ia)

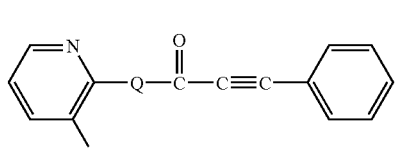

(Ib)

and pharmaceutically acceptable salts thereof, where

| Compound | Q | $R_1$ |
|---|---|---|
| APZ(Ia) or (Ib) | 5-(methylamino)-1-methyl-azepan-2-one (via N) | CN |
| AQA(Ia) or (Ib) | 5-(methylamino)-1-methyl-azepan-2-one (via N) | F |
| AQB(Ia) or (Ib) | 5-(methylamino)-1-methyl-azepan-2-one (via N) | Cl |
| AQC(Ia) or (Ib) | 5-(methylamino)-1-methyl-azepan-2-one (via N) | $CF_3$ |
| AQD(Ia) or (Ib) | 5-(methylamino)-1-methyl-azepan-2-one (via N) | $CH_3$ |
| AQE(Ia) or (Ib) | 4-(methylamino)-1-methyl-azepane-2,7-dione (via N) | H |

TABLE 1-continued

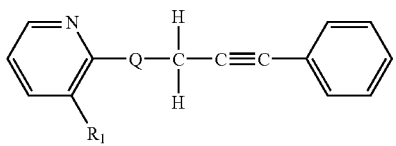

(Ia)

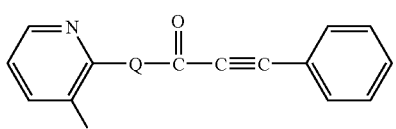

(Ib)

and pharmaceutically acceptable salts thereof, where

| Compound | Q | $R_1$ |
|---|---|---|
| AQF(Ia) or (Ib) | | $NO_2$ |
| AQG(Ia) or (Ib) | | CN |
| AQH(Ia) or (Ib) | | F |
| AQI(Ia) or (Ib) | | Cl |
| AQJ(Ia) or (Ib) | | $CF_3$ |
| AQK(Ia) or (Ib) | | $CH_3$ |

TABLE 1-continued

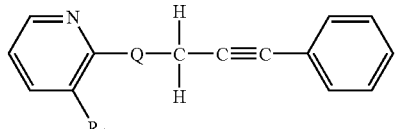

(Ia)

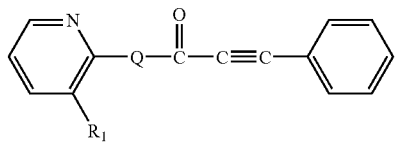

(Ib)

and pharmaceutically acceptable salts thereof, where

| Compound | Q | $R_1$ |
|---|---|---|
| AQL(Ia) or (Ib) | | H |
| AQM(Ia) or (Ib) | | $NO_2$ |
| AQN(Ia) or (Ib) | | CN |
| AQO(Ia) or (Ib) | | F |
| AQP(Ia) or (Ib) | | Cl |
| AQQ(Ia) or (Ib) | | $CF_3$ |
| AQR(Ia) or (Ib) | | $CH_3$ |

TABLE 1-continued and pharmaceutically acceptable salts thereof, where

| Compound | Q | R₁ |
|---|---|---|
| AQS(Ia) or (Ib) | 1-methyl-7-methyl-azepan-4-yl-amine | H |
| AQT(Ia) or (Ib) | 1-methyl-7-methyl-azepan-4-yl-amine | NO₂ |
| AQU(Ia) or (Ib) | 1-methyl-7-methyl-azepan-4-yl-amine | CN |
| AQV(Ia) or (Ib) | 1-methyl-7-methyl-azepan-4-yl-amine | F |
| AQW(Ia) or (Ib) | 1-methyl-7-methyl-azepan-4-yl-amine | Cl |
| AQX(Ia) or (Ib) | 1-methyl-7-methyl-azepan-4-yl-amine | CF₃ |
| AQY(Ia) or (Ib) | 1-methyl-7-methyl-azepan-4-yl-amine | CH₃ |
| AQZ(Ia) or (Ib) | 1,2,7-trimethyl-azepan-4-yl-amine | H |
| ARA(Ia) or (Ib) | 1,2,7-trimethyl-azepan-4-yl-amine | NO₂ |
| ARB(Ia) or (Ib) | 1,2,7-trimethyl-azepan-4-yl-amine | CN |
| ARC(Ia) or (Ib) | 1,2,7-trimethyl-azepan-4-yl-amine | F |
| ARD(Ia) or (Ib) | 1,2,7-trimethyl-azepan-4-yl-amine | Cl |

TABLE 1-continued

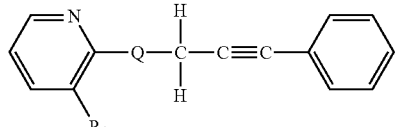

(Ia)

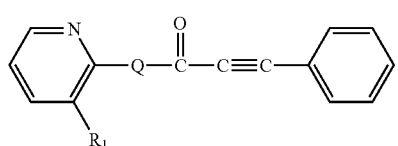

(Ib)

and pharmaceutically acceptable salts thereof, where

| Compound | Q | R₁ |
|---|---|---|
| ARE(Ia) or (Ib) | ![2,7-dimethyl-4-(methylamino)azepane] | CF₃ |
| ARF(Ia) or (Ib) | ![2,7-dimethyl-4-(methylamino)azepane] | CH₃ |
| ARG(Ia) or (Ib) | ![7-methyl-4-(methylamino)azepan-2-one] | H |
| ARH(Ia) or (Ib) | ![7-methyl-4-(methylamino)azepan-2-one] | NO₂ |
| ARI(Ia) or (Ib) | ![7-methyl-4-(methylamino)azepan-2-one] | CN |
| ARJ(Ia) or (Ib) | ![7-methyl-4-(methylamino)azepan-2-one] | F |

TABLE 1-continued

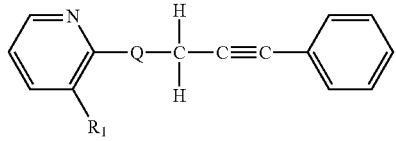

(Ia)

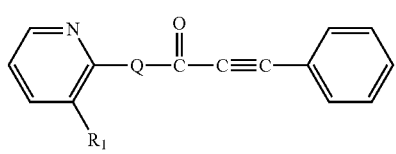

(Ib)

and pharmaceutically acceptable salts thereof, where

| Compound | Q | R₁ |
|---|---|---|
| ARK(Ia) or (Ib) | ![7-methyl-4-(methylamino)azepan-2-one] | Cl |
| ARL(Ia) or (Ib) | ![7-methyl-4-(methylamino)azepan-2-one] | CF₃ |
| ARM(Ia) or (Ib) | ![7-methyl-4-(methylamino)azepan-2-one] | CH₃ |
| ARN(Ia) or (Ib) | ![2-methyl-4-(methylamino)azepan-7-one] | H |
| ARO(Ia) or (Ib) | ![2-methyl-4-(methylamino)azepan-7-one] | NO₂ |
| ARP(Ia) or (Ib) | ![2-methyl-4-(methylamino)azepan-7-one] | CN |

TABLE 1-continued

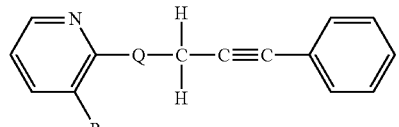

(Ia)

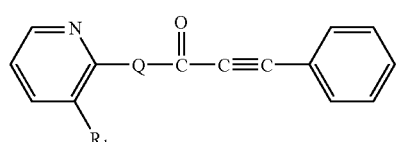

(Ib)

and pharmaceutically acceptable salts thereof, where

| Compound | Q | R₁ |
|---|---|---|
| ARQ(Ia) or (Ib) | ![structure] methyl-oxo-azepane-NH | F |
| ARR(Ia) or (Ib) | ![structure] methyl-oxo-azepane-NH | Cl |
| ARS(Ia) or (Ib) | ![structure] methyl-oxo-azepane-NH | CF₃ |
| ART(Ia) or (Ib) | ![structure] methyl-oxo-azepane-NH | CH₃ |
| ARU(Ia) or (Ib) | ![structure] azocane-NH | H |
| ARV(Ia) or (Ib) | ![structure] azocane-NH | NO₂ |
| ARW(Ia) or (Ib) | ![structure] azocane-NH | CN |

TABLE 1-continued

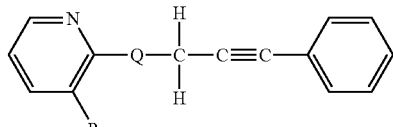

(Ia)

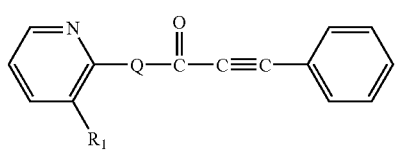

(Ib)

and pharmaceutically acceptable salts thereof, where

| Compound | Q | R₁ |
|---|---|---|
| ARX(Ia) or (Ib) | ![structure] azocane-NH | F |
| ARY(Ia) or (Ib) | ![structure] azocane-NH | Cl |
| ARZ(Ia) or (Ib) | ![structure] azocane-NH | CF₃ |
| ASA(Ia) or (Ib) | ![structure] azocane-NH | CH₃ |
| ASB(Ia) or (Ib) | ![structure] oxo-azocane-NH | H |
| ASC(Ia) or (Ib) | ![structure] oxo-azocane-NH | NO₂ |
| ASD(Ia) or (Ib) | ![structure] oxo-azocane-NH | CN |
| ASE(Ia) or (Ib) | ![structure] oxo-azocane-NH | F |

TABLE 1-continued

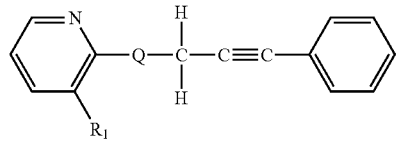

(Ia)

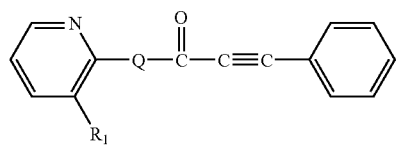

(Ib)

and pharmaceutically acceptable salts thereof, where

| Compound | Q | R₁ |
|---|---|---|
| ASF(Ia) or (Ib) | (azepanone-NH) | Cl |
| ASG(Ia) or (Ib) | (azepanone-NH) | CF₃ |
| ASH(Ia) or (Ib) | (azepanone-NH) | CH₃ |
| ASI(Ia) or (Ib) | (azepanedione-NH) | H |
| ASJ(Ia) or (Ib) | (azepanedione-NH) | NO₂ |
| ASK(Ia) or (Ib) | (azepanedione-NH) | CN |

TABLE 1-continued

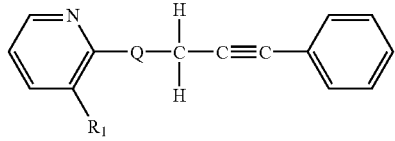

(Ia)

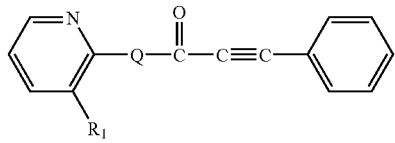

(Ib)

and pharmaceutically acceptable salts thereof, where

| Compound | Q | R₁ |
|---|---|---|
| ASL(Ia) or (Ib) | (azepanedione-NH) | F |
| ASM(Ia) or (Ib) | (azepanedione-NH) | Cl |
| ASN(Ia) or (Ib) | (azepanedione-NH) | CF₃ |
| ASO(Ia) or (Ib) | (azepanedione-NH) | CH₃ |
| ASP(Ia) or (Ib) | (2-methyl-azepane-NH) | H |
| ASQ(Ia) or (Ib) | (2-methyl-azepane-NH) | NO₂ |

TABLE 1-continued
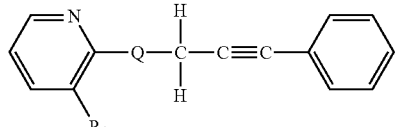
(Ia)
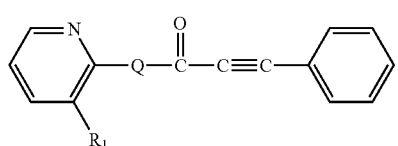
(Ib)
and pharmaceutically acceptable salts thereof, where
| Compound | Q | R₁ |
|---|---|---|
| ASR(Ia) or (Ib) |  | CN |
| ASS(Ia) or (Ib) | 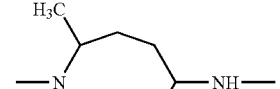 | F |
| AST(Ia) or (Ib) |  | Cl |
| ASU(Ia) or (Ib) | 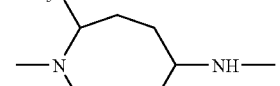 | CF₃ |
| ASV(Ia) or (Ib) |  | CH₃ |
| ASW(Ia) or (Ib) |  | H |
| ASX(Ia) or (Ib) | 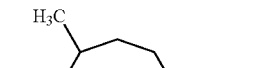 | NO₂ |
TABLE 1-continued
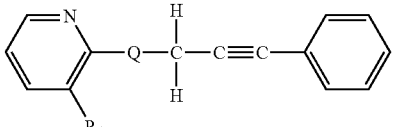
(Ia)
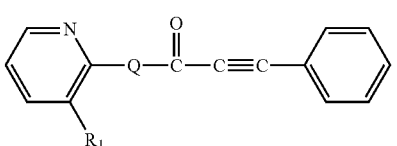
(Ib)
and pharmaceutically acceptable salts thereof, where
| Compound | Q | R₁ |
|---|---|---|
| ASY(Ia) or (Ib) | 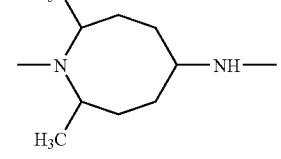 | CN |
| ASZ(Ia) or (Ib) | 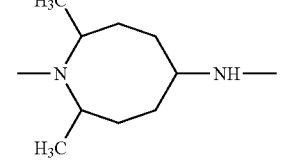 | F |
| ATA(Ia) or (Ib) | 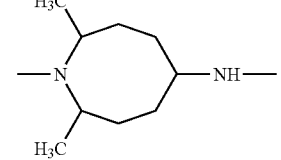 | Cl |
| ATB(Ia) or (Ib) | 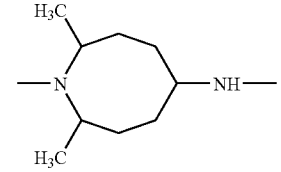 | CF₃ |
| ATC(Ia) or (Ib) | 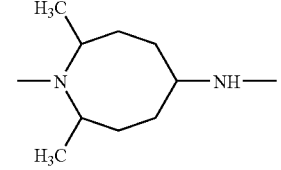 | CH₃ |
| ATD(Ia) or (Ib) | 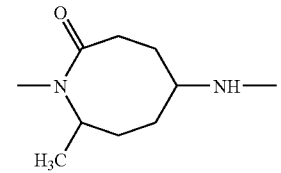 | H |

TABLE 1-continued

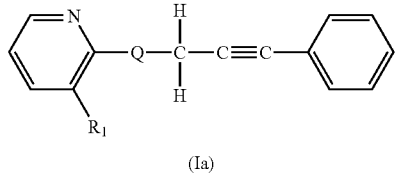

(Ia)

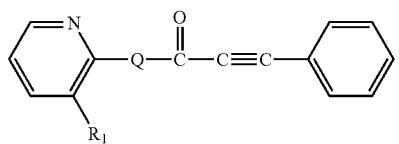

(Ib)

and pharmaceutically acceptable salts thereof, where

| Compound | Q | R₁ |
|---|---|---|
| ATE(Ia) or (Ib) | (7-membered lactam with N-CH₃ and NH, methyl substituent) | NO₂ |
| ATF(Ia) or (Ib) | (same lactam) | CN |
| ATG(Ia) or (Ib) | (same lactam) | F |
| ATH(Ia) or (Ib) | (same lactam) | Cl |
| ATI(Ia) or (Ib) | (same lactam) | CF₃ |
| ATJ(Ia) or (Ib) | (same lactam) | CH₃ |

TABLE 2

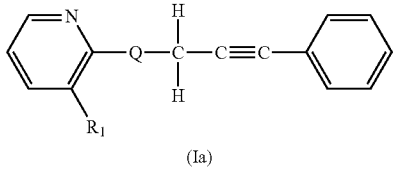

(Ia)

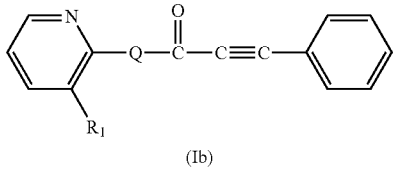

(Ib)

and pharmaceutically acceptable salts thereof, where

| Compound | Q | R₁ |
|---|---|---|
| ATK(Ia) or (Ib) | —O—(azetidine)—N— | H |
| ATL(Ia) or (Ib) | —O—(azetidine)—N— | NO₂ |
| ATM(Ia) or (Ib) | —O—(azetidine)—N— | CN |
| ATN(Ia) or (Ib) | —O—(azetidine)—N— | F |
| ATO(Ia) or (Ib) | —O—(azetidine)—N— | Cl |
| ATP(Ia) or (Ib) | —O—(azetidine)—N— | CF₃ |
| ATQ(Ia) or (Ib) | —O—(azetidine)—N— | CH₃ |
| ATR(Ia) or (Ib) | —O—(2-methyl azetidine)—N— | H |
| ATS(Ia) or (Ib) | —O—(2-methyl azetidine)—N— | NO₂ |
| ATT(Ia) or (Ib) | —O—(2-methyl azetidine)—N— | CN |
| ATU(Ia) or (Ib) | —O—(2-methyl azetidine)—N— | F |

TABLE 2-continued

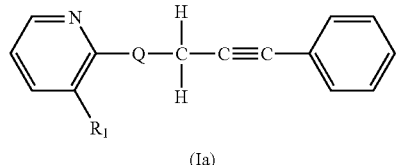

(Ia)

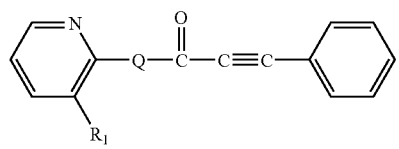

(Ib)

and pharmaceutically acceptable salts thereof, where

| Compound | Q | R₁ |
|---|---|---|
| ATV(Ia) or (Ib) | 2-methylazetidin-3-yloxy (—O—[2-Me-azetidine]) | Cl |
| ATW(Ia) or (Ib) | 2-methylazetidin-3-yloxy | CF₃ |
| ATX(Ia) or (Ib) | 2-methylazetidin-3-yloxy | CH₃ |
| ATY(Ia) or (Ib) | 2,4-dimethylazetidin-3-yloxy | H |
| ATZ(Ia) or (Ib) | 2,4-dimethylazetidin-3-yloxy | NO₂ |
| AUA(Ia) or (Ib) | 2,4-dimethylazetidin-3-yloxy | CN |
| AUB(Ia) or (Ib) | 2,4-dimethylazetidin-3-yloxy | F |

TABLE 2-continued

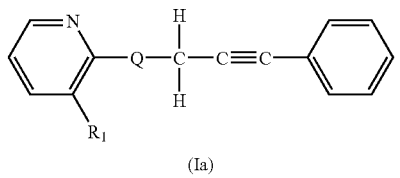

(Ia)

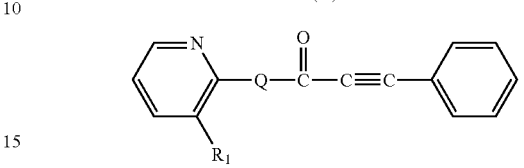

(Ib)

and pharmaceutically acceptable salts thereof, where

| Compound | Q | R₁ |
|---|---|---|
| AUC(Ia) or (Ib) | 2,4-dimethylazetidin-3-yloxy | Cl |
| AUD(Ia) or (Ib) | 2,4-dimethylazetidin-3-yloxy | CF₃ |
| AUE(Ia) or (Ib) | 2,4-dimethylazetidin-3-yloxy | CH₃ |
| AUF(Ia) or (Ib) | 2-oxoazetidin-3-yloxy | H |
| AUG(Ia) or (Ib) | 2-oxoazetidin-3-yloxy | NO₂ |
| AUH(Ia) or (Ib) | 2-oxoazetidin-3-yloxy | CN |
| AUI(Ia) or (Ib) | 2-oxoazetidin-3-yloxy | F |

TABLE 2-continued

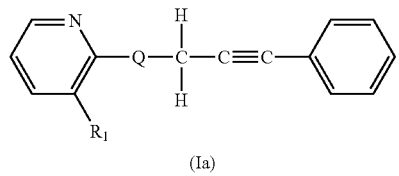

(Ia)

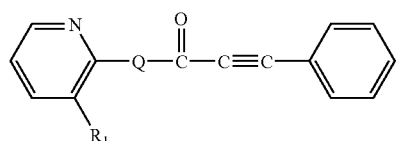

(Ib)

and pharmaceutically acceptable salts thereof, where

| Compound | Q | R₁ |
|---|---|---|
| AUJ(Ia) or (Ib) | —O—(3-oxoazetidin-2-yl-oxy, N-methyl) | Cl |
| AUK(Ia) or (Ib) | —O—(3-oxoazetidin-2-yl-oxy, N-methyl) | CF₃ |
| AUL(Ia) or (Ib) | —O—(3-oxoazetidin-2-yl-oxy, N-methyl) | CH₃ |
| AUM(Ia) or (Ib) | —O—(3-oxoazetidin-2-yl-oxy, N-methyl) | H |
| AUN(Ia) or (Ib) | —O—(3-oxoazetidin-2-yl-oxy, N-methyl) | NO₂ |
| AUO(Ia) or (Ib) | —O—(3-oxoazetidin-2-yl-oxy, N-methyl) | CN |
| AUP(Ia) or (Ib) | —O—(3-oxoazetidin-2-yl-oxy, N-methyl) | F |

TABLE 2-continued

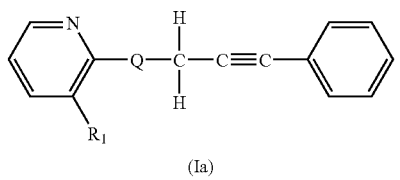

(Ia)

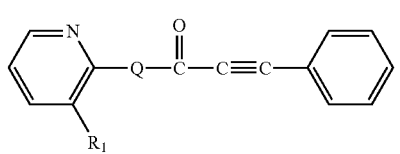

(Ib)

and pharmaceutically acceptable salts thereof, where

| Compound | Q | R₁ |
|---|---|---|
| AUQ(Ia) or (Ib) | —O—(2,4-dioxoazetidinyl, N-methyl) | Cl |
| AUR(Ia) or (Ib) | —O—(2,4-dioxoazetidinyl, N-methyl) | CF₃ |
| AUS(Ia) or (Ib) | —O—(2,4-dioxoazetidinyl, N-methyl) | CH₃ |
| AUT(Ia) or (Ib) | —O—(3-oxo-4-methylazetidinyl, N-methyl) | H |
| AUU(Ia) or (Ib) | —O—(3-oxo-4-methylazetidinyl, N-methyl) | NO₂ |
| AUV(Ia) or (Ib) | —O—(3-oxo-4-methylazetidinyl, N-methyl) | CN |

TABLE 2-continued

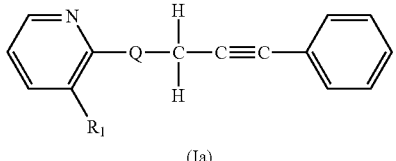

(Ia)

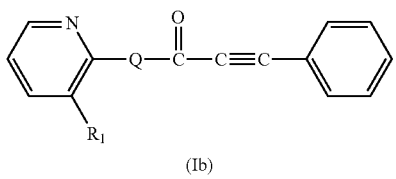

(Ib)

and pharmaceutically acceptable salts thereof, where

| Compound | Q | R₁ |
|---|---|---|
| AUW(Ia) or (Ib) | ![azetidinone-CH3] | F |
| AUX(Ia) or (Ib) | ![azetidinone-CH3] | Cl |
| AUY(Ia) or (Ib) | ![azetidinone-CH3] | CF₃ |
| AUZ(Ia) or (Ib) | ![azetidinone-CH3] | CH₃ |
| AVA(Ia) or (Ib) | ![N-methylpyrrolidin-3-yloxy] | H |
| AVB(Ia) or (Ib) | ![N-methylpyrrolidin-3-yloxy] | NO₂ |
| AVC(Ia) or (Ib) | ![N-methylpyrrolidin-3-yloxy] | CN |
| AVD(Ia) or (Ib) | ![N-methylpyrrolidin-3-yloxy] | F |
| AVE(Ia) or (Ib) | ![N-methylpyrrolidin-3-yloxy] | Cl |
| AVF(Ia) or (Ib) | ![N-methylpyrrolidin-3-yloxy] | CF₃ |
| AVG(Ia) or (Ib) | ![N-methylpyrrolidin-3-yloxy] | CH₃ |
| AVH(Ia) or (Ib) | ![N-methyl-5-oxopyrrolidin-3-yloxy] | H |
| AVI(Ia) or (Ib) | ![N-methyl-5-oxopyrrolidin-3-yloxy] | NO₂ |
| AVJ(Ia) or (Ib) | ![N-methyl-5-oxopyrrolidin-3-yloxy] | CN |
| AVK(Ia) or (Ib) | ![N-methyl-5-oxopyrrolidin-3-yloxy] | F |
| AVL(Ia) or (Ib) | ![N-methyl-5-oxopyrrolidin-3-yloxy] | Cl |
| AVM(Ia) or (Ib) | ![N-methyl-5-oxopyrrolidin-3-yloxy] | CF₃ |
| AVN(Ia) or (Ib) | ![N-methyl-5-oxopyrrolidin-3-yloxy] | CH₃ |

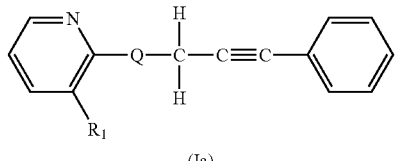

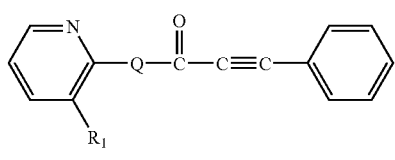

TABLE 2-continued

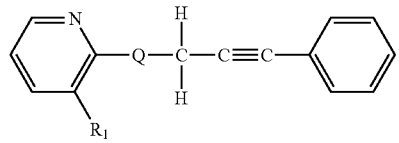

(Ia)

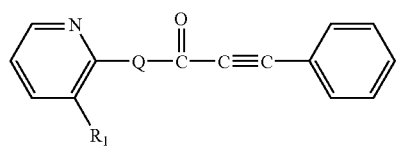

(Ib)

and pharmaceutically acceptable salts thereof, where

| Compound | Q | $R_1$ |
|---|---|---|
| AVO(Ia) or (Ib) | 3-(1-methyl-2-oxopyrrolidin-3-yl)oxy | H |
| AVP(Ia) or (Ib) | 3-(1-methyl-2-oxopyrrolidin-3-yl)oxy | $NO_2$ |
| AVQ(Ia) or (Ib) | 3-(1-methyl-2-oxopyrrolidin-3-yl)oxy | CN |
| AVR(Ia) or (Ib) | 3-(1-methyl-2-oxopyrrolidin-3-yl)oxy | F |
| AVS(Ia) or (Ib) | 3-(1-methyl-2-oxopyrrolidin-3-yl)oxy | Cl |
| AVT(Ia) or (Ib) | 3-(1-methyl-2-oxopyrrolidin-3-yl)oxy | $CF_3$ |
| AVU(Ia) or (Ib) | 3-(1-methyl-2-oxopyrrolidin-3-yl)oxy | $CH_3$ |
| AVV(Ia) or (Ib) | 3-(1-methyl-2,5-dioxopyrrolidin-3-yl)oxy | H |

TABLE 2-continued

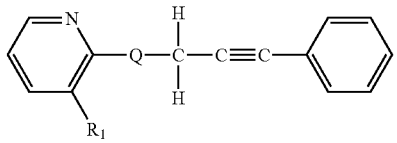

(Ia)

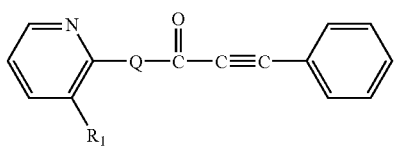

(Ib)

and pharmaceutically acceptable salts thereof, where

| Compound | Q | $R_1$ |
|---|---|---|
| AVW(Ia) or (Ib) | 3-(1-methyl-2,5-dioxopyrrolidin-3-yl)oxy | $NO_2$ |
| AVX(Ia) or (Ib) | 3-(1-methyl-2,5-dioxopyrrolidin-3-yl)oxy | CN |
| AVY(Ia) or (Ib) | 3-(1-methyl-2,5-dioxopyrrolidin-3-yl)oxy | F |
| AVZ(Ia) or (Ib) | 3-(1-methyl-2,5-dioxopyrrolidin-3-yl)oxy | Cl |
| AWA(Ia) or (Ib) | 3-(1-methyl-2,5-dioxopyrrolidin-3-yl)oxy | $CF_3$ |
| AWB(Ia) or (Ib) | 3-(1-methyl-2,5-dioxopyrrolidin-3-yl)oxy | $CH_3$ |
| AWC(Ia) or (Ib) | 4-(1,2-dimethylpyrrolidin-4-yl)oxy | H |
| AWD(Ia) or (Ib) | 4-(1,2-dimethylpyrrolidin-4-yl)oxy | $NO_2$ |

TABLE 2-continued

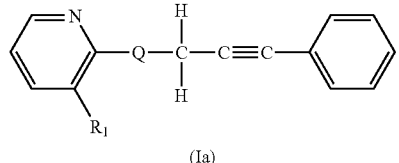

(Ia)

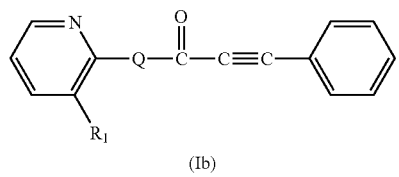

(Ib)

and pharmaceutically acceptable salts thereof, where

| Compound | Q | R₁ |
|---|---|---|
| AWE(Ia) or (Ib) | | CN |
| AWF(Ia) or (Ib) | | F |
| AWG(Ia) or (Ib) | | Cl |
| AWH(Ia) or (Ib) | | CF₃ |
| AWI(Ia) or (Ib) | | CH₃ |
| AWJ(Ia) or (Ib) | | H |
| AWK(Ia) or (Ib) | | NO₂ |
| AWL(Ia) or (Ib) | | CN |
| AWM(Ia) or (Ib) | | F |

TABLE 2-continued

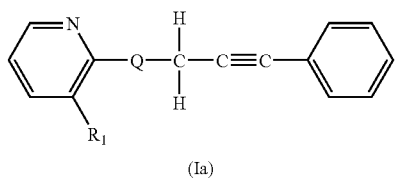

(Ia)

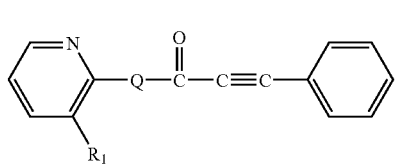

(Ib)

and pharmaceutically acceptable salts thereof, where

| Compound | Q | R₁ |
|---|---|---|
| AWN(Ia) or (Ib) | | Cl |
| AWO(Ia) or (Ib) | | CF₃ |
| AWP(Ia) or (Ib) | | CH₃ |
| AWQ(Ia) or (Ib) | | H |
| AWR(Ia) or (Ib) | | NO₂ |
| AWS(Ia) or (Ib) | | CN |
| AWT(Ia) or (Ib) | | F |

TABLE 2-continued

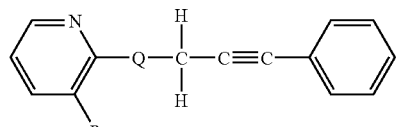
(Ia)

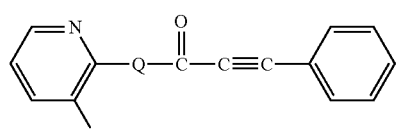
(Ib)

and pharmaceutically acceptable salts thereof, where

| Compound | Q | R₁ |
|---|---|---|
| AWU(Ia) or (Ib) | 2,5-dimethyl-1-methyl-pyrrolidin-3-yloxy | Cl |
| AWV(Ia) or (Ib) | 2,5-dimethyl-1-methyl-pyrrolidin-3-yloxy | CF₃ |
| AWW(Ia) or (Ib) | 2,5-dimethyl-1-methyl-pyrrolidin-3-yloxy | CH₃ |
| AWX(Ia) or (Ib) | 5-methyl-1-methyl-2-oxo-pyrrolidin-3-yloxy | H |
| AWY(Ia) or (Ib) | 5-methyl-1-methyl-2-oxo-pyrrolidin-3-yloxy | NO₂ |
| AWZ(Ia) or (Ib) | 5-methyl-1-methyl-2-oxo-pyrrolidin-3-yloxy | CN |
| AXA(Ia) or (Ib) | 5-methyl-1-methyl-2-oxo-pyrrolidin-3-yloxy | F |

TABLE 2-continued

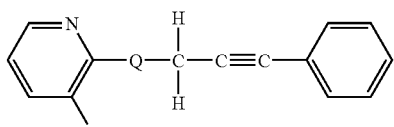
(Ia)

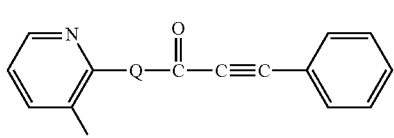
(Ib)

and pharmaceutically acceptable salts thereof, where

| Compound | Q | R₁ |
|---|---|---|
| AXB(Ia) or (Ib) | 2-methyl-1-methyl-5-oxo-pyrrolidin-3-yloxy | Cl |
| AXC(Ia) or (Ib) | 2-methyl-1-methyl-5-oxo-pyrrolidin-3-yloxy | CF₃ |
| AXD(Ia) or (Ib) | 2-methyl-1-methyl-5-oxo-pyrrolidin-3-yloxy | CH₃ |
| AXE(Ia) or (Ib) | 5-methyl-1-methyl-2,5-dioxo-pyrrolidin-3-yloxy | H |
| AXF(Ia) or (Ib) | 5-methyl-1-methyl-2,5-dioxo-pyrrolidin-3-yloxy | NO₂ |
| AXG(Ia) or (Ib) | 5-methyl-1-methyl-2,5-dioxo-pyrrolidin-3-yloxy | CN |
| AXH(Ia) or (Ib) | 5-methyl-1-methyl-2,5-dioxo-pyrrolidin-3-yloxy | F |

TABLE 2-continued

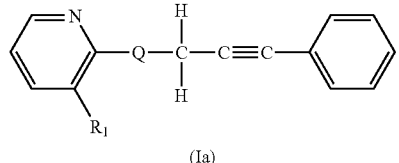
(Ia)

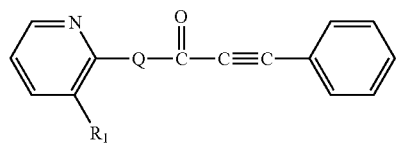
(Ib)

and pharmaceutically acceptable salts thereof, where

| Compound | Q | R₁ |
|---|---|---|
| AXI(Ia) or (Ib) | 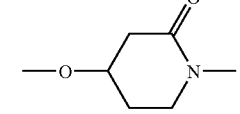 | Cl |
| AXJ(Ia) or (Ib) | 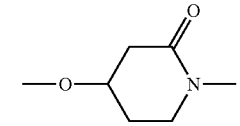 | CF₃ |
| AXK(Ia) or (Ib) | 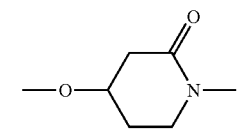 | CH₃ |
| AXL(Ia) or (Ib) | 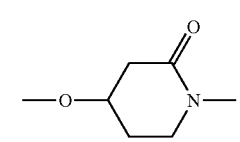 | H |
| AXM(Ia) or (Ib) | 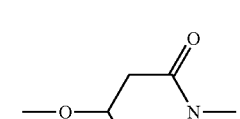 | NO₂ |
| AXN(Ia) or (Ib) |  | CN |
| AXO(Ia) or (Ib) | 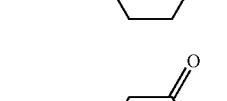 | F |
| AXP(Ia) or (Ib) | 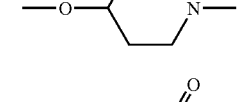 | Cl |
| AXQ(Ia) or (Ib) |  | CF₃ |
| AXR(Ia) or (Ib) |  | CH₃ |

TABLE 2-continued

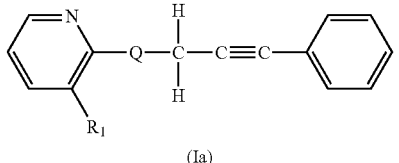
(Ia)

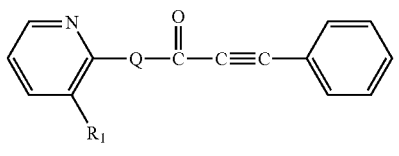
(Ib)

and pharmaceutically acceptable salts thereof, where

| Compound | Q | R₁ |
|---|---|---|
| AXS(Ia) or (Ib) |  | H |
| AXT(Ia) or (Ib) |  | NO₂ |
| AXU(Ia) or (Ib) |  | CN |
| AXV(Ia) or (Ib) |  | F |
| AXW(Ia) or (Ib) |  | Cl |
| AXX(Ia) or (Ib) |  | CF₃ |
| AXY(Ia) or (Ib) |  | CH₃ |
| AXZ(Ia) or (Ib) |  | H |

TABLE 2-continued

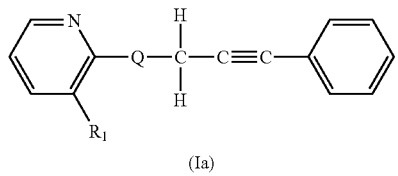

(Ia)

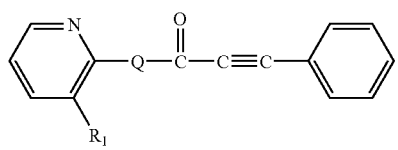

(Ib)

and pharmaceutically acceptable salts thereof, where

| Compound | Q | R₁ |
|---|---|---|
| AYA(Ia) or (Ib) | ![](O-piperidine-2,6-dione-N-methyl) | NO₂ |
| AYB(Ia) or (Ib) | ![](O-piperidine-2,6-dione-N-methyl) | CN |
| AYC(Ia) or (Ib) | ![](O-piperidine-2,6-dione-N-methyl) | F |
| AYD(Ia) or (Ib) | ![](O-piperidine-2,6-dione-N-methyl) | Cl |
| AYE(Ia) or (Ib) | ![](O-piperidine-2,6-dione-N-methyl) | CF₃ |
| AYF(Ia) or (Ib) | ![](O-piperidine-2,6-dione-N-methyl) | CH₃ |

TABLE 2-continued

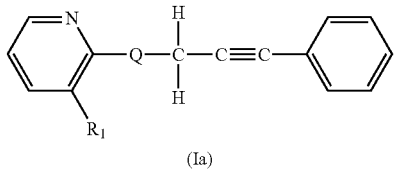

(Ia)

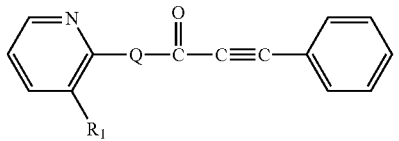

(Ib)

and pharmaceutically acceptable salts thereof, where

| Compound | Q | R₁ |
|---|---|---|
| AYG(Ia) or (Ib) | | H |
| AYH(Ia) or (Ib) | | NO₂ |
| AYI(Ia) or (Ib) | | CN |
| AYJ(Ia) or (Ib) | | F |
| AYK(Ia) or (Ib) | | Cl |
| AYL(Ia) or (Ib) | | CF₃ |
| AYM(Ia) or (Ib) | | CH₃ |
| AYN(Ia) or (Ib) | ![](O-2,6-dimethyl-N-methylpiperidine) | H |

TABLE 2-continued

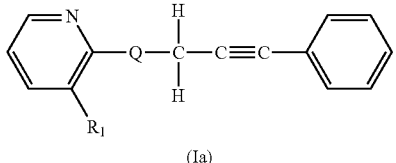

(Ia)

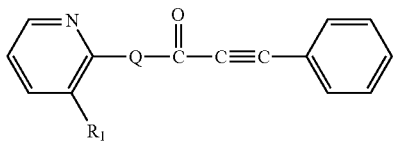

(Ib)

and pharmaceutically acceptable salts thereof, where

| Compound | Q | R₁ |
|---|---|---|
| AYO(Ia) or (Ib) | 2,6-dimethyl-N-methylpiperidin-4-yloxy | NO₂ |
| AYP(Ia) or (Ib) | 2,6-dimethyl-N-methylpiperidin-4-yloxy | CN |
| AYQ(Ia) or (Ib) | 2,6-dimethyl-N-methylpiperidin-4-yloxy | F |
| AYR(Ia) or (Ib) | 2,6-dimethyl-N-methylpiperidin-4-yloxy | Cl |
| AYS(Ia) or (Ib) | 2,6-dimethyl-N-methylpiperidin-4-yloxy | CF₃ |
| AYT(Ia) or (Ib) | 2,6-dimethyl-N-methylpiperidin-4-yloxy | CH₃ |

TABLE 2-continued

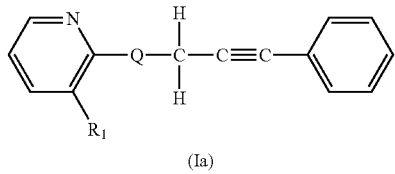

(Ia)

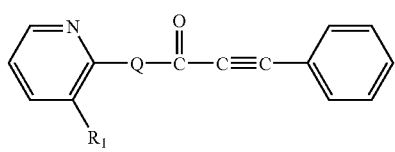

(Ib)

and pharmaceutically acceptable salts thereof, where

| Compound | Q | R₁ |
|---|---|---|
| AYU(Ia) or (Ib) | 6-methyl-N-methyl-2-oxopiperidin-4-yloxy | H |
| AYV(Ia) or (Ib) | 6-methyl-N-methyl-2-oxopiperidin-4-yloxy | NO₂ |
| AYW(Ia) or (Ib) | 6-methyl-N-methyl-2-oxopiperidin-4-yloxy | CN |
| AYX(Ia) or (Ib) | 6-methyl-N-methyl-2-oxopiperidin-4-yloxy | F |
| AYY(Ia) or (Ib) | 6-methyl-N-methyl-2-oxopiperidin-4-yloxy | Cl |
| AYZ(Ia) or (Ib) | 6-methyl-N-methyl-2-oxopiperidin-4-yloxy | CF₃ |

TABLE 2-continued

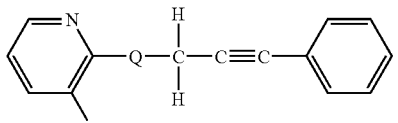

(Ia)

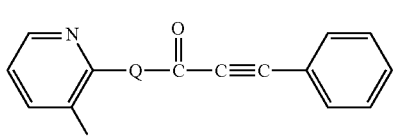

(Ib)

and pharmaceutically acceptable salts thereof, where

| Compound | Q | R₁ |
|---|---|---|
| AZA(Ia) or (Ib) | 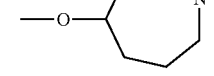 | CH₃ |
| AZB(Ia) or (Ib) | 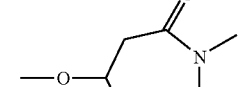 | H |
| AZC(Ia) or (Ib) |  | NO₂ |
| AZD(Ia) or (Ib) | 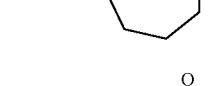 | CN |
| AZE(Ia) or (Ib) | 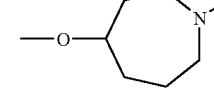 | F |
| AZF(Ia) or (Ib) |  | Cl |
| AZG(Ia) or (Ib) |  | CF₃ |
| AZH(Ia) or (Ib) | | CH₃ |

TABLE 2-continued

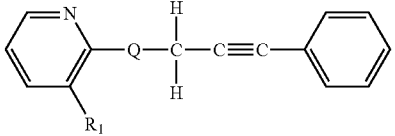

(Ia)

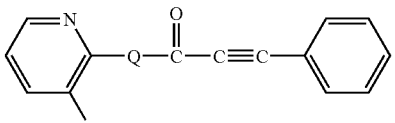

(Ib)

and pharmaceutically acceptable salts thereof, where

| Compound | Q | R₁ |
|---|---|---|
| AZI(Ia) or (Ib) | | H |
| AZJ(Ia) or (Ib) | | NO₂ |
| AZK(Ia) or (Ib) | | CN |
| AZL(Ia) or (Ib) | | F |
| AZM(Ia) or (Ib) | | Cl |
| AZN(Ia) or (Ib) | | CF₃ |
| AZO(Ia) or (Ib) | | CH₃ |

TABLE 2-continued

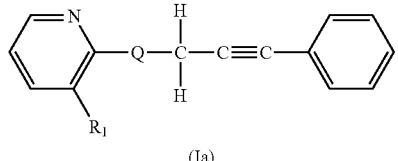

(Ia)

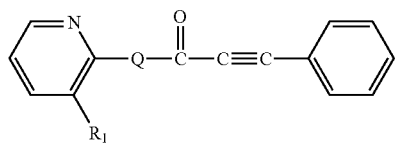

(Ib)

and pharmaceutically acceptable salts thereof, where

| Compound | Q | R₁ |
|---|---|---|
| AZP(Ia) or (Ib) | | H |
| AZQ(Ia) or (Ib) | | $NO_2$ |
| AZR(Ia) or (Ib) | | CN |
| AZS(Ia) or (Ib) | | F |
| AZT(Ia) or (Ib) | | Cl |
| AZU(Ia) or (Ib) | | $CF_3$ |
| AZV(Ia) or (Ib) | | $CH_3$ |
| AZW(Ia) or (Ib) | | H |
| AZX(Ia) or (Ib) | | $NO_2$ |

TABLE 2-continued

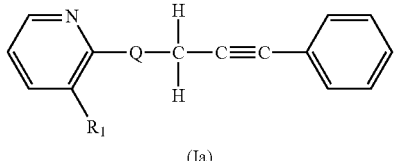

(Ia)

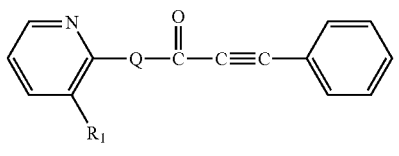

(Ib)

and pharmaceutically acceptable salts thereof, where

| Compound | Q | R₁ |
|---|---|---|
| AZY(Ia) or (Ib) | | CN |
| AZZ(Ia) or (Ib) | | F |
| BAA(Ia) or (Ib) | | Cl |
| BAB(Ia) or (Ib) | | $CF_3$ |
| BAC(Ia) or (Ib) | | $CH_3$ |
| BAD(Ia) or (Ib) | | H |
| BAE(Ia) or (Ib) | | $NO_2$ |

TABLE 2-continued

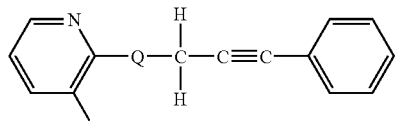
(Ia)

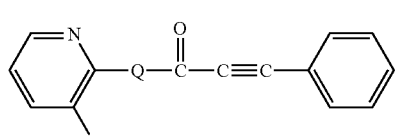
(Ib)

and pharmaceutically acceptable salts thereof, where

| Compound | Q | R₁ |
|---|---|---|
| BAF(Ia) or (Ib) | ![azepane with CH₃, N-CH₃, O-] | CN |
| BAG(Ia) or (Ib) | ![azepane with CH₃, N-CH₃, O-] | F |
| BAH(Ia) or (Ib) | ![azepane with CH₃, N-CH₃, O-] | Cl |
| BAI(Ia) or (Ib) | ![azepane with CH₃, N-CH₃, O-] | CF₃ |
| BAJ(Ia) or (Ib) | ![azepane with CH₃, N-CH₃, O-] | CH₃ |
| BAK(Ia) or (Ib) | ![azepane with N-CH₃, CH₃, O-] | H |
| BAL(Ia) or (Ib) | ![azepane with N-CH₃, CH₃, O-] | NO₂ |

TABLE 2-continued

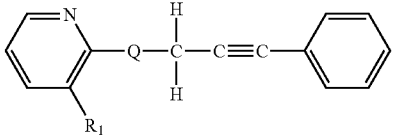
(Ia)

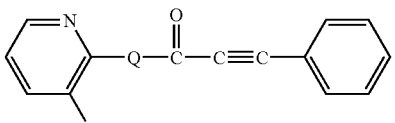
(Ib)

and pharmaceutically acceptable salts thereof, where

| Compound | Q | R₁ |
|---|---|---|
| BAM(Ia) or (Ib) | ![azepane with N-CH₃, CH₃, O-] | CN |
| BAN(Ia) or (Ib) | ![azepane with N-CH₃, CH₃, O-] | F |
| BAO(Ia) or (Ib) | ![azepane with N-CH₃, CH₃, O-] | Cl |
| BAP(Ia) or (Ib) | ![azepane with N-CH₃, CH₃, O-] | CF₃ |
| BAQ(Ia) or (Ib) | ![azepane with N-CH₃, CH₃, O-] | CH₃ |
| BAR(Ia) or (Ib) | ![azepane with CH₃, N-CH₃, CH₃, O-] | H |
| BAS(Ia) or (Ib) | ![azepane with CH₃, N-CH₃, CH₃, O-] | NO₂ |
| BAT(Ia) or (Ib) | ![azepane with CH₃, N-CH₃, CH₃, O-] | CN |

TABLE 2-continued

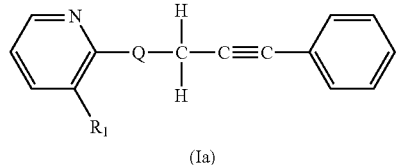

(Ia)

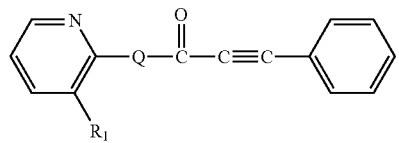

(Ib)

and pharmaceutically acceptable salts thereof, where

| Compound | Q | R₁ |
|---|---|---|
| BAU(Ia) or (Ib) | ![structure] | F |
| BAV(Ia) or (Ib) | ![structure] | Cl |
| BAW(Ia) or (Ib) | ![structure] | CF₃ |
| BAX(Ia) or (Ib) | ![structure] | CH₃ |
| BAY(Ia) or (Ib) | ![structure] | H |
| BAZ(Ia) or (Ib) | ![structure] | NO₂ |
| BBA(Ia) or (Ib) | ![structure] | CN |

TABLE 2-continued

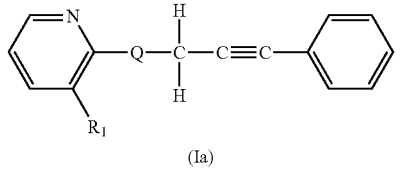

(Ia)

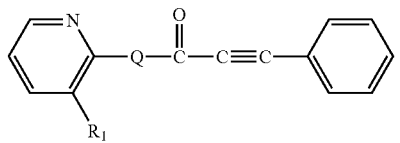

(Ib)

and pharmaceutically acceptable salts thereof, where

| Compound | Q | R₁ |
|---|---|---|
| BBB(Ia) or (Ib) | ![structure] | F |
| BBC(Ia) or (Ib) | ![structure] | Cl |
| BBD(Ia) or (Ib) | ![structure] | CF₃ |
| BBE(Ia) or (Ib) | ![structure] | CH₃ |
| BBF(Ia) or (Ib) | ![structure] | H |
| BBG(Ia) or (Ib) | ![structure] | NO₂ |
| BBH(Ia) or (Ib) | ![structure] | CN |

TABLE 2-continued

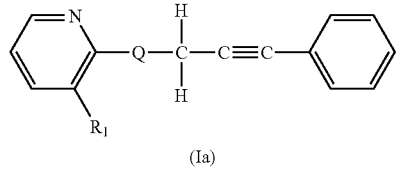

(Ia)

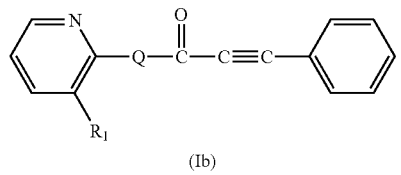

(Ib)

and pharmaceutically acceptable salts thereof, where

| Compound | Q | R₁ |
|---|---|---|
| BBI(Ia) or (Ib) | methyl-substituted N-methyl caprolactam-O- | F |
| BBJ(Ia) or (Ib) | methyl-substituted N-methyl caprolactam-O- | Cl |
| BBK(Ia) or (Ib) | methyl-substituted N-methyl caprolactam-O- | $CF_3$ |
| BBL(Ia) or (Ib) | methyl-substituted N-methyl caprolactam-O- | $CH_3$ |
| BBM(Ia) or (Ib) | N-methyl azocan-O- | H |
| BBN(Ia) or (Ib) | N-methyl azocan-O- | $NO_2$ |
| BBO(Ia) or (Ib) | N-methyl azocan-O- | CN |
| BBP(Ia) or (Ib) | N-methyl azocan-O- | F |

TABLE 2-continued

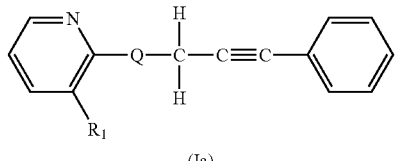

(Ia)

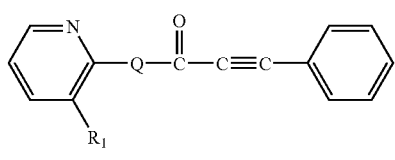

(Ib)

and pharmaceutically acceptable salts thereof, where

| Compound | Q | R₁ |
|---|---|---|
| BBQ(Ia) or (Ib) | N-methyl azocan-O- | Cl |
| BBR(Ia) or (Ib) | N-methyl azocan-O- | $CF_3$ |
| BBS(Ia) or (Ib) | N-methyl azocan-O- | $CH_3$ |
| BBT(Ia) or (Ib) | N-methyl azocan-2-one-O- | H |
| BBU(Ia) or (Ib) | N-methyl azocan-2-one-O- | $NO_2$ |
| BBV(Ia) or (Ib) | N-methyl azocan-2-one-O- | CN |
| BBW(Ia) or (Ib) | N-methyl azocan-2-one-O- | F |
| BBX(Ia) or (Ib) | N-methyl azocan-2-one-O- | Cl |

TABLE 2-continued

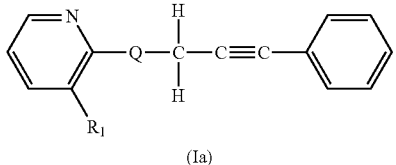

(Ia)

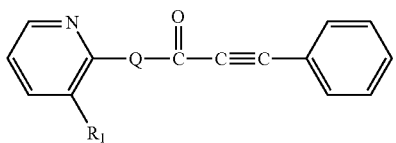

(Ib)

and pharmaceutically acceptable salts thereof, where

| Compound | Q | R₁ |
|---|---|---|
| BBY(Ia) or (Ib) | 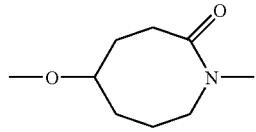 | CF₃ |
| BBZ(Ia) or (Ib) | 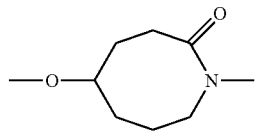 | CH₃ |
| BCA(Ia) or (Ib) | 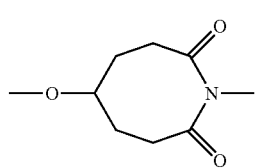 | H |
| BCB(Ia) or (Ib) | 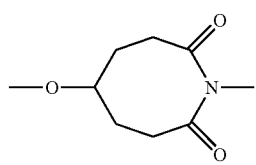 | NO₂ |
| BCC(Ia) or (Ib) | 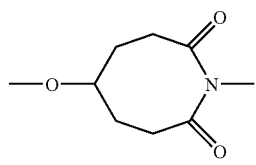 | CN |
| BCD(Ia) or (Ib) | 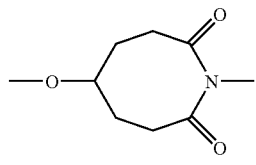 | F |
| BCE(Ia) or (Ib) | 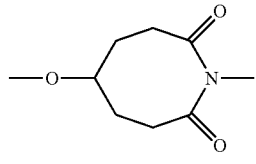 | Cl |

TABLE 2-continued

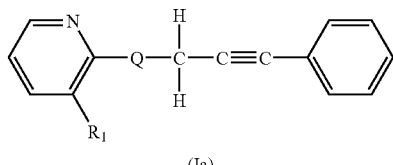

(Ia)

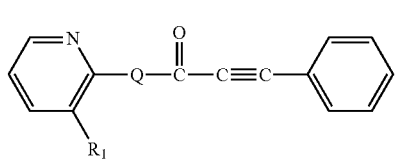

(Ib)

and pharmaceutically acceptable salts thereof, where

| Compound | Q | R₁ |
|---|---|---|
| BCF(Ia) or (Ib) | 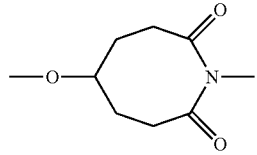 | CF₃ |
| BCG(Ia) or (Ib) | 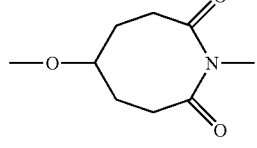 | CH₃ |
| BCH(Ia) or (Ib) | 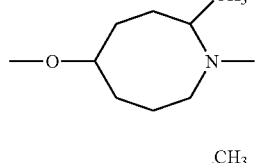 | H |
| BCI(Ia) or (Ib) | 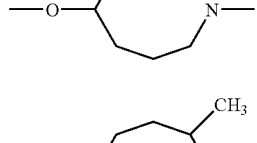 | NO₂ |
| BCJ(Ia) or (Ib) | 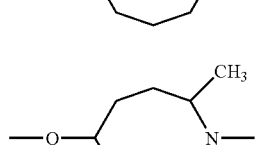 | CN |
| BCK(Ia) or (Ib) | 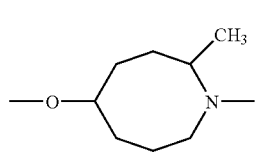 | F |
| BCL(Ia) or (Ib) |  | Cl |

TABLE 2-continued

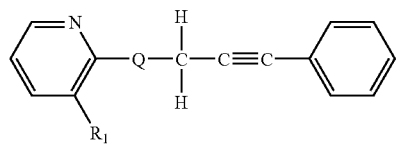

(Ia)

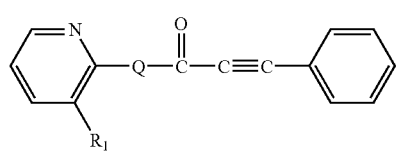

(Ib)

and pharmaceutically acceptable salts thereof, where

| Compound | Q | R₁ |
|---|---|---|
| BCM(Ia) or (Ib) | 2-methyl-1-methyl-azocan-5-yloxy (—O—azocane with CH₃ at 2, N-CH₃) | CF₃ |
| BCN(Ia) or (Ib) | same azocanyloxy | CH₃ |
| BCO(Ia) or (Ib) | 2,8-dimethyl-1-methyl-azocan-5-yloxy | H |
| BCP(Ia) or (Ib) | 2,8-dimethyl-1-methyl-azocan-5-yloxy | NO₂ |
| BCQ(Ia) or (Ib) | 2,8-dimethyl-1-methyl-azocan-5-yloxy | CN |
| BCR(Ia) or (Ib) | 2,8-dimethyl-1-methyl-azocan-5-yloxy | F |
| BCS(Ia) or (Ib) | 2,8-dimethyl-1-methyl-azocan-5-yloxy | Cl |
| BCT(Ia) or (Ib) | 2,8-dimethyl-1-methyl-azocan-5-yloxy | CF₃ |
| BCU(Ia) or (Ib) | 2,8-dimethyl-1-methyl-azocan-5-yloxy | CH₃ |
| BCV(Ia) or (Ib) | 8-methyl-2-oxo-azocan-5-yloxy | H |
| BCW(Ia) or (Ib) | 8-methyl-2-oxo-azocan-5-yloxy | NO₂ |
| BCX(Ia) or (Ib) | 8-methyl-2-oxo-azocan-5-yloxy | CN |

TABLE 2-continued

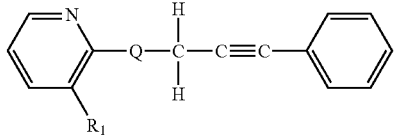

(Ia)

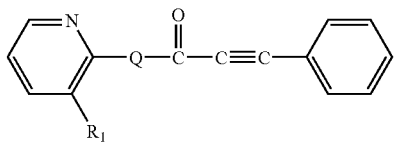

(Ib)

and pharmaceutically acceptable salts thereof, where

TABLE 2-continued

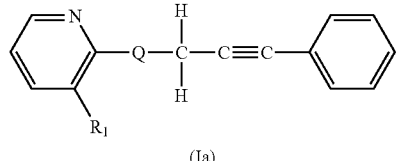

(Ia)

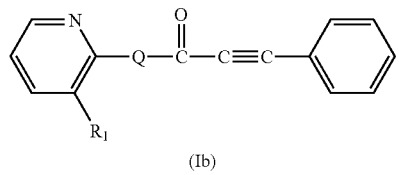

(Ib)

and pharmaceutically acceptable salts thereof, where

| Compound | Q | R₁ |
|---|---|---|
| BCY(Ia) or (Ib) | —O— (8-membered lactam with CH₃) | F |
| BCZ(Ia) or (Ib) | —O— (8-membered lactam with CH₃) | Cl |
| BDA(Ia) or (Ib) | —O— (8-membered lactam with CH₃) | CF₃ |
| BDB(Ia) or (Ib) | —O— (8-membered lactam with CH₃) | CH₃ |
| BDC(Ia) or (Ib) | —N(azetidine)O— | H |
| BDD(Ia) or (Ib) | —N(azetidine)O— | NO₂ |
| BDE(Ia) or (Ib) | —N(azetidine)O— | CN |
| BDF(Ia) or (Ib) | —N(azetidine)O— | F |
| BDG(Ia) or (Ib) | —N(azetidine)O— | Cl |

TABLE 2-continued

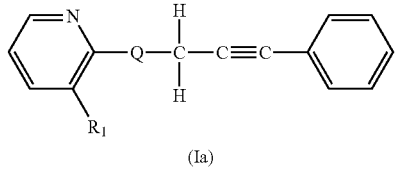

(Ia)

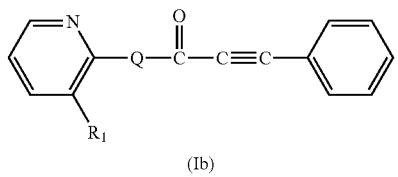

(Ib)

and pharmaceutically acceptable salts thereof, where

| Compound | Q | R₁ |
|---|---|---|
| BDH(Ia) or (Ib) | —N(azetidine)O— | CF₃ |
| BDI(Ia) or (Ib) | —N(azetidine)O— | CH₃ |
| BDJ(Ia) or (Ib) | —N(2-Me-azetidine)O— | H |
| BDK(Ia) or (Ib) | —N(2-Me-azetidine)O— | NO₂ |
| BDL(Ia) or (Ib) | —N(2-Me-azetidine)O— | CN |
| BDM(Ia) or (Ib) | —N(2-Me-azetidine)O— | F |
| BDN(Ia) or (Ib) | —N(2-Me-azetidine)O— | Cl |
| BDO(Ia) or (Ib) | —N(2-Me-azetidine)O— | CF₃ |
| BDP(Ia) or (Ib) | —N(2-Me-azetidine)O— | CH₃ |

TABLE 2-continued

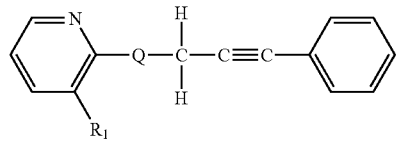

(Ia)

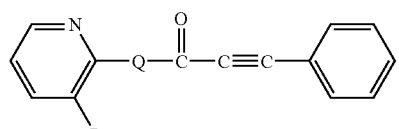

(Ib)

and pharmaceutically acceptable salts thereof, where

| Compound | Q | R₁ |
|---|---|---|
| BDQ(Ia) or (Ib) | 2,4-dimethyl-3-methoxyazetidine | H |
| BDR(Ia) or (Ib) | 2,4-dimethyl-3-methoxyazetidine | NO₂ |
| BDS(Ia) or (Ib) | 2,4-dimethyl-3-methoxyazetidine | CN |
| BDT(Ia) or (Ib) | 2,4-dimethyl-3-methoxyazetidine | F |
| BDU(Ia) or (Ib) | 2,4-dimethyl-3-methoxyazetidine | Cl |
| BDV(Ia) or (Ib) | 2,4-dimethyl-3-methoxyazetidine | CF₃ |

TABLE 2-continued

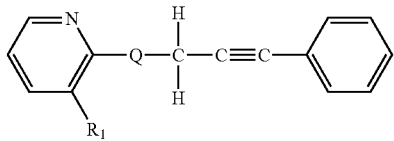

(Ia)

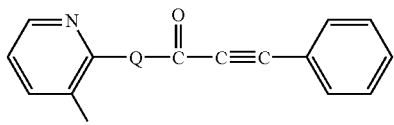

(Ib)

and pharmaceutically acceptable salts thereof, where

| Compound | Q | R₁ |
|---|---|---|
| BDW(Ia) or (Ib) | 2,4-dimethyl-3-methoxyazetidine | CH₃ |
| BDX(Ia) or (Ib) | 3-methoxy-2-oxoazetidine | H |
| BDY(Ia) or (Ib) | 3-methoxy-2-oxoazetidine | NO₂ |
| BDZ(Ia) or (Ib) | 3-methoxy-2-oxoazetidine | CN |
| BEA(Ia) or (Ib) | 3-methoxy-2-oxoazetidine | F |
| BEB(Ia) or (Ib) | 3-methoxy-2-oxoazetidine | Cl |
| BEC(Ia) or (Ib) | 3-methoxy-2-oxoazetidine | CF₃ |
| BED(Ia) or (Ib) | 3-methoxy-2-oxoazetidine | CH₃ |

TABLE 2-continued

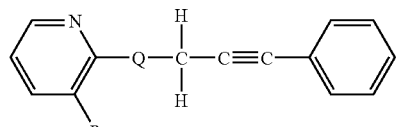

(Ia)

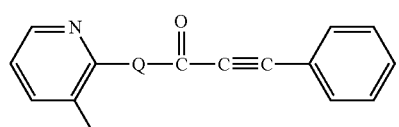

(Ib)

and pharmaceutically acceptable salts thereof, where

| Compound | Q | R₁ |
|---|---|---|
| BEE(Ia) or (Ib) | ![azetidinedione-OMe] | H |
| BEF(Ia) or (Ib) | ![azetidinedione-OMe] | NO₂ |
| BEG(Ia) or (Ib) | ![azetidinedione-OMe] | CN |
| BEH(Ia) or (Ib) | ![azetidinedione-OMe] | F |
| BEI(Ia) or (Ib) | ![azetidinedione-OMe] | Cl |
| BEJ(Ia) or (Ib) | ![azetidinedione-OMe] | CF₃ |

TABLE 2-continued

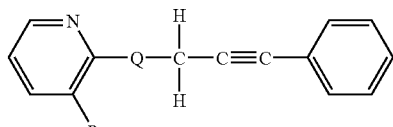

(Ia)

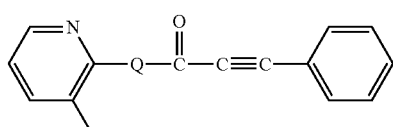

(Ib)

and pharmaceutically acceptable salts thereof, where

| Compound | Q | R₁ |
|---|---|---|
| BEK(Ia) or (Ib) | ![azetidinedione-OMe] | CH₃ |
| BEL(Ia) or (Ib) | ![azetidinone-Me-OMe] | H |
| BEM(Ia) or (Ib) | ![azetidinone-Me-OMe] | NO₂ |
| BEN(Ia) or (Ib) | ![azetidinone-Me-OMe] | CN |
| BEO(Ia) or (Ib) | ![azetidinone-Me-OMe] | F |
| BEP(Ia) or (Ib) | ![azetidinone-Me-OMe] | Cl |

TABLE 2-continued

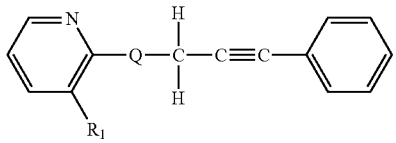

(Ia)

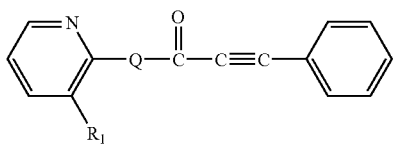

(Ib)

and pharmaceutically acceptable salts thereof, where

| Compound | Q | $R_1$ |
|---|---|---|
| BEQ(Ia) or (Ib) | N-methyl-3-methyl-4-methoxy-azetidin-2-one | $CF_3$ |
| BER(Ia) or (Ib) | N-methyl-3-methyl-4-methoxy-azetidin-2-one | $CH_3$ |
| BES(Ia) or (Ib) | 1-methyl-3-methoxypyrrolidinyl | H |
| BET(Ia) or (Ib) | 1-methyl-3-methoxypyrrolidinyl | $NO_2$ |
| BEU(Ia) or (Ib) | 1-methyl-3-methoxypyrrolidinyl | CN |
| BEV(Ia) or (Ib) | 1-methyl-3-methoxypyrrolidinyl | F |
| BEW(Ia) or (Ib) | 1-methyl-3-methoxypyrrolidinyl | Cl |
| BEX(Ia) or (Ib) | 1-methyl-3-methoxypyrrolidinyl | $CF_3$ |

TABLE 2-continued

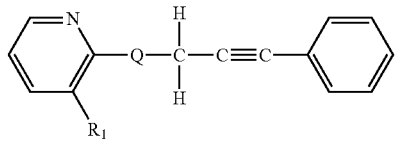

(Ia)

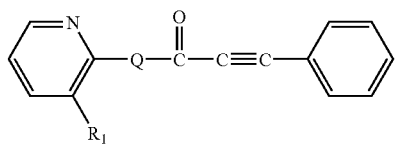

(Ib)

and pharmaceutically acceptable salts thereof, where

| Compound | Q | $R_1$ |
|---|---|---|
| BEY(Ia) or (Ib) | 1-methyl-3-methoxypyrrolidinyl | $CH_3$ |
| BEZ(Ia) or (Ib) | 1-methyl-4-methoxy-pyrrolidin-2-one | H |
| BFA(Ia) or (Ib) | 1-methyl-4-methoxy-pyrrolidin-2-one | $NO_2$ |
| BFB(Ia) or (Ib) | 1-methyl-4-methoxy-pyrrolidin-2-one | CN |
| BFC(Ia) or (Ib) | 1-methyl-4-methoxy-pyrrolidin-2-one | F |
| BFD(Ia) or (Ib) | 1-methyl-4-methoxy-pyrrolidin-2-one | Cl |
| BFE(Ia) or (Ib) | 1-methyl-4-methoxy-pyrrolidin-2-one | $CF_3$ |

TABLE 2-continued

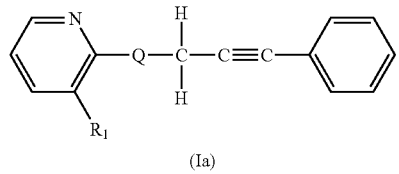

(Ia)

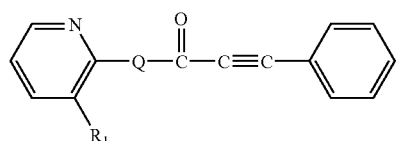

(Ib)

and pharmaceutically acceptable salts thereof, where

| Compound | Q | R₁ |
|---|---|---|
| BFF(Ia) or (Ib) | 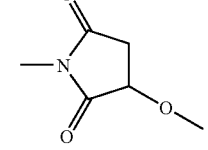 | CH₃ |
| BFG(Ia) or (Ib) | 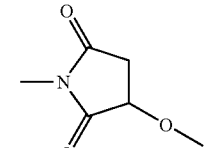 | H |
| BFH(Ia) or (Ib) | 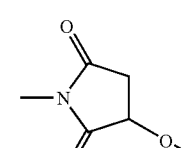 | NO₂ |
| BFI(Ia) or (Ib) | 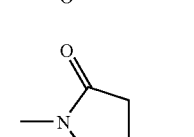 | CN |
| BFJ(Ia) or (Ib) | 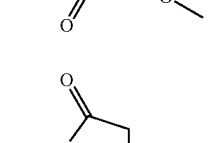 | F |
| BFK(Ia) or (Ib) | 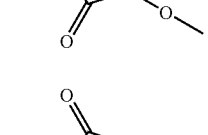 | Cl |
| BFL(Ia) or (Ib) | 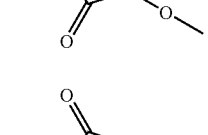 | CF₃ |
| BFM(Ia) or (Ib) | 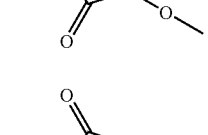 | CH₃ |

TABLE 2-continued

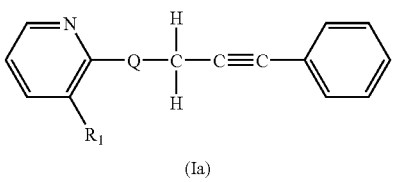

(Ia)

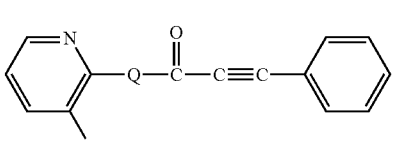

(Ib)

and pharmaceutically acceptable salts thereof, where

| Compound | Q | R₁ |
|---|---|---|
| BFN(Ia) or (Ib) | 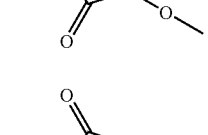 | H |
| BFO(Ia) or (Ib) | 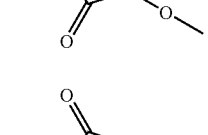 | NO₂ |
| BFP(Ia) or (Ib) | 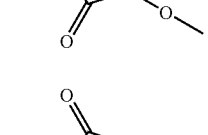 | CN |
| BFQ(Ia) or (Ib) | 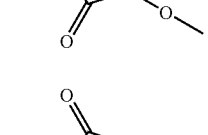 | F |
| BFR(Ia) or (Ib) | 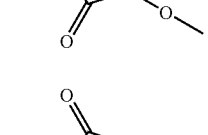 | Cl |
| BFS(Ia) or (Ib) | 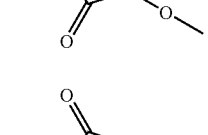 | CF₃ |

TABLE 2-continued

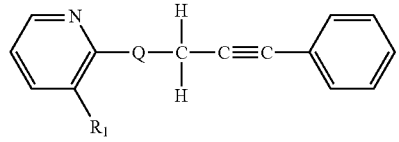
(Ia)

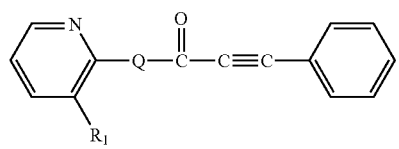
(Ib)

and pharmaceutically acceptable salts thereof, where

| Compound | Q | R₁ |
|---|---|---|
| BFT(Ia) or (Ib) | 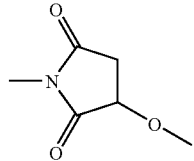 | CH₃ |
| BFU(Ia) or (Ib) | 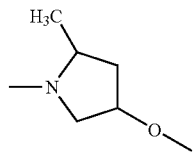 | H |
| BFV(Ia) or (Ib) | 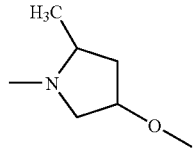 | NO₂ |
| BFW(Ia) or (Ib) | 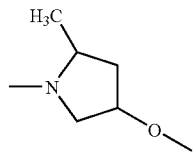 | CN |
| BFX(Ia) or (Ib) | 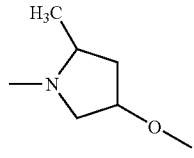 | F |
| BFY(Ia) or (Ib) | 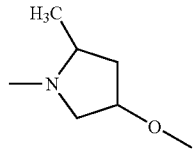 | Cl |
| BFZ(Ia) or (Ib) | 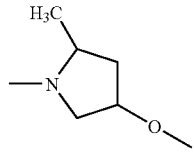 | CF₃ |

TABLE 2-continued

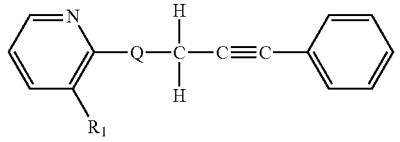
(Ia)

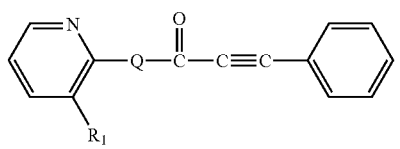
(Ib)

and pharmaceutically acceptable salts thereof, where

| Compound | Q | R₁ |
|---|---|---|
| BGA(Ia) or (Ib) | 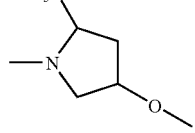 | CH₃ |
| BGB(Ia) or (Ib) | 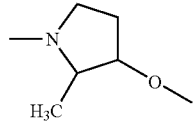 | H |
| BGC(Ia) or (Ib) | 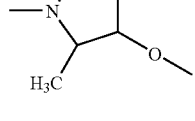 | NO₂ |
| BGD(Ia) or (Ib) | 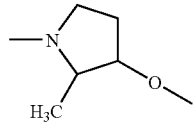 | CN |
| BGE(Ia) or (Ib) | 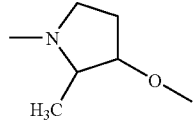 | F |
| BGF(Ia) or (Ib) | 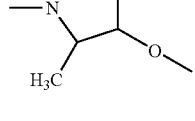 | Cl |
| BGG(Ia) or (Ib) | 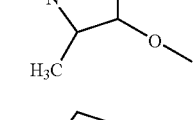 | CF₃ |
| BGH(Ia) or (Ib) | 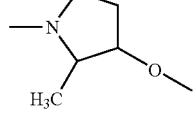 | CH₃ |

TABLE 2-continued

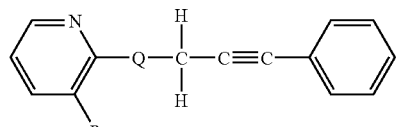
(Ia)

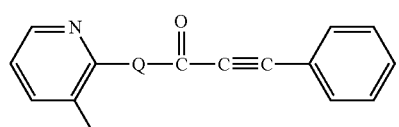
(Ib)

and pharmaceutically acceptable salts thereof, where

| Compound | Q | $R_1$ |
|---|---|---|
| BGI(Ia) or (Ib) | ![pyrrolidine with 2,5-dimethyl and 3-methoxy] | H |
| BGJ(Ia) or (Ib) | ![pyrrolidine with 2,5-dimethyl and 3-methoxy] | $NO_2$ |
| BGK(Ia) or (Ib) | ![pyrrolidine with 2,5-dimethyl and 3-methoxy] | CN |
| BGL(Ia) or (Ib) | ![pyrrolidine with 2,5-dimethyl and 3-methoxy] | F |
| BGM(Ia) or (Ib) | ![pyrrolidine with 2,5-dimethyl and 3-methoxy] | Cl |
| BGN(Ia) or (Ib) | ![pyrrolidine with 2,5-dimethyl and 3-methoxy] | $CF_3$ |

TABLE 2-continued

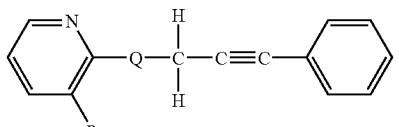
(Ia)

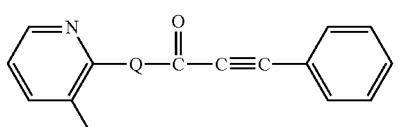
(Ib)

and pharmaceutically acceptable salts thereof, where

| Compound | Q | $R_1$ |
|---|---|---|
| BGO(Ia) or (Ib) | ![pyrrolidine with 2,5-dimethyl and 3-methoxy] | $CH_3$ |
| BGP(Ia) or (Ib) | ![pyrrolidinone with methyl and methoxy] | H |
| BGQ(Ia) or (Ib) | ![pyrrolidinone with methyl and methoxy] | $NO_2$ |
| BGR(Ia) or (Ib) | ![pyrrolidinone with methyl and methoxy] | CN |
| BGS(Ia) or (Ib) | ![pyrrolidinone with methyl and methoxy] | F |
| BGT(Ia) or (Ib) | ![pyrrolidinone with methyl and methoxy] | Cl |

TABLE 2-continued

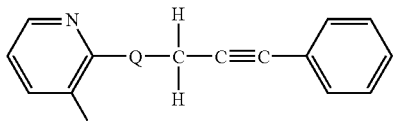

(Ia)

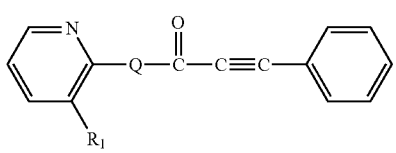

(Ib)

and pharmaceutically acceptable salts thereof, where

| Compound | Q | R$_1$ |
|---|---|---|
| BGU(Ia) or (Ib) | ![pyrrolidinone with CH3 and OMe] | CF$_3$ |
| BGV(Ia) or (Ib) | ![pyrrolidinone with CH3 and OMe] | CH$_3$ |
| BGW(Ia) or (Ib) | ![pyrrolidinone with H3C and OMe] | H |
| BGX(Ia) or (Ib) | ![pyrrolidinone with H3C and OMe] | NO$_2$ |
| BGY(Ia) or (Ib) | ![pyrrolidinone with H3C and OMe] | CN |
| BGZ(Ia) or (Ib) | ![pyrrolidinone with H3C and OMe] | F |

TABLE 2-continued

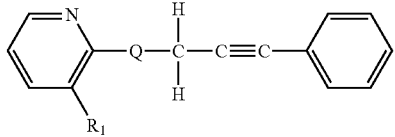

(Ia)

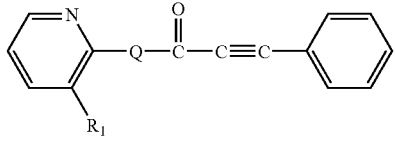

(Ib)

and pharmaceutically acceptable salts thereof, where

| Compound | Q | R$_1$ |
|---|---|---|
| BHA(Ia) or (Ib) | ![pyrrolidinone with H3C and OMe] | Cl |
| BHB(Ia) or (Ib) | ![pyrrolidinone with H3C and OMe] | CF$_3$ |
| BHC(Ia) or (Ib) | ![pyrrolidinone with H3C and OMe] | CH$_3$ |
| BHD(Ia) or (Ib) | ![piperidine with OMe] | H |
| BHE(Ia) or (Ib) | ![piperidine with OMe] | NO$_2$ |
| BHF(Ia) or (Ib) | ![piperidine with OMe] | CN |
| BHG(Ia) or (Ib) | ![piperidine with OMe] | F |
| BHH(Ia) or (Ib) | ![piperidine with OMe] | Cl |
| BHI(Ia) or (Ib) | ![piperidine with OMe] | CF$_3$ |

TABLE 2-continued

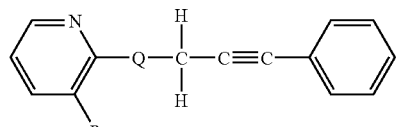

(Ia)

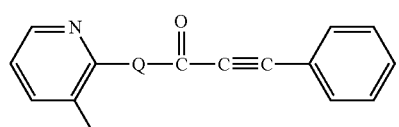

(Ib)

and pharmaceutically acceptable salts thereof, where

| Compound | Q | $R_1$ |
|---|---|---|
| BHJ(Ia) or (Ib) | 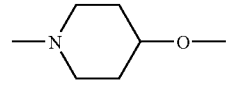 | $CH_3$ |
| BHK(Ia) or (Ib) | 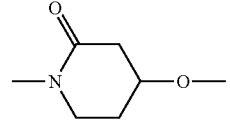 | H |
| BHL(Ia) or (Ib) | 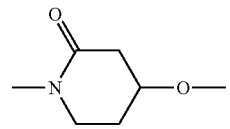 | $NO_2$ |
| BHM(Ia) or (Ib) | 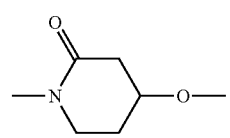 | CN |
| BHN(Ia) or (Ib) | 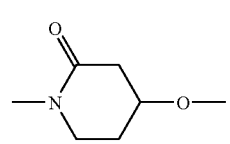 | F |
| BHO(Ia) or (Ib) | 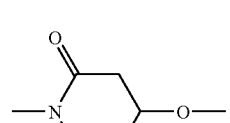 | Cl |
| BHP(Ia) or (Ib) | 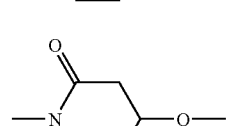 | $CF_3$ |
| BHQ(Ia) or (Ib) | 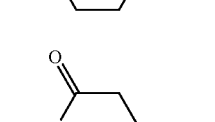 | $CH_3$ |

TABLE 2-continued

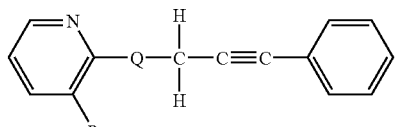

(Ia)

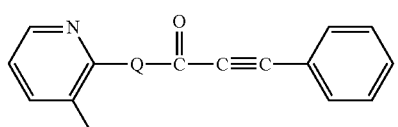

(Ib)

and pharmaceutically acceptable salts thereof, where

| Compound | Q | $R_1$ |
|---|---|---|
| BHR(Ia) or (Ib) | 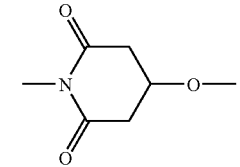 | H |
| BHS(Ia) or (Ib) | 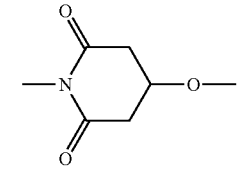 | $NO_2$ |
| BHT(Ia) or (Ib) | 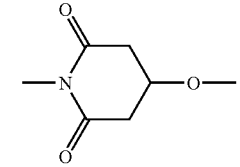 | CN |
| BHU(Ia) or (Ib) | 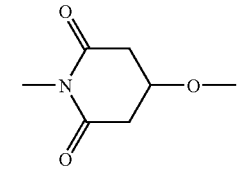 | F |
| BHV(Ia) or (Ib) | 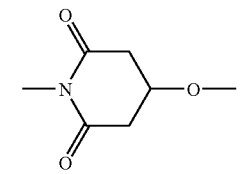 | Cl |
| BHW(Ia) or (Ib) | 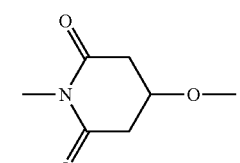 | $CF_3$ |

TABLE 2-continued

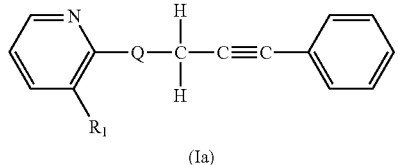

(Ia)

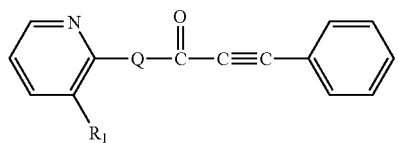

(Ib)

and pharmaceutically acceptable salts thereof, where

| Compound | Q | R₁ |
|---|---|---|
| BHX(Ia) or (Ib) | 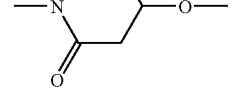 | $CH_3$ |
| BHY(Ia) or (Ib) | 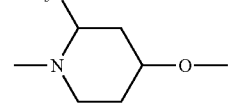 | H |
| BHZ(Ia) or (Ib) | 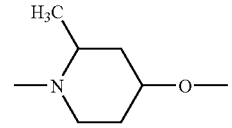 | $NO_2$ |
| BIA(Ia) or (Ib) | 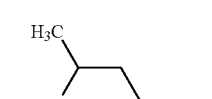 | CN |
| BIB(Ia) or (Ib) | 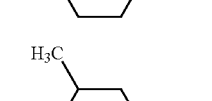 | F |
| BIC(Ia) or (Ib) | 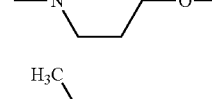 | Cl |
| BID(Ia) or (Ib) | 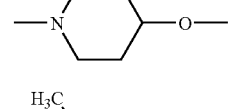 | $CF_3$ |
| BIE(Ia) or (Ib) | 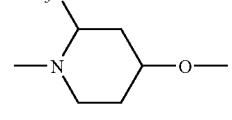 | $CH_3$ |

TABLE 2-continued

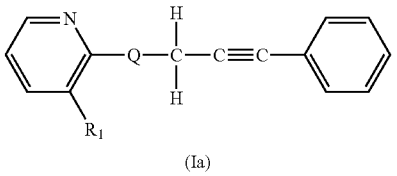

(Ia)

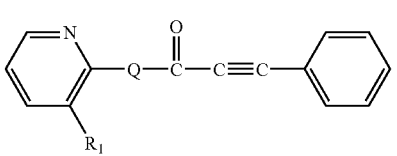

(Ib)

and pharmaceutically acceptable salts thereof, where

| Compound | Q | R₁ |
|---|---|---|
| BIF(Ia) or (Ib) | 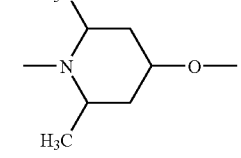 | H |
| BIG(Ia) or (Ib) | 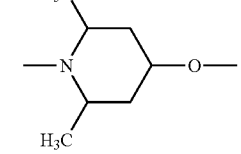 | $NO_2$ |
| BIH(Ia) or (Ib) | 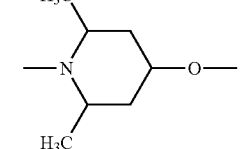 | CN |
| BII(Ia) or (Ib) | 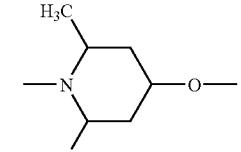 | F |
| BIJ(Ia) or (Ib) | 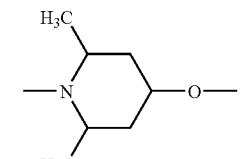 | Cl |
| BIK(Ia) or (Ib) | 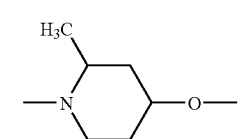 | $CF_3$ |

TABLE 2-continued

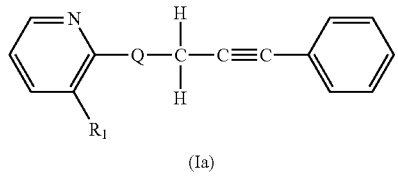

(Ia)

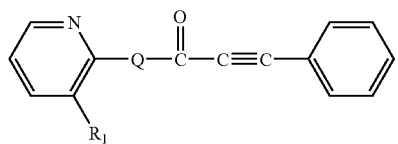

(Ib)

and pharmaceutically acceptable salts thereof, where

| Compound | Q | R₁ |
|---|---|---|
| BIL(Ia) or (Ib) | H₃C–[N-piperidine with 2,6-diMe, 4-OMe]– | CH₃ |
| BLM(Ia) or (Ib) | [N-methyl-6-methyl-2-oxo-4-methoxypiperidine] | H |
| BIN(Ia) or (Ib) | [N-methyl-6-methyl-2-oxo-4-methoxypiperidine] | NO₂ |
| BIO(Ia) or (Ib) | [N-methyl-6-methyl-2-oxo-4-methoxypiperidine] | CN |
| BIP(Ia) or (Ib) | [N-methyl-6-methyl-2-oxo-4-methoxypiperidine] | F |
| BIQ(Ia) or (Ib) | [N-methyl-6-methyl-2-oxo-4-methoxypiperidine] | Cl |

TABLE 2-continued

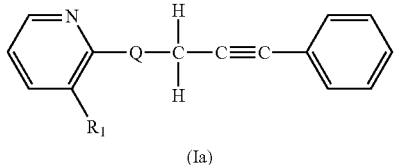

(Ia)

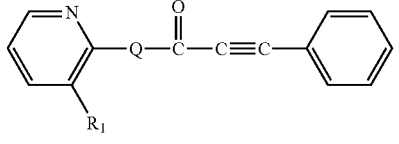

(Ib)

and pharmaceutically acceptable salts thereof, where

| Compound | Q | R₁ |
|---|---|---|
| BIR(Ia) or (Ib) | [N-methyl-6-methyl-2-oxo-4-methoxypiperidine] | CF₃ |
| BIS(Ia) or (Ib) | [N-methyl-6-methyl-2-oxo-4-methoxypiperidine] | CH₃ |
| BIT(Ia) or (Ib) | [N-methyl-4-methoxyazepane] | H |
| BIU(Ia) or (Ib) | [N-methyl-4-methoxyazepane] | NO₂ |
| BIV(Ia) or (Ib) | [N-methyl-4-methoxyazepane] | CN |
| BIW(Ia) or (Ib) | [N-methyl-4-methoxyazepane] | F |
| BIX(Ia) or (Ib) | [N-methyl-4-methoxyazepane] | Cl |
| BIY(Ia) or (Ib) | [N-methyl-4-methoxyazepane] | CF₃ |

TABLE 2-continued

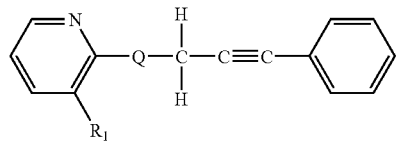

(Ia)

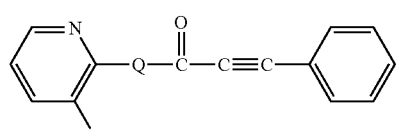

(Ib)

and pharmaceutically acceptable salts thereof, where

| Compound | Q | $R_1$ |
|---|---|---|
| BIZ(Ia) or (Ib) | N-methyl methoxy azepane | $CH_3$ |
| BJA(Ia) or (Ib) | N-methyl methoxy caprolactam | H |
| BJB(Ia) or (Ib) | N-methyl methoxy caprolactam | $NO_2$ |
| BJC(Ia) or (Ib) | N-methyl methoxy caprolactam | CN |
| BJD(Ia) or (Ib) | N-methyl methoxy caprolactam | F |
| BJE(Ia) or (Ib) | N-methyl methoxy caprolactam | Cl |
| BJF(Ia) or (Ib) | N-methyl methoxy caprolactam | $CF_3$ |

TABLE 2-continued

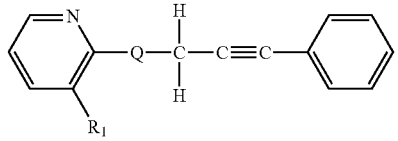

(Ia)

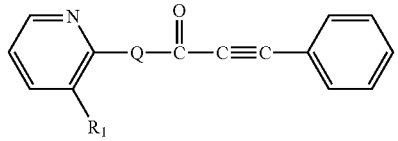

(Ib)

and pharmaceutically acceptable salts thereof, where

| Compound | Q | $R_1$ |
|---|---|---|
| BJG(Ia) or (Ib) | N-methyl methoxy caprolactam | $CH_3$ |
| BJH(Ia) or (Ib) | N-methyl methoxy caprolactam | H |
| BJI(Ia) or (Ib) | N-methyl methoxy caprolactam | $NO_2$ |
| BJJ(Ia) or (Ib) | N-methyl methoxy caprolactam | CN |
| BJK(Ia) or (Ib) | N-methyl methoxy caprolactam | F |
| BJL(Ia) or (Ib) | N-methyl methoxy caprolactam | Cl |
| BJM(Ia) or (Ib) | N-methyl methoxy caprolactam | $CF_3$ |

TABLE 2-continued

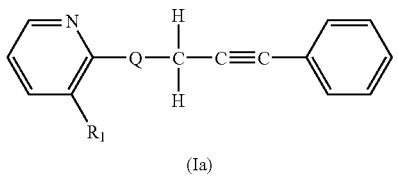

(Ia)

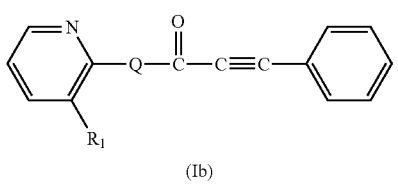

(Ib)

and pharmaceutically acceptable salts thereof, where

| Compound | Q | R₁ |
|---|---|---|
| BJN(Ia) or (Ib) | 4-methoxy-1-methyl-azepan-2-one (N-linked) | CH₃ |
| BJO(Ia) or (Ib) | 4-methoxy-1-methyl-azepane-2,7-dione (N-linked) | H |
| BJP(Ia) or (Ib) | 4-methoxy-1-methyl-azepane-2,7-dione (N-linked) | NO₂ |
| BJQ(Ia) or (Ib) | 4-methoxy-1-methyl-azepane-2,7-dione (N-linked) | CN |
| BJR(Ia) or (Ib) | 4-methoxy-1-methyl-azepane-2,7-dione (N-linked) | F |
| BJS(Ia) or (Ib) | 4-methoxy-1-methyl-azepane-2,7-dione (N-linked) | Cl |

TABLE 2-continued

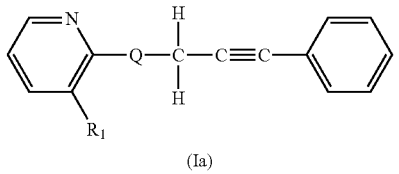

(Ia)

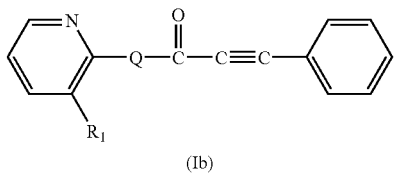

(Ib)

and pharmaceutically acceptable salts thereof, where

| Compound | Q | R₁ |
|---|---|---|
| BJT(Ia) or (Ib) | 4-methoxy-1-methyl-azepane-2,7-dione (N-linked) | CF₃ |
| BJU(Ia) or (Ib) | 4-methoxy-1-methyl-azepane-2,7-dione (N-linked) | CH₃ |
| BJV(Ia) or (Ib) | 4-methoxy-2-methyl-azepane (N-linked) | H |
| BJW(Ia) or (Ib) | 4-methoxy-2-methyl-azepane (N-linked) | NO₂ |
| BJX(Ia) or (Ib) | 4-methoxy-2-methyl-azepane (N-linked) | CN |
| BJY(Ia) or (Ib) | 4-methoxy-2-methyl-azepane (N-linked) | F |
| BJZ(Ia) or (Ib) | 4-methoxy-2-methyl-azepane (N-linked) | Cl |

TABLE 2-continued

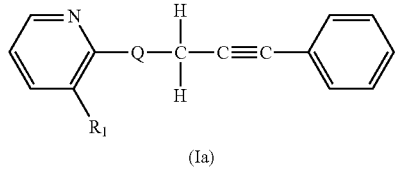

(Ia)

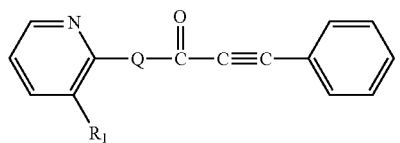

(Ib)

and pharmaceutically acceptable salts thereof, where

| Compound | Q | R₁ |
|---|---|---|
| BKA(Ia) or (Ib) | 2-methyl-5-methoxy-azepan-1-yl | CF₃ |
| BKB(Ia) or (Ib) | 2-methyl-5-methoxy-azepan-1-yl | CH₃ |
| BKC(Ia) or (Ib) | 2-methyl-5-methoxy-azepan-1-yl | H |
| BKD(Ia) or (Ib) | 2-methyl-5-methoxy-azepan-1-yl | NO₂ |
| BKE(Ia) or (Ib) | 2-methyl-5-methoxy-azepan-1-yl | CN |
| BKF(Ia) or (Ib) | 2-methyl-5-methoxy-azepan-1-yl | F |
| BKG(Ia) or (Ib) | 2-methyl-5-methoxy-azepan-1-yl | Cl |

TABLE 2-continued

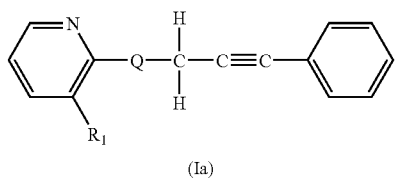

(Ia)

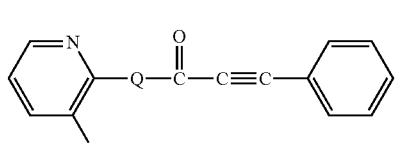

(Ib)

and pharmaceutically acceptable salts thereof, where

| Compound | Q | R₁ |
|---|---|---|
| BKH(Ia) or (Ib) | 2-methyl-5-methoxy-azepan-1-yl | CF₃ |
| BKI(Ia) or (Ib) | 2-methyl-5-methoxy-azepan-1-yl | CH₃ |
| BKJ(Ia) or (Ib) | 2,7-dimethyl-5-methoxy-azepan-1-yl | H |
| BKK(Ia) or (Ib) | 2,7-dimethyl-5-methoxy-azepan-1-yl | NO₂ |
| BKL(Ia) or (Ib) | 2,7-dimethyl-5-methoxy-azepan-1-yl | CN |
| BKM(Ia) or (Ib) | 2,7-dimethyl-5-methoxy-azepan-1-yl | F |

TABLE 2-continued

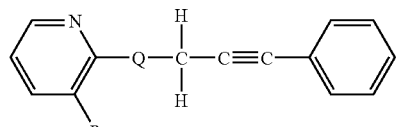

(Ia)

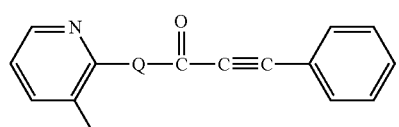

(Ib)

and pharmaceutically acceptable salts thereof, where

| Compound | Q | R₁ |
|---|---|---|
| BKN(Ia) or (Ib) | H₃C, N(CH₃), OCH₃ (methyl-substituted azepane with methoxy) | Cl |
| BKO(Ia) or (Ib) | H₃C, N, CH₃, OCH₃ azepane | CF₃ |
| BKP(Ia) or (Ib) | H₃C, N, CH₃, OCH₃ azepane | CH₃ |
| BKQ(Ia) or (Ib) | O=, N, CH₃, OCH₃ caprolactam | H |
| BKR(Ia) or (Ib) | O=, N, CH₃, OCH₃ caprolactam | NO₂ |
| BKS(Ia) or (Ib) | O=, N, CH₃, OCH₃ caprolactam | CN |

TABLE 2-continued

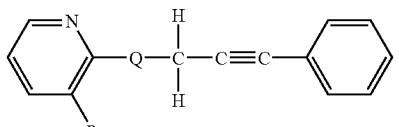

(Ia)

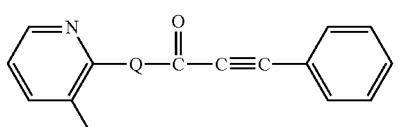

(Ib)

and pharmaceutically acceptable salts thereof, where

| Compound | Q | R₁ |
|---|---|---|
| BKT(Ia) or (Ib) | O=, N, CH₃, OCH₃ caprolactam | F |
| BKU(Ia) or (Ib) | O=, N, CH₃, OCH₃ caprolactam | Cl |
| BKV(Ia) or (Ib) | O=, N, CH₃, OCH₃ caprolactam | CF₃ |
| BKW(Ia) or (Ib) | O=, N, CH₃, OCH₃ caprolactam | CH₃ |
| BKX(Ia) or (Ib) | H₃C, N, OCH₃, O= caprolactam | H |
| BKY(Ia) or (Ib) | H₃C, N, OCH₃, O= caprolactam | NO₂ |

TABLE 2-continued

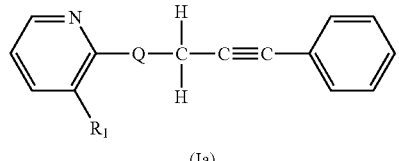

(Ia)

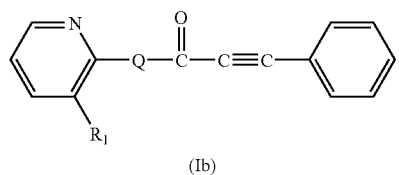

(Ib)

and pharmaceutically acceptable salts thereof, where

| Compound | Q | $R_1$ |
| --- | --- | --- |
| BKZ(Ia) or (Ib) | ![H3C-substituted methoxy-azepanone] | CN |
| BLA(Ia) or (Ib) | ![H3C-substituted methoxy-azepanone] | F |
| BLB(Ia) or (Ib) | ![H3C-substituted methoxy-azepanone] | Cl |
| BLC(Ia) or (Ib) | ![H3C-substituted methoxy-azepanone] | $CF_3$ |
| BLD(Ia) or (Ib) | ![H3C-substituted methoxy-azepanone] | $CH_3$ |
| BLE(Ia) or (Ib) | ![methoxy-azocane] | H |
| BLF(Ia) or (Ib) | ![methoxy-azocane] | $NO_2$ |

TABLE 2-continued

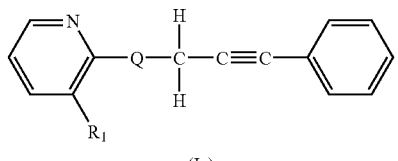

(Ia)

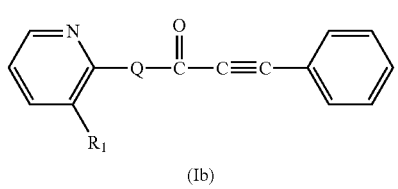

(Ib)

and pharmaceutically acceptable salts thereof, where

| Compound | Q | $R_1$ |
| --- | --- | --- |
| BLG(Ia) or (Ib) | ![methoxy-azocane] | CN |
| BLH(Ia) or (Ib) | ![methoxy-azocane] | F |
| BLI(Ia) or (Ib) | ![methoxy-azocane] | Cl |
| BLJ(Ia) or (Ib) | ![methoxy-azocane] | $CF_3$ |
| BLK(Ia) or (Ib) | ![methoxy-azocane] | $CH_3$ |
| BLL(Ia) or (Ib) | ![methoxy-azocanone] | H |
| BLM(Ia) or (Ib) | ![methoxy-azocanone] | $NO_2$ |
| BLN(Ia) or (Ib) | ![methoxy-azocanone] | CN |

TABLE 2-continued

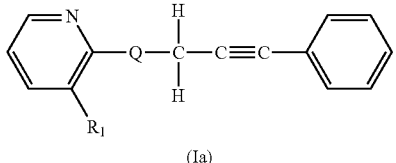

(Ia)

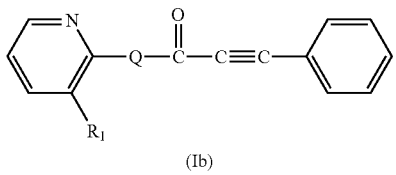

(Ib)

and pharmaceutically acceptable salts thereof, where

| Compound | Q | R₁ |
|---|---|---|
| BLO(Ia) or (Ib) | ![structure] | F |
| BLP(Ia) or (Ib) | ![structure] | Cl |
| BLQ(Ia) or (Ib) | ![structure] | $CF_3$ |
| BLR(Ia) or (Ib) | ![structure] | $CH_3$ |
| BLS(Ia) or (Ib) | ![structure] | H |
| BLT(Ia) or (Ib) | ![structure] | $NO_2$ |
| BLU(Ia) or (Ib) | ![structure] | CN |

TABLE 2-continued

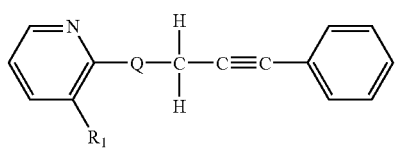

(Ia)

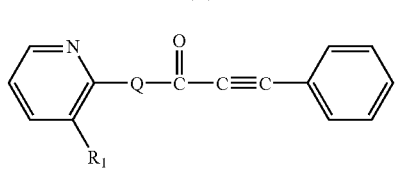

(Ib)

and pharmaceutically acceptable salts thereof, where

| Compound | Q | R₁ |
|---|---|---|
| BLV(Ia) or (Ib) | ![structure] | F |
| BLW(Ia) or (Ib) | ![structure] | Cl |
| BLX(Ia) or (Ib) | ![structure] | $CF_3$ |
| BLY(Ia) or (Ib) | ![structure] | $CH_3$ |
| BLZ(Ia) or (Ib) | ![structure] | H |
| BMA(Ia) or (Ib) | ![structure] | $NO_2$ |

TABLE 2-continued

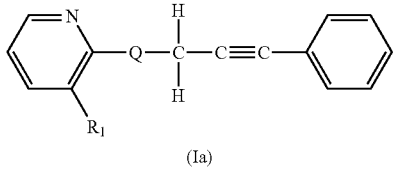

(Ia)

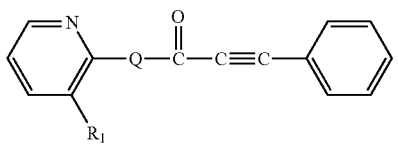

(Ib)

and pharmaceutically acceptable salts thereof, where

| Compound | Q | R₁ |
|---|---|---|
| BMB(Ia) or (Ib) | H₃C-[azocane-N,O] | CN |
| BMC(Ia) or (Ib) | H₃C-[azocane-N,O] | F |
| BMD(Ia) or (Ib) | H₃C-[azocane-N,O] | Cl |
| BME(Ia) or (Ib) | H₃C-[azocane-N,O] | CF₃ |
| BMF(Ia) or (Ib) | H₃C-[azocane-N,O] | CH₃ |
| BMG(Ia) or (Ib) | H₃C-[azocane-N,O]-CH₃ | H |
| BMH(Ia) or (Ib) | H₃C-[azocane-N,O]-CH₃ | NO₂ |

TABLE 2-continued

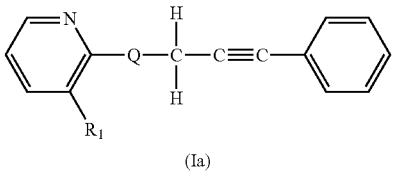

(Ia)

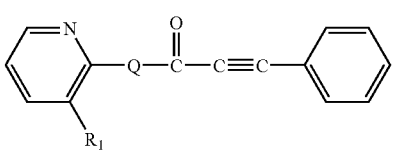

(Ib)

and pharmaceutically acceptable salts thereof, where

| Compound | Q | R₁ |
|---|---|---|
| BMI(Ia) or (Ib) | H₃C-[azocane-N,O]-CH₃ | CN |
| BMJ(Ia) or (Ib) | H₃C-[azocane-N,O]-CH₃ | F |
| BMK(Ia) or (Ib) | H₃C-[azocane-N,O]-CH₃ | Cl |
| BML(Ia) or (Ib) | H₃C-[azocane-N,O]-CH₃ | CF₃ |
| BMM(Ia) or (Ib) | H₃C-[azocane-N,O]-CH₃ | CH₃ |
| BMN(Ia) or (Ib) | O=[azocane-N,O]-CH₃ | H |

TABLE 2-continued

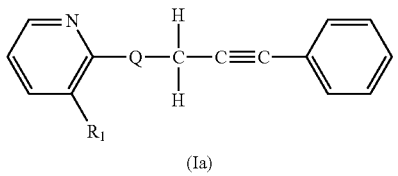

(Ia)

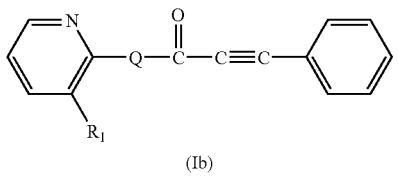

(Ib)

and pharmaceutically acceptable salts thereof, where

| Compound | Q | $R_1$ |
|---|---|---|
| BMO(Ia) or (Ib) | ![N-acetyl-azepanone with O linker, H3C substituent] | $NO_2$ |
| BMP(Ia) or (Ib) | ![same core] | CN |
| BMQ(Ia) or (Ib) | ![same core] | F |
| BMR(Ia) or (Ib) | ![same core] | Cl |
| BMS(Ia) or (Ib) | ![same core] | $CF_3$ |
| BMT(Ia) or (Ib) | ![same core] | $CH_3$ |

In another embodiment, for each of the Compounds AAA (Ia) or AAA(Ib) through BMT(Ia) or BMT(Ib) above, the compound's phenyl group is substituted at the phenyl group's 4-position with F.

In another embodiment, for each of the Compounds AAA (Ia) or AAA(Ib) through BMT(Ia) or BMT(Ib) above, the compound's phenyl group is substituted at the phenyl group's 4-position with Cl.

In another embodiment, each of the Compounds AAA(Ia) or AAA(Ib) through BMT(Ia) or BMT(Ib) above, the compound's phenyl group is substituted at the phenyl group's 4-position with I.

In another embodiment, each of the Compounds AAA(Ia) or AAA(Ib) through BMT(Ia) or BMT(Ib) above, the compound's phenyl group is substituted at the phenyl group's 4-position with Br.

In another embodiment, each of the Compounds AAA(Ia) or AAA(Ib) through BMT(Ia) or BMT(Ib) above, the compound's phenyl group is substituted at the phenyl group's 4-position with $CH_3$.

In another embodiment, each of the Compounds AAA(Ia) or AAA(Ib) through BMT(Ia) or BMT(Ib) above, the compound's phenyl group is substituted at the phenyl group's 4-position with $CF_3$.

In another embodiment, each of the Compounds AAA(Ia) or AAA(Ib) through BMT(Ia) or BMT(Ib) above, the compound's phenyl group is substituted at the phenyl group's 4-position with $OCH_3$.

In another embodiment, each of the Compounds AAA(Ia) or AAA(Ib) through BMT(Ia) or BMT(Ib) above, the compound's phenyl group is substituted at the phenyl group's 4-position with $OCF_3$.

In another embodiment, each of the Compounds AAA(Ia) or AAA(Ib) through BMT(Ia) or BMT(Ib) above, the compound's phenyl group is substituted at the phenyl group's 4-position with ethyl.

In another embodiment, each of the Compounds AAA(Ia) or AAA(Ib) through BMT(Ia) or BMT(Ib) above, the compound's phenyl group is substituted at the phenyl group's 4-position with isopropyl.

In another embodiment, each of the Compounds AAA(Ia) or AAA(Ib) through BMT(Ia) or BMT(Ib) above, the compound's phenyl group is substituted at the phenyl group's 4-position with tert-butyl.

4.1 Definitions

As used herein, in connection with Pyridine-alkynyl Compounds, the terms used above having following meaning:

"—$(C_1-C_6)$alkyl" means a saturated straight chain or branched non-cyclic hydrocarbon having from 1 to 6 carbon atoms. Representative saturated straight chain —$(C_1-C_6)$ alkyls include -methyl, -ethyl, -n-propyl, -n-butyl, -n-pentyl, and -n-hexyl. Representative saturated branched —$(C_1-C_6)$ alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl and the like.

"—$(C_1-C_6)$alkoxy" means —$O(C_1-C_6)$alkyl, wherein —$(C_1-C_6)$alkyl is defined above.

"—$(C_1-C_4)$alkyl" means a saturated straight chain or branched non-cyclic hydrocarbon having from 1 to 4 carbon atoms. Representative saturated straight chain —$(C_1-C_4)$ alkyls include -methyl, -ethyl, -n-propyl, and -n-butyl. Representative saturated branched —$(C_1-C_4)$alkyls include -isopropyl, -sec-butyl, -isobutyl, and -tert-butyl.

"—($C_3$-$C_8$)cycloalkyl" means a saturated cyclic hydrocarbon having from 3 to 8 carbon atoms. Representative —($C_3$-$C_8$)cycloalkyls include -cyclopropyl, -cyclobutyl, -cyclopentyl, -cyclohexyl, -cycloheptyl, and -cyclooctyl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative (5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"-(3- to 7-membered)heterocycle" or "-(3- to 7-membered) heterocyclo" means a 3- to 7-membered monocyclic heterocyclic ring which is either saturated, unsaturated non-aromatic or aromatic. A 3- or a 4-membered heterocycle can contain up to 3 heteroatoms, a 5-membered heterocycle can contain up to 4 heteroatoms, a 6-membered heterocycle can contain up to 6 heteroatoms, and a 7-membered heterocycle can contain up to 7 heteroatoms. Each heteroatom is independently selected from nitrogen, which can be quaternized; oxygen; and sulfur, including sulfoxide and sulfone. The -(3- to 7-membered)heterocycle can be attached via any heteroatom or carbon atom. Representative -(3- to 7-membered) heterocycles include pyridyl, furyl, thiophenyl, pyrrolyl, oxazolyl, imidazolyl, thiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(7- to 10-membered) bicycloheterocycle" or "-(7- to 10-membered) bicycloheterocyclo" means a 7- to 10-membered bicyclic, heterocyclic ring which is either saturated, unsaturated non-aromatic or aromatic. A -(7- to 10-membered) bicycloheterocycle contains from 1 to 4 heteroatoms independently selected from nitrogen, which can be quaternized; oxygen; and sulfur, including sulfoxide and sulfone. The -(7- to 10-membered) bicycloheterocycle can be attached via any heteroatom or carbon atom. Representative -(7- to 10-membered) bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -benzothiazolyl, -benzimidazolyl, benzoxazolyl and the like.

"—($C_{14}$)aryl" means a 14-membered aromatic carbocyclic moiety such as anthryl and phenanthryl.

"—C(halo)$_3$" means a methyl group wherein each of the hydrogens of the methyl group has been replaced with a halogen. Representative —C(halo)$_3$ groups include —$CF_3$, —$CCl_3$, —$CBr_3$, —$CI_3$, —$CF_2Cl$, —$CCl_2F$, and —CFClI.

"-Halogen" or "-halo" means —F, —Cl, —Br, or —I.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable salt," as used herein, is any pharmaceutically acceptable salt that can be prepared from a Pyridine-alkynyl Compound, including a salt formed from an acid and a basic functional group, such as a nitrogen group, of one of the Pyridine-alkynyl Compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a Pyridine-alkynyl Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di- or trialkylamines; dicyclohexylamine; tributyl amine; pyridine; N-methyl-N-ethylamine; diethylamine; triethylamine; mono-, bis- or tris-(2-hydroxy-lower alkyl amines), such as mono-, bis- or tris-(2-hydroxyethyl)amine, 2-hydroxy-tert-butylamine or tris-(hydroxymethyl)methylamine, N,N-di-lower alkyl-N-(hydroxy lower alkyl)-amines, such as N,N-dimethyl-N-(2-hydroxyethyl)amine or tri-(2-hydroxyethyl)amine; N-methyl-D-glucamine; and amino acids such as arginine, lysine and the like.

The phrase "effective amount," when used in connection with a Pyridine-alkynyl Compound means an amount effective for: (a) treating or preventing a Condition; or (b) inhibiting mGluR1 or mGluR5 function in a cell.

The phrase "effective amount," when used in connection with another therapeutic agent means an amount for providing the therapeutic effect of the other therapeutic agent.

When a first group is "substituted with one or more" second groups, each of one or more of the first group's hydrogen atoms is replaced with a second group.

The term "UI" means urinary incontinence.

The term "ALS" means amyotrophic lateral sclerosis.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

It is to be understood that in a Q(i) group, the endocyclic nitrogen atom is bonded to the 2-position of the pyridinyl group comprising R. In a Q(ii) group, the exocyclic nitrogen or exocyclic oxygen atom is bonded to the 2-position of the pyridinyl group comprising $R_1$.

4.2 Methods for Making the Pyridine-Alkynyl Compounds

The Pyridine-alkynyl Compounds can be made using conventional organic synthesis and/or by the following illustrative methods.

The Pyridine-alkynyl Compounds of Formula (Ia), where A is —C(O)—, can be made by reacting a compound of formula A with $R_2$—I at room temperature, e.g., about 25° C., in ethyl acetate in the presence of Pd(Ph$_3$P)$_2$(OAc)$_2$, CuI and triethylamine ("TEA"), as shown below in Scheme 1:

Scheme 1

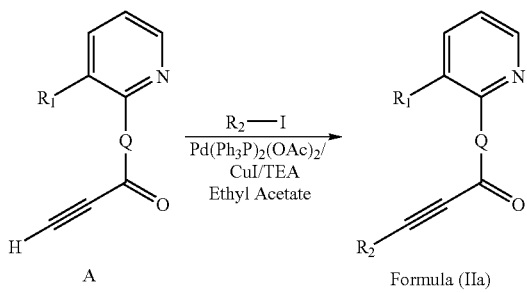

where Q, $R_1$ and $R_2$ are defined above for the compounds of Formula (I). A representative procedure for coupling a terminal acetylene with an $R_2$—I is provided in L. A. Hay et al., *J. Org. Chem.* 5050-5058 (1998).

The Pyridine-alkynyl Compounds of Formula (Ib), comprising a Q(i) group, can be made by reacting a diamine or hydroxylamine compound of formula C with a 2-halopyridine compound at about 100° C. from about 10 to about 20 hours in dimethylsulfoxide ("DMSO") in the presence of TEA followed by reacting the resulting terminal amine with an $R_2$-substituted propiolic acid at about 25° C. for about 1 to about 10 hours in dimethyl formamide ("DMF") in the presence of 1-hydroxybenzotriazole ("HOBt") and 1,3-diisopropyl-carbodiimide ("DIC"), as shown below in Scheme 2:

Scheme 2

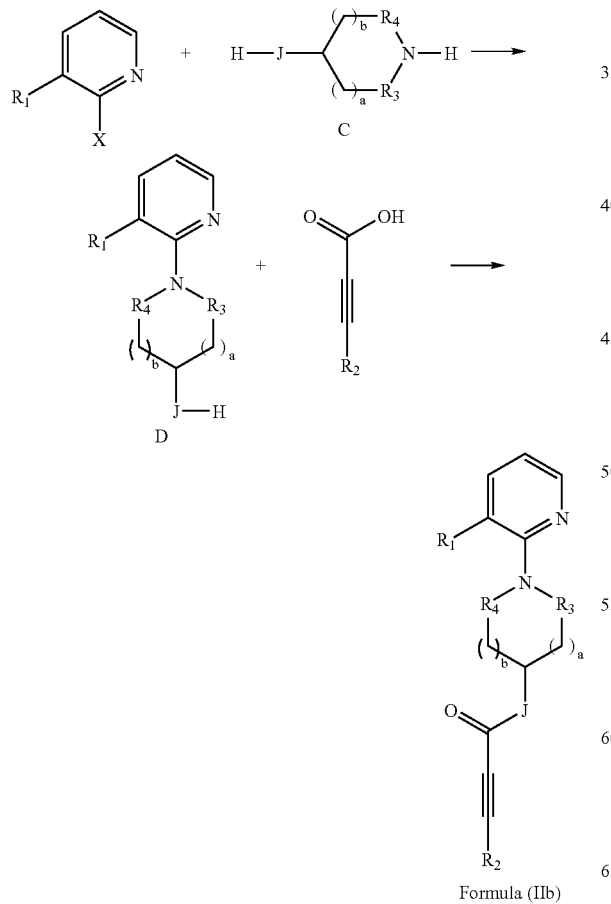

where X is Cl, Br or I, J is N(H) or O, and $R_1$, $R_2$, $R_3$, $R_4$, a and b are defined above for the compounds of Formula (I). A representative procedure for reacting a heterocyclic amine with a 2-halopyridine is provided in S. Sabatini et al., *J. Heterocyclic Chem.* 36:953-957 (1999). A representative procedure for reacting a terminal amine with an $R_2$-substituted propiolic acid is provided in F. M. Martin et al., *Bioorg. Med. Chem. Lett.* 9:2887-2892 (1999). A representative procedure for reacting a terminal hydroxyl with an $R_2$-substituted propiolic acid is provided in K. C. Nicolaou et al., *J. Chem. Soc., Chem. Comm.* 7:421 (1985).

The Pyridine-alkynyl Compounds of Formula (Ic), comprising a Q(ii) group, can be made by first reacting a diamine or hydroxylamine compound of formula E, comprising a protected amine group, with a 2-halopyridine compound at about 100° C. for about 10 to about 20 hours in DMSO in the presence of TEA. The protected amine group can be deprotected by reacting at about 25° C. for about 1 to about 5 hours in dichloromethane ("DCM") in the presence of 20% trifluoroacetic acid ("TFA"). The resulting terminal amine can be reacted with an $R_2$-substituted propiolic acid at about 25° C. for about 1 to about 10 hours in DMF in the presence of HOBt and DIC.

This sequence of reactions is shown below in Scheme 3:

Scheme 3

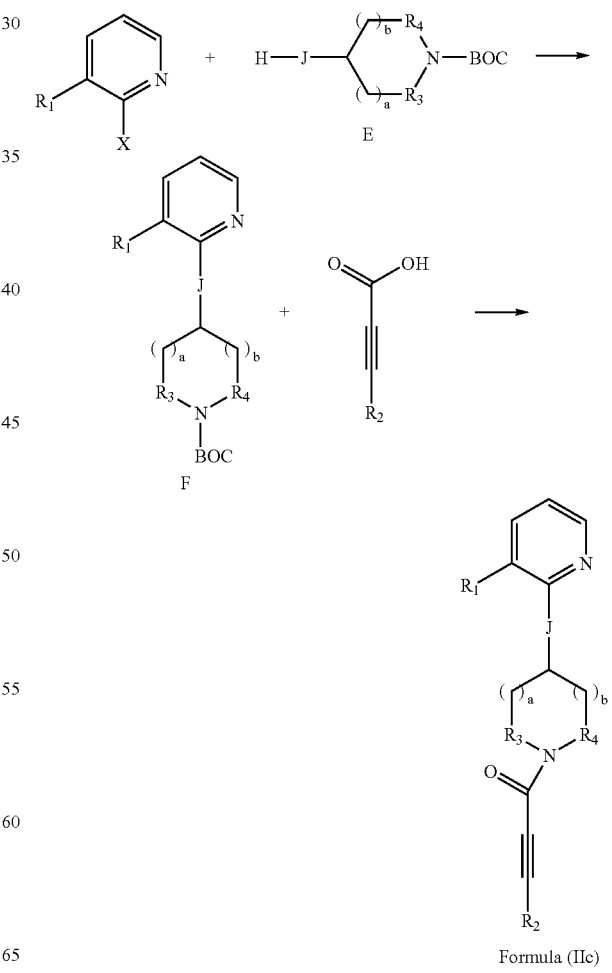

where X is Cl, Br or I, J is N(H) or O, and $R_1$, $R_2$, $R_3$, $R_4$, a and b are defined above for the compounds of Formula (I). A representative procedure for reacting a diamine comprising a blocked amine group with a 2-halopyridine is provided in M. J. Genin et al., *J. Med. Chem.* 42:4140-4149 (1999). A representative procedure for deprotecting an amine is provided in J. P. Sanchez et al., *J. Med. Chem.* 31:983-991 (1988).

The Pyridine-alkynyl Compounds of Formula (Id), i.e.:

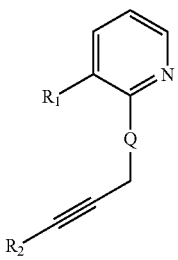

Formula (IId)

where A is —$CH_2$—, can be made by, e.g., reacting Compound D or F, the latter after deprotecting the amine group, with a halogenated alkyne compound to form Compound Z, as illustrated below in Scheme 4:

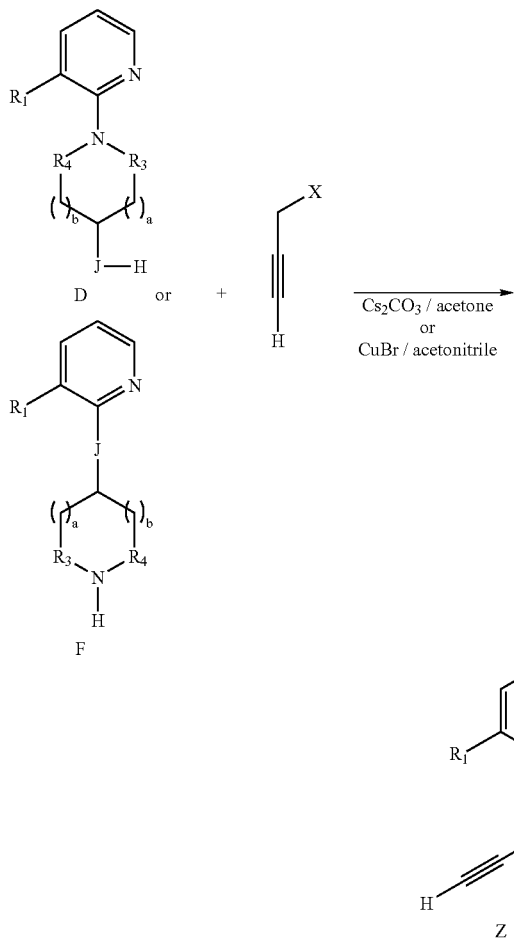

Scheme 4 where X is Cl, Br or I, J is N(H) or O, and $R_1$, $R_3$, $R_4$, a and b are defined above for the compounds of Formula (I), and then further reacting Compound Z, e.g., as described in Scheme 1. A representative procedure for coupling a halogenated alkyne with an amine is provided in H-R Tsou et al., *J. Med. Chem.* 2719-2734 (2001) and R. Geri et al., *Gazz. Chim. Ital.* 241-248 (1994). A representative procedure for coupling a halogenated alkyne with a hydroxyl is provided in R. S. Liu et al., *Tetrahedron* 58:5627-5637 (2002).

The 2-halopyridine compounds and the diamines and hydroxylamines of formulas C and E are commercially available or can be made using methods known to those skilled in the art. For example, compounds of formulas C and E wherein $R_3$ and/or $R_4$ are —$CH(CH_3)$— can be prepared in a manner analogous to that described in F. P. J. T. Rutjes et al., *J. Org. Chem.* 67:7869-7871 (2002); compounds of formula C wherein J is —N(H)— and $R_3$ and/or $R_4$ are —C(O)— can be prepared in a manner analogous to that described in W. Klaus et al., *J. Org. Chem.* 65:7406-7416 (2000); and compounds of formula C wherein J is —O— and $R_3$ and/or $R_4$ are —C(O)— can be prepared in a manner analogous to that described in F. P. J. T. Rutjes et al., *J. Org. Chem.* 67:7869-7871 (2002).

Certain Pyridine-alkynyl Compounds can have asymmetric centers and therefore exist in different enantiomeric and diastereomeric forms. A Pyridine-alkynyl Compound can be in the form of an optical isomer or a diastereomer. Accordingly, the invention encompasses Pyridine-alkynyl Compounds and their uses as described herein in the form of their optical isomers, diasteriomers and mixtures thereof, including a racemic mixture. Optical isomers of the Pyridine-alkynyl Compounds can be obtained by well known techniques such as chiral chromatography or formation of diastereomeric salts from an optically active acid or base.

In addition, one or more hydrogen, carbon or other atoms of a Pyridine-alkynyl Compound can be replaced by an isotope of the hydrogen, carbon or other atoms. Such compounds, which are encompassed by the present invention, are useful as research and diagnostic tools in metabolism pharmacokinetic studies and in binding assays.

4.3 Therapeutic Uses of the Pyridine-Alkynyl Compounds

In accordance with the invention, the Pyridine-alkynyl Compounds are administered to an animal in need of treatment or prevention of a Condition.

In one embodiment, an effective amount of a Pyridine-alkynyl Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Pyridine-alkynyl Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, a seizure, stroke, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Pyridine-alkynyl Compounds can be used to treat or prevent acute or chronic pain. Examples of pain treatable or preventable using the Pyridine-alkynyl Compounds include, but are not limited to, cancer pain, labor pain, myocardial infarction pain, pancreatic pain, colic pain, post-operative pain, headache pain, muscle pain, arthritic pain, neuropathic pain, and pain associated with a periodontal disease, including gingivitis and periodontitis.

The Pyridine-alkynyl Compounds can also be used for treating or preventing pain associated with inflammation or with an inflammatory disease in an animal. Such pain can arise where there is an inflammation of the body tissue which can be a local inflammatory response and/or a systemic inflammation. For example, the Pyridine-alkynyl Compounds can be used to treat or prevent pain associated with inflammatory diseases including, but not limited to: organ transplant rejection; reoxygenation injury resulting from organ transplantation (see Grupp et al., *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Pyridine-alkynyl Compounds can also be used for treating or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

The Pyridine-alkynyl Compounds can be used to treat or prevent UI. Examples of UI treatable or preventable using the Pyridine-alkynyl Compounds include, but are not limited to, urge incontinence, stress incontinence, overflow incontinence, neurogenic incontinence, and total incontinence.

The Pyridine-alkynyl Compounds can be used to treat or prevent an addictive disorder, including but not limited to, an eating disorder, an impulse-control disorder, an alcohol-related disorder, a nicotine-related disorder, an amphetamine-related disorder, a cannabis-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, and Alcohol-Related Disorder not otherwise specified (NOS).

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, and Amphetamine Related Disorder not otherwise specified (NOS).

Cannabis-related disorders include, but are not limited to, Cannabis Dependence, Cannabis Abuse, Cannabis Intoxication, Cannabis Intoxication Delirium, Cannabis-Induced Psychotic Disorder with delusions, Cannabis-Induced Psychotic Disorder with hallucinations, Cannabis-Induced Anxiety Disorder, and Cannabis Related Disorder not otherwise specified (NOS).

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, and Cocaine Related Disorder not otherwise specified (NOS).

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Persisting Perception Disorder (Flashbacks), and Hallucinogen Related Disorder not otherwise specified (NOS).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, and Inhalant Related Disorder not otherwise specified (NOS).

Opioid-related disorders include, but are not limited to, Opioid Dependence, Opioid Abuse, Opioid Intoxication, Opioid Withdrawal, Opioid Intoxication Delirium, Opioid-Induced Psychotic Disorder with delusions, Opioid-Induced Psychotic Disorder with hallucinations, Opioid-Induced Anxiety Disorder, and Opioid Related Disorder not otherwise specified (NOS).

The Pyridine-alkynyl Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Pyridine-alkynyl Compounds can be used to treat or prevent generalized anxiety or severe anxiety and the symptoms associated with anxiety, including but not limited to, restlessness, tension, tachycardia, dyspnea, depression including chronic "neurotic" depression, panic disorder, agoraphobia and other specific phobias, eating disorders, and personality disorders.

The Pyridine-alkynyl Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Pyridine-alkynyl Compounds can be used to treat or prevent a seizure, including but not limited to, infantile spasms, febrile seizures, and epileptic seizures.

The Pyridine-alkynyl Compounds can be used to treat or prevent strokes, including but not limited to, ischemic strokes and hemorrhagic strokes.

The Pyridine-alkynyl Compounds can be used to treat or prevent a pruritic condition, including but not limited to, pruritus caused by dry skin, scabies, dermatitis, herpetiformis, atopic dermatitis, pruritus vulvae et ani, malaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Pyridine-alkynyl Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Pyridine-alkynyl Compounds can be used to treat or prevent a cognitive disorder, including but not limited to, delirium and dementia such as multi-infarct dementia, dementia pugilistica, dementia caused by AIDS, and dementia caused by Alzheimer's disease.

The Pyridine-alkynyl Compounds can be used to treat or prevent a memory deficiency, including but not limited to, dissociative amnesia and dissociative fugue.

The Pyridine-alkynyl Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Pyridine-alkynyl Compounds can be used to treat or prevent Huntington's chorea.

The Pyridine-alkynyl Compounds can be used to treat or prevent ALS.

The Pyridine-alkynyl Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Pyridine-alkynyl Compounds can be used to treat or prevent a muscle spasm.

The Pyridine-alkynyl Compounds can be used to treat or prevent a migraine.

The Pyridine-alkynyl Compounds can be used to treat or prevent vomiting, including but not limited to, nausea vomiting, dry vomiting (retching), and regurgitation.

The Pyridine-alkynyl Compounds can be used to treat or prevent dyskinesia, including but not limited to, tardive dyskinesia and biliary dyskinesia.

The Pyridine-alkynyl Compounds can be used to treat or prevent depression, including but not limited to, major depression and bipolar disorder.

Without wishing to be bound by theory, Applicants believe that the Pyridine-alkynyl Compounds are antagonists for mGluR5.

The invention also relates to methods for inhibiting mGluR5 function in a cell comprising contacting a cell capable of expressing mGluR5 with an amount of a Pyridine-alkynyl Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal, a human in one embodiment, by contacting a cell, in an animal, with an amount of a Pyridine-alkynyl Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are known in the art.

Without wishing to be bound by theory, Applicants believe that the Pyridine-alkynyl Compounds are antagonists for mGluR1.

The invention relates to methods for inhibiting mGluR1 function in a cell comprising contacting a cell capable of expressing mGluR1 with an amount of a Pyridine-alkynyl Compound effective to inhibit mGluR1 function in the cell. This method can be used in vitro, for example, as an assay to select cells that express mGluR1 and, accordingly, are useful as part of an assay to select compounds useful for treating or preventing a Condition. The method is also useful for inhibiting mGluR1 function in a cell in vivo, in an animal, a human in one embodiment, by contacting a cell, in an animal, with an amount of a Pyridine-alkynyl Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are known in the art.

4.3.1 Therapeutic/Prophylactic Administration and Compositions of the Invention Due to their activity, the Pyridine-alkynyl Compounds are advantageously useful in veterinary and human medicine. As described above, the Pyridine-alkynyl Compounds are useful for treating or preventing a Condition in an animal in need thereof.

When administered to an animal, the Pyridine-alkynyl Compounds are administered as a component of a composition that comprises a pharmaceutically acceptable carrier or excipient. The present compositions, which comprise a Pyridine-alkynyl Compound, can be administered orally. The Pyridine-alkynyl Compounds of the invention can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Pyridine-alkynyl Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Pyridine-alkynyl Compounds into the bloodstream.

In specific embodiments, it can be desirable to administer the Pyridine-alkynyl Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Pyridine-alkynyl Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Pyridine-alkynyl Compounds can be formulated as a suppository, with traditional binders and excipients such as triglycerides.

In another embodiment, the Pyridine-alkynyl Compounds can be delivered in a vesicle, in particular a liposome (see Langer, *Science* 249:1527-1533 (1990) and Treat et al., *Liposomes in the Therapy of Infectious Disease and Cancer* 317-327 and 353-365 (1989).

In yet another embodiment, the Pyridine-alkynyl Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Pyridine-alkynyl Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water and, in one embodiment, saline are particularly useful excipients when the Pyridine-alkynyl Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsions, tablets, pills, pellets, capsules, capsules containing liquids, powders, sustained-release formulations, suppositories, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Pyridine-alkynyl Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Pyridine-alkynyl Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Pyridine-alkynyl Compounds are to be administered by infusion, they can be dispensed, for example, with an infusion bottle containing sterile pharmaceutical grade water or saline. Where the Pyridine-alkynyl Compounds are administered by injection, an ampule of sterile water for injection or saline can be provided so that the ingredients can be mixed prior to administration.

The Pyridine-alkynyl Compounds can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a Pyridine-alkynyl Compound to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Pyridine-alkynyl Compound, and can thus reduce the occurrence of adverse side effects.

Controlled- or sustained-release compositions can initially release an amount of a Pyridine-alkynyl Compound that promptly produces the desired therapeutic or prophylactic effect, and gradually and continually release other amounts of the Pyridine-alkynyl Compound to maintain this level of therapeutic or prophylactic effect over an extended period of time. To maintain a constant level of the Pyridine-alkynyl Compound in the body, the Pyridine-alkynyl Compound can be released from the dosage form at a rate that will replace the amount of Pyridine-alkynyl Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Pyridine-alkynyl Compound that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances in view of published clinical studies. Suitable effective dosage amounts, however, range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a Pyridine-alkynyl Compound, in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Pyridine-alkynyl Compound is administered, the effective dosage amounts correspond to the total amount administered.

Where a cell capable of expressing mGluR5 or mGluR1 is contacted with a Pyridine-alkynyl Compound in vitro, the amount effective for inhibiting the mGluR5 or mGluR1 receptor function in a cell will typically range from about 0.01 μg/L to about 5 mg/L, in one embodiment, from about 0.01 μg/L to about 2.5 mg/L, in another embodiment, from about 0.01 μg/L to about 0.5 mg/L, and in another embodiment, from about 0.01 μg/L to about 0.25 mg/L of a solution or suspension of a pharmaceutically acceptable carrier or excipient. In one embodiment, the volume of solution or suspension comprising the Pyridine-alkynyl Compound is from about 0.01 μL to about 1 mL. In another embodiment, the volume of solution or suspension is about 200 μL.

Where a cell capable of expressing VR1, mGluR5, or mGluR1 is contacted with a Pyridine-alkynyl Compound in vivo, the amount effective for inhibiting the receptor function in a cell will typically range from about 0.01 mg/kg of body weight to about 2500 mg/kg of body weight, although it typically ranges from about 100 mg/kg of body weight or less. In one embodiment, the effective dosage amount ranges from about 0.01 mg/kg of body weight to about 100 mg/kg of body weight of a Pyridine-alkynyl Compound, in another embodiment, about 0.020 mg/kg of body weight to about 50 mg/kg of body weight, and in another embodiment, about 0.025 mg/kg of body weight to about 20 mg/kg of body weight. In one embodiment, an effective dosage amount is administered about every 24 h. In another embodiment, an effective dosage amount is administered about every 12. In another embodiment, an effective dosage amount is administered about every 8. In another embodiment, an effective dosage amount is administered about every 6 h. In another embodiment, an effective dosage amount is administered about every 4 h.

The Pyridine-alkynyl Compounds can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering another therapeutic agent to the animal being administered a Pyridine-alkynyl Compound. In one embodiment, the other therapeutic agent is administered in an effective amount.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the Pyridine-alkynyl Compound is less than its effective amount would be where the other therapeutic agent is not administered. In this case, without being bound by theory, it is believed that the Pyridine-alkynyl Compounds and the other therapeutic agent act synergistically to treat or prevent a Condition.

The other therapeutic agent can be, but is not limited to, an opioid agonist, a non-opioid analgesic, a non-steroidal anti-inflammatory agent, an antimigraine agent, a Cox-1 inhibitor, an antiemetic, a β-adrenergic blocker, an anticonvulsant, an antidepressant, a Ca2+-channel blocker, an anticancer agent, an agent for treating or preventing UI, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazine; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's *The Pharmacological Basis of Therapeutics* 617-57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy* Vol II 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocomine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can alternatively be an agent useful for reducing any potential side effects of a Pyridine-alkynyl Compounds. For example, the other therapeutic agent can be an antiemetic agent. Examples of useful antiemetic agents include, but are not limited to, metoclopromide, domperidone, prochlorperazine, promethazine, chlorpromazine, trimethobenzamide, odansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimelidine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfuilvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene;

parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ-vinyl GABA, acetazolamide, and felbamate.

Examples of useful therapeutic agents for treating or preventing a seizure include, but are not limited to, carbamazepine, ethosuximide, gabapentin, lamotrigine, phenobarbital, phenyloin, primidone, valproic acid, trimethadione, benzodiazepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Pyridine-alkynyl Compound and the other therapeutic agent can act additively or, in one embodiment, synergistically. In one embodiment, a Pyridine-alkynyl Compound is administered concurrently with another therapeutic agent; for example, a composition comprising an effective amount of a Pyridine-alkynyl Compound, an effective amount of another therapeutic agent can be administered. Alternatively, a composition comprising an effective amount of a Pyridine-alkynyl Compound and a different composition comprising an effective amount of another therapeutic agent can be concurrently administered. In another embodiment, an effective amount of a Pyridine-alkynyl Compound is administered prior or subsequent to administration of an effective amount of another therapeutic agent. In this embodiment, the Pyridine-alkynyl Compound is administered while the other therapeutic agent exerts its therapeutic effect, or the other therapeutic agent is administered while the Pyridine-alkynyl Compound exerts its therapeutic effect for treating or preventing a Condition.

A composition of the invention is prepared by a method comprising admixing a Pyridine-alkynyl Compound or a pharmaceutically acceptable salt and a pharmaceutically acceptable carrier or excipient. Admixing can be accomplished using methods known for admixing a compound (or salt) and a pharmaceutically acceptable carrier or excipient. In one embodiment the composition is prepared such that the Pyridine-alkynyl Compound is present in the composition in an effective amount.

4.3.2 Kits

The invention encompasses kits that can simplify the administration of a Pyridine-alkynyl Compound to an animal.

A typical kit of the invention comprises a unit dosage form of a Pyridine-alkynyl Compound. In one embodiment, the unit dosage form is a container, which can be sterile, containing an effective amount of a Pyridine-alkynyl Compound and a pharmaceutically acceptable carrier or excipient. The kit can further comprise a label or printed instructions instructing the use of the Pyridine-alkynyl Compound to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a Pyridine-alkynyl Compound, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include but are not limited to a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Examples 1-7 relate to the synthesis of illustrative Pyridine-alkynyl Compounds.

5.1 Example 1

Synthesis of Compound ALJ(Ib)

Compound ALJ(Ib) was prepared according to the following scheme:

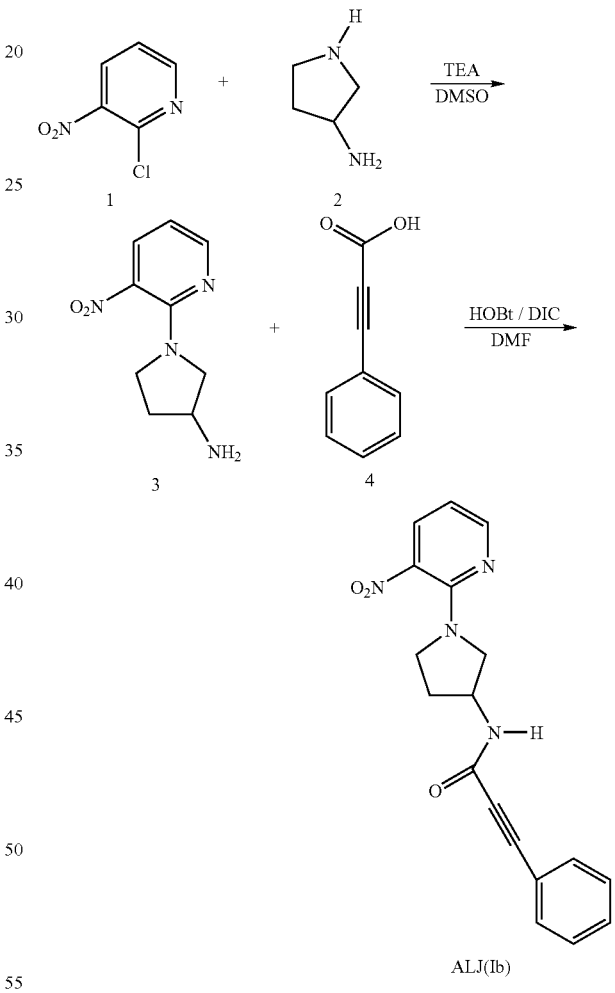

2-Chloro-3-nitro-pyridine (1) (8.8 g, 56.6 mmol) (commercially available from Aldrich Chemical Co., Milwaukee, Wis.) was reacted with 3-amino-pyrrolidine (2) (Aldrich, 4.8 g, 55.7 mmol) in DMSO (50 mL) followed by the addition of TEA (7.7 mL, 55.7 mmol). The reaction was stirred at 100° C. for 15 hours. Brine and ethyl acetate ("EtOAc") were added to the reaction and the aqueous and organic phases were separated. The aqueous phase was extracted twice with EtOAc. The combined organic extract was washed with brine, dried with sodium sulfate, and the solvent removed under reduced pressure to provide a residue that was purified by column chromatography on a silica column (normal phase silica gel, 35-60 μm particle size (230-400 mesh)) using a gradient of 50% EtOAc/hexane to 100% EtOAc to provide 10.6 g (91% yield) of compound (3).

Compound (3) (318 mg, 1.5 mmol) was treated with phenylpropiolic acid (4) (Aldrich, 186 mg, 1.28 mmol) in DMF (2 mL) at about 25° C. followed by the addition of HOBt (459 mg, 3.0 mmol) and DIC 378 mg, 3.0 mmol), also at about 25° C. The reaction mixture was then purified by column chromatography on a silica column (normal phase silica gel, 35-60 μm particle size (230-400 mesh)) using a gradient of 50% EtOAc/hexane to 100% EtOAc to provide 350 mg (81% yield) of purified compound ALJ(Ib).

The structure of Compound ALJ(Ib) was confirmed by $^1$H NMR analysis. Compound ALJ(Ib): $^1$H NMR (400 MHz, CD$_3$OD) δ 2.12 (m, 1H), 2.25 (m, 1H), 3.18 (bm, 2H), 3.61 (m, 2H), 4.41 (s, 1H), 6.62 (bm, 2H), 7.21 (q, 2H), 7.32 (t, 1H), 7.41 (t, 2H), 8.11 (d, 1H), 8.32 (s, 1H).

5.2 Example 2

Synthesis of Compound ABR(Ib)

Compound ABR(Ib) was prepared according to the following scheme:

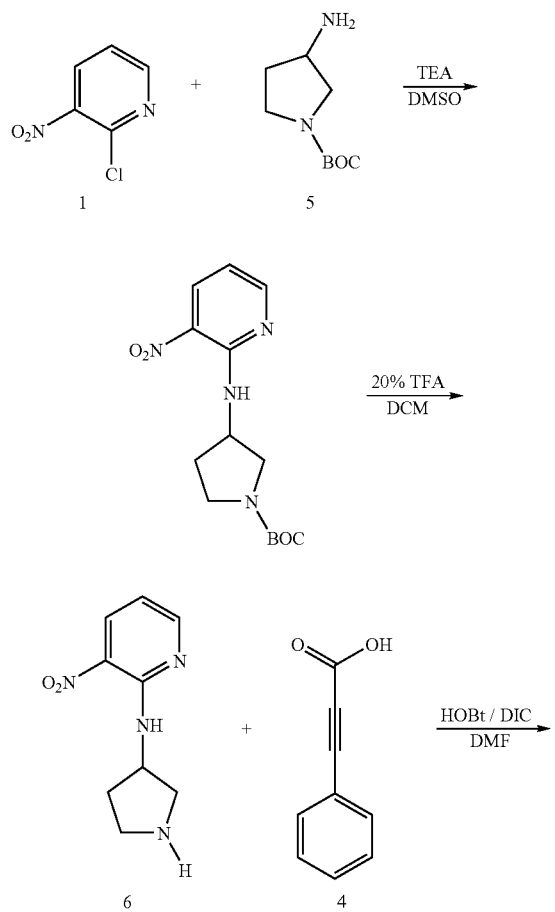

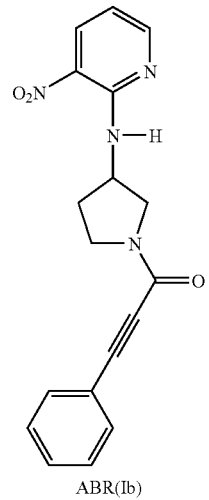

ABR(Ib)

2-Chloro-3-nitro-pyridine (1) (4.3 g, 27.6 mmol) was reacted with (+/−)-3-amino-1-N-BOC-pyrrolidine (5) (5.0 g, 26.8 mmol) in DMSO (50 mL) followed by the addition of TEA (3.5 mL, 26.8 mmol). The reaction was stirred at 100° C. for 15 hours. Brine and EtOAc were added to the reaction and the aqueous and organic phases were separated. The aqueous phase was extracted twice with EtOAc. The combined organic extract was washed with brine, dried with sodium sulfate, and concentrated. The t-butoxycarbonyl ("BOC") protecting group was removed using 20% TFA in DCM to obtain compound (6). The reaction mixture was then purified by column chromatography on a silica column (normal phase silica gel, 35-60 μm particle size (230-400 mesh)) using a gradient of 50% EtOAc/hexane to 100% EtOAc to provide 4.3 g (79% yield) of purified compound (6).

Compound (6) (370 mg) was treated with phenylpropiolic acid (4) (631 mg, 3.03 mmol) in DMF (10 mL) at about 25° C. followed by the addition of HOBt (818 mg, 6.06 mmol) and DIC (886 mg, 6.06 mmol), each also at about 25° C. The reaction mixture was purified by column chromatography on a silica column (normal phase silica gel, 35-60 μm particle size (230-400 mesh)) using a gradient of 50% EtOAc/hexane to 100% EtOAc to provide 635 mg (75% yield) of purified Compound ABR(Ib).

The structure of Compound ABR(Ib) was confirmed by $^1$H NMR analysis. Compound ABR(Ib): $^1$H NMR (400 MHz, CD$_3$OD) δ 2.11 (bm, 1H), 2.51 (m, 1H), 3.52-4.21 (bm, 4H), 5.10 (m, 1H), 6.61 (t, 1H), 7.31 (m, 3H), 7.51 (m, 2H), 8.22 (s, 1H), 8.52 (t, 2H).

5.3 Example 3

Synthesis of Compound AEC(Ib)

Compound AEC(Ib) was prepared according to the following scheme:

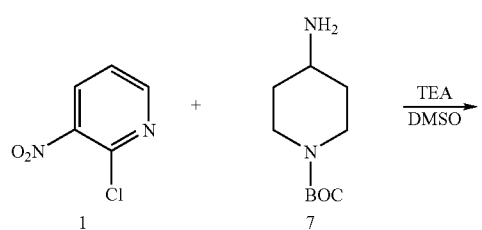

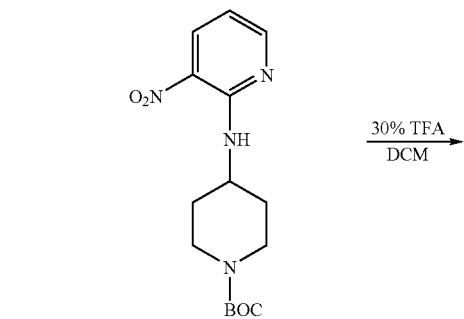

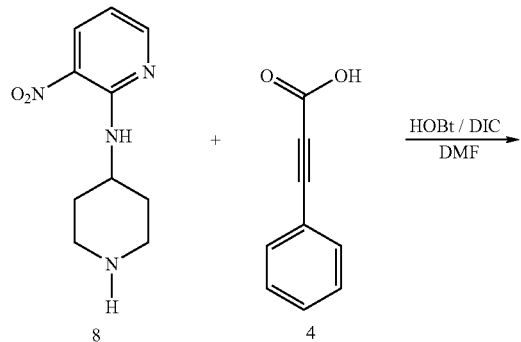

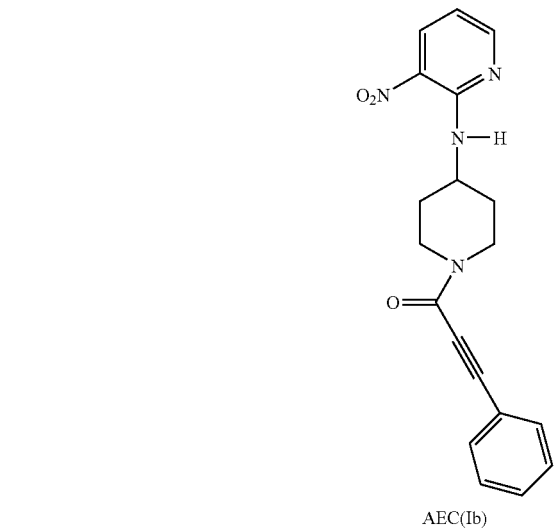

2-Chloro-3-nitro-pyridine (1) (0.5 g, 3.2 mmol), 4-amino-1-BOC-piperidine (7) (0.5 g, 3.2 mmol, prepared from 4-amino-1-piperidine (Aldrich)) and TEA (0.6 mL, 4.17 mmol) in DMSO (40 mL) was stirred at 100° C. for 15 hours. The reaction mixture was concentrated under reduced pressure and the resulting product was deprotected with 30% TFA in DCM. The resulting crude residue was purified by column chromatography on a silica column (normal phase silica gel, 35-60 µm particle size (230-400 mesh)) using an eluent gradient of 20:80 methyl alcohol ("MeOH"):EtOAc to 50:50 MeOH:EtOAc to provide 0.55 g (yield 89%) of purified compound (8).

Compound (8) (200 mg) was treated with phenylpropiolic acid (4) (132 mg, 0.899 mmol) in DMF (5 mL) followed by the addition of HOBt (275 mg, 1.7 mmol) and DIC (214 mg, 1.7 mmol) to provide Compound AEC(Ib) as a yellow solid. Purification of the yellow solid by column chromatography on a silica column (normal phase silica gel, 35-60 µm particle size (230-400 mesh)) using a gradient of 50% EtOAc/hexane to 100% EtOAc provided 220 mg (81% yield) of purified Compound AEC(Ib).

The structure of Compound AEC(Ib) was confirmed by $^1$H NMR and mass spectrometry analysis. Compound AEC(Ib): $^1$H NMR (400 MHz, CD$_3$OD): δ 1.65 (bm, 2H), 2.25 (t, 2H), 3.18 (t, 1H), 3.55 (t, 1H), 4.51 (bm, 3H), 6.75 (s, 1H), 7.44 (q, 3H), 7.32 (t, 1H), 7.62 (t, 2H), 8.11 (bs, 1H), 8.32 (bs, 1H); MS (ED): m/z 351 (M+).

5.4 Example 4

Synthesis of Compound AAB(Ib)

Compound AAB(Ib) was prepared according to the following scheme:

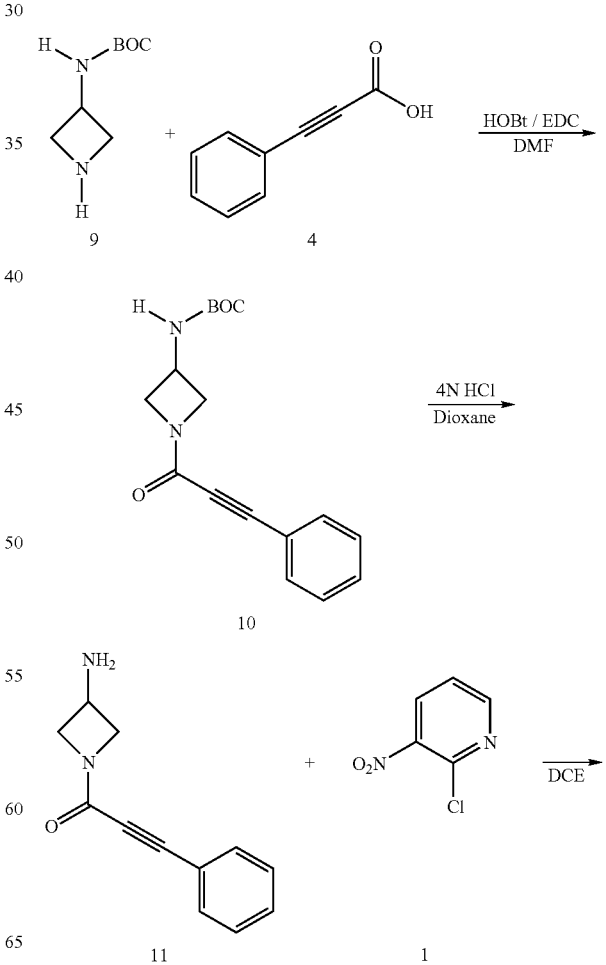

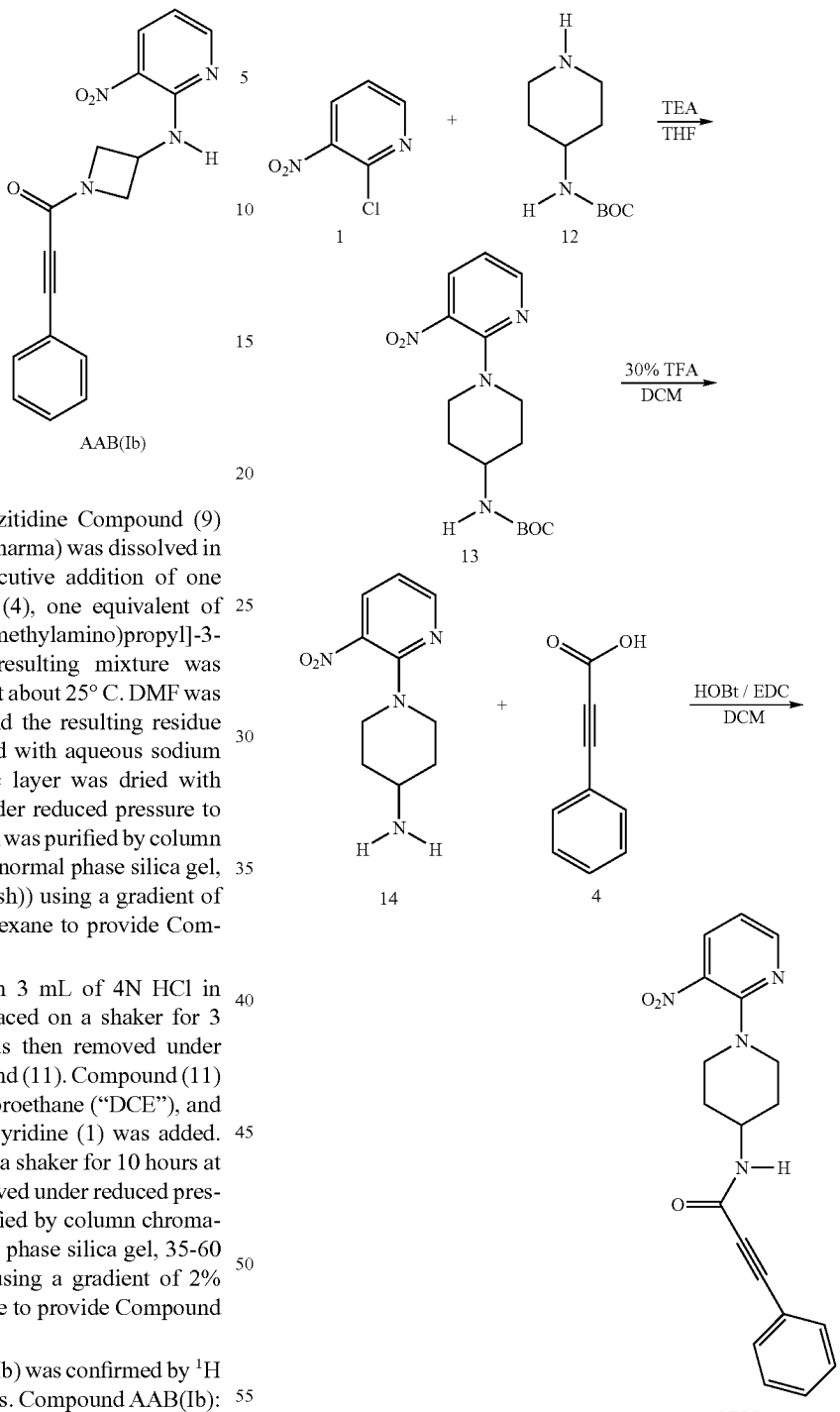

One equivalent of the blocked azitidine Compound (9) (commercially available from Beta Pharma) was dissolved in 4 mL of DMF followed by consecutive addition of one equivalent of phenylpropiolic acid (4), one equivalent of HOBt and one equivalent of 1-[3-(dimethylamino)propyl]-3-ethylcarbodiimide ("EDC"). The resulting mixture was placed on a shaker for about 3 hours at about 25° C. DMF was removed under reduced pressure and the resulting residue was dissolved in EtOAc and washed with aqueous sodium bicarbonate and brine. The organic layer was dried with sodium sulfate and concentrated under reduced pressure to provide crude Compound (10), which was purified by column chromatography on a silica column (normal phase silica gel, 35-60 μm particle size (230-400 mesh)) using a gradient of 2% EtOAc/hexane to 75% EtOAc/hexane to provide Compound (10).

Compound (10) was dissolved in 3 mL of 4N HCl in dioxane (Aldrich Chemical) and placed on a shaker for 3 hours at about 25° C. Dioxane was then removed under reduced pressure to provide Compound (11). Compound (11) was then dissolved in 3 mL of dichloroethane ("DCE"), and one equivalent of 2-chloro-3-nitro-pyridine (1) was added. The resulting mixture was placed on a shaker for 10 hours at about 25° C., and the DCE was removed under reduced pressure. The resulting residue was purified by column chromatography on a silica column (normal phase silica gel, 35-60 μm particle size (230-400 mesh)) using a gradient of 2% EtOAc/hexane to 75% EtOAc/hexane to provide Compound AAB(Ib) as a yellow solid.

The structure of Compound AAB(Ib) was confirmed by $^1$H NMR and mass spectrometry analysis. Compound AAB(Ib): $^1$H NMR (400 MHz, CDCl$_3$): d 8.54-8.39 (m, 3H), 7.61-7.53 (m, 2H), 7.49-7.35 (m, 3H), 6.86-6.78 (m, 1H), 5.08-4.96 (m, 1H), 4.80-4.72 (m, 1H), 4.64-4.50 (m, 1H), 4.31-4.21 (m, 1H), 4.13-4.04 (m, 1H); MS (EI): m/z 345 (M++Na).

5.5 Example 5

Synthesis of Compound ANU(Ib)

Compound ANU(Ib) was prepared according to the following scheme:

2-Chloro-3-nitro-pyridine (1) (2.92 g, 18.5 mmol) was dissolved in 70 mL of tetrahydrofuran ("THF"). 4-BOC-amino-piperidine (12) (3.70 g, 18.5 mmol) and TEA (20 mL) were added and the reaction mixture was stirred at about 25° C. for 8 hours. The reaction mixture was diluted with 300 mL of EtOAc and washed with an aqueous saturated solution of sodium bicarbonate, the organic layer was dried with sodium sulfate and concentrated to provide 5.48 g of BOC-protected Compound (13). Compound (13) was dissolved in 80 mL of 30% TFA in DCM and stirred at about 25° C. for 10 hours. The mixture was then diluted with 350 mL of EtOAc and washed with brine. The organic layer was dried with sodium sulfate and concentrated to provide 2.22 g of Compound (14). Compound (14) (200 mg, 0.9 mmol) was dissolved in DCM (3 mL) followed by consecutive addition of phenylpropiolic acid (4) (131 mg, 0.9 mmol), HOBt (122 mg, 0.9 mmol) and EDC (173 mg, 0.9 mmol). The mixture was stirred at about 25° C. for 2 hours and purified by column chromatography on a silica column (normal phase silica gel, 35-60 μm particle size (230-400 mesh)) using a gradient of 2% EtOAc/hexane to 75% EtOAc/hexane to provide 90 mg of Compound ANU (Ib) as a yellow solid.

The structure of Compound ANU(Ib) was confirmed by $^1$H NMR analysis. Compound ANU(Ib): $^1$H NMR (400 MHz, CDCl$_3$): δ 8.38-8.32 (m, 1H), 8.19-8.12 (m, 1H), 7.60-7.50 (m, 2H), 7.47-7.32 (m, 3H), 6.81-6.75 (m, 1H), 5.99 (bs, 1H), 4.24-4.07 (m, 1H), 3.90-3.77 (m, 2H), 3.21-3.07 (m, 2H), 2.17-2.07 (m, 2H), 1.74-1.58 (m, 2H).

5.6 Example 6

Synthesis of Compound AJT(Ib)

Compound AJT(Ib) was prepared according to the following scheme:

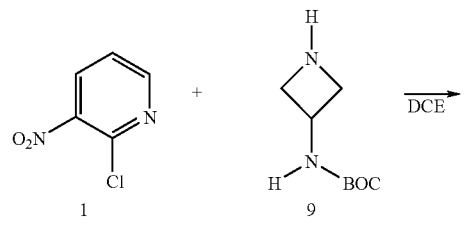

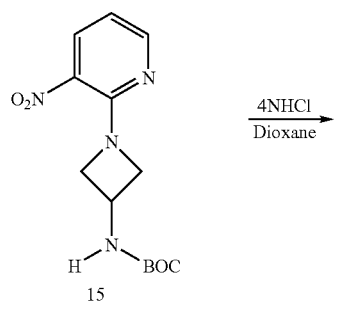

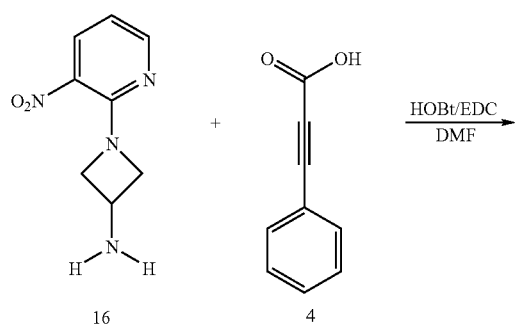

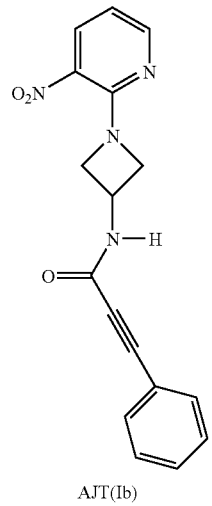

AJT(Ib)

2-Chloro-3-nitro-pyridine (1) (138 mg, 0.87 mmol) was dissolved in 7.0 mL of DCE followed by the addition of the blocked azitidine Compound (9) (150 mg, 0.87 mmol). The reaction mixture was stirred at 50° C. for 4 hours and purified by column chromatography on a silica column (normal phase silica gel, 35-60 μm particle size (230-400 mesh)) using a gradient of 2% EtOAc/hexane to 75% EtOAc/hexane to provide Compound (15). Compound (15) was dissolved in 4 mL of 4N HCl in dioxane at about 25° C. and treated for 3 hours. Dioxane was then removed under reduced pressure to provide Compound (16). Compound (16) was dissolved in 3 mL of DMF followed by consecutive addition of phenylpropiolic acid (4) (127 mg, 0.87 mmol), HOBt (118 mg, 0.87 mmol) and EDC (167 mg, 0.87 mmol). The reaction mixture was stirred at about 25° C. for 2 hours and purified by column chromatography on a silica column (normal phase silica gel, 35-60 μm particle size (230-400 mesh)) using a gradient of 2% EtOAc/hexane to 75% EtOAc/hexane to provide 17 mg of AJT(Ib) as a yellow solid.

The structure of Compound AJT(Ib) was confirmed by $^1$H NMR analysis. Compound AJT(Ib): $^1$H NMR (400 MHz, CDCl$_3$): δ 8.46-8.39 (m, 1H), 8.28-8.21 (m, 1H), 7.62-7.52 (m, 2H), 7.51-7.36 (m, 3H), 6.85-6.75 (m, 1H), 6.49-6.39 (m, 1H), 4.96-4.83 (m, 1H), 4.59-4.48 (m, 2H), 4.17-4.07 (m, 2H).

5.7 Example 7

Synthesis of Compound BET(Ib)

Compound BET(Ib) was prepared from Compound (1) according to Example 1 except that 3-hydroxy-pyrrolidine (Aldrich) was used in place of Compound (2).

The structure of Compound BET(Ib) was confirmed by $^1$H NMR and mass spectrometry analysis. Compound BET(Ib): $^1$H NMR (400 MHz, CDCl$_3$): δ 2.25-2.40 (m, 2H), 3.40-3.55 (m, 2H), 3.85-4.00 (m, 2H), 5.60 (s, 1H), 6.75-6.80 (m, 1H), 7.35-7.45 (m, 2H), 7.45-7.55 (m, 1H), 7.62 (d, 2H), 8.15 (d, 1H), 8.40 (d, 1H); MS (EI): m/z 360 (M++Na).

5.8 Example 8

Binding of an Illustrative Pyridine-Alkynyl Compound to mGluR5

The following assay can be used to demonstrate that a Pyridine-alkynyl Compound binds to mGluR5.

Cell cultures: Primary glial cultures are prepared from cortices of Sprague-Dawley 18 days old embryos. The cortices are dissected and then dissociated by trituration. The resulting cell homogenate is plated onto poly-D-lysine pre-coated T175 flasks (BIOCOAT, commercially available from Becton Dickinson and Company Inc. of Franklin Lakes, N.J.) in Dulbecco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% $CO_2$. After 24 hours, FCS supplementation is reduced to 10%. On day six, oligodendrocytes and microglia are removed by strongly tapping the sides of the flasks. One day following this purification step, secondary astrocytes cultures are established by subplating onto 96 poly-D-lysine precoated T175 flasks (BIOCOAT) at a density of 65,000 cells/well in DMEM and 10% FCS. After 24 hours, the astrocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% $CO_2$. The procedure allows the expression of the mGluR5 receptor by astrocytes, as demonstrated by S. Miller et al., *J. Neurosci.* 15(9):6103-6109 (1995).

Assay Protocol: After 3-5 days incubation with EGF, the astrocytes are washed with 127 mM NaCl, 5 mM KCl, 2 mM $MgCl_2$, 700 mM $NaH_2PO_4$, 2 mM $CaCl_2$, 5 mM $NaHCO_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader (FLIPR) (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a baseline, DMSO solutions containing various concentrations of the Pyridine-alkynyl Compounds diluted in Assay Buffer (0.05 mL of 4× dilutions for competition curves) are added to the cell plate and fluorescence is monitored for 2 minutes. 0.05 mL of a 4× glutamate solution (agonist) is then added to each well to provide a final glutamate concentration in each well of 10 mM. Plate fluorescence is then monitored for an additional 60 seconds after agonist addition. The final DMSO concentration in the assay is 1.0%. In each experiment, fluorescence is monitored as a function of time and the data is analyzed using Microsoft Excel and GraphPad Prism. Dose-response curves are fit using a non-linear regression to determine the $IC_{50}$ value. In each experiment, each data point is determined two times.

5.9 Example 9

Binding of an Illustrative Pyridine-Alkynyl Compound to mGluR5

Alternatively, the following assay demonstrates that Compound AAB(Ib), an illustrative Pyridine-alkynyl Compound, binds to mGluR5.

40,000 CHO-rat mGluR5 cells/well were plated into 96 well plate (Costar 3409, Black, clear bottom, 96 well, tissue culture treated) for an overnight incubation in Dulbecco's Modified Eagle's Medium (DMEM, pH 7.4) and supplemented with glutamine, 10% FBS, 1% Pen/Strep, and 500 ug/mL Geneticin. CHO-rat mGluR5 cells were washed and treated with Optimem medium and were incubated for 1-4 hours prior to loading cells. Cell plates were washed with loading buffer (127 mM NaCl, 5 mM KCl, 2 mM $MgCl_2$, 700 µM Na $H_2PO_4$, 2 mM $CaCl_2$, 5 mM $NaHCO_3$, 8 mM Hepes, and 10 mM glucose, pH 7.4) and incubated with 3 µM Fluo 4 (commercially available from Molecular probes Inc. of Eugene, Oreg.) in 0.1 mL of loading buffer. After 90 minutes of dye loading, the cells were washed twice with 0.2 mL loading buffer and resuspended in 0.1 mL loading buffer.

The plates containing the CHO-rat mGluR5 cells were transferred to a FLIPR for the assessment of calcium mobilization flux in the presence of glutamate and in the presence or absence of test compounds. After monitoring fluorescence for 15 seconds to establish a baseline, DMSO solutions containing various concentrations of the test compound diluted in loading buffer (0.05 mL of 4× dilutions for the competition curves) were added to the cell plate and fluorescence was monitored for 2 minutes. 0.05 mL of 4× glutamate solution (agonist) was then added to each well to provide a final glutamate concentration in each well of 10 uM. Plate fluorescence was then monitored for an additional 60 seconds after agonist addition. The final DMSO concentration in the assay was 1.0%. In each experiment, fluorescence was monitored as a function of time and the data analyzed using Microsoft Excel and GraphPad Prism. Dose-response curves were fit using a non-linear regression to determine the $IC_{50}$ value. Compound AAB(Ib) showed an $IC_{50}$ value of 109.7±17.9 nM (mean of 4 experiments). In each experiment, each data point was determined at least two times.

5.10 Example 10

In Vivo Assays for Prevention or Treatment of Pain

Test Animals: Each experiment uses rats weighing between 200-260 g at the start of the experiment. The rats are group-housed and have free access to food and water at all times, except prior to oral administration of a Pyridine-alkynyl Compound when food is removed for 16 hours before dosing. A control group acts as a comparison to rats treated with a Pyridine-alkynyl Compound. The control group is administered the carrier for the Pyridine-alkynyl Compound. The volume of carrier administered to the control group is the same as the volume of carrier and Pyridine-alkynyl Compound administered to the test group.

Acute Pain: To assess the actions of the Pyridine-alkynyl Compounds for the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Pyridine-alkynyl Compound. Data are expressed as tail flick latency(s) and the percentage of the maximal possible effect (% MPE), i.e., 20 seconds, is calculated as follows:

$$\%MPE = \frac{[(\text{post administration latency}) - (\text{pre-administration latency})]}{(20\ s\ \text{pre-administration latency})}$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain: To assess the actions of the Pyridine-alkynyl Compounds for the treatment or prevention of inflammatory pain the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/Kg of either a Pyridine-alkynyl Compound; 30 mg/Kg of a control selected from Celebrex, indomethacin or naproxen; or carrier. Responses to noxious mechanical stimuli are then determined 1, 3, 5, and 24 hours post administration. Percentage reversal of hyperalgesia for each animal is defined as:

$$\%\text{Reversal} = \frac{[(\text{post administration } PWT) - (\text{pre-administration } PWT)]}{[(\text{Baseline } PWT) - (\text{pre-administration } PWT)]} \times 100$$

Neuropathic Pain: To assess the actions of the Pyridine-alkynyl Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and a Vetbond surgical glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for the left rear paw of the animal. Percentage reversal of neuropathic hyperalgesia is defined as:

$$\%\text{Reversal} = \frac{[(\text{post administration } PWT) - (\text{pre-administration } PWT)]}{[(\text{Baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Pyridine-alkynyl Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hind-paw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.11 Example 11

In Vivo Assays for Prevention or Treatment of Anxiety

The elevated plus maze test or the shock-probe burying test can be used to assess the anxiolytic activity of Pyridine-alkynyl Compounds in rats or mice.

The Elevated Plus Maze Test: The elevated plus maze consists of a platform with 4 arms, two open and two closed (50 cm×10 cm×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Antianxiety Agents: A Review," *Neurosci. & Biobehavioral Revs.* 9(2):203-222 (1985).

The Shock-Probe Burying Test: For the shock-probe burying test the testing apparatus consists of a plexiglass box measuring 40 cm×30 cm×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra.

5.12 Example 12

In Vivo Assays for Prevention or Treatment of an Addictive Disorder

The conditioned place preference test or drug self-administration test can be used to assess the ability of Pyridine-alkynyl Compounds to attenuate the rewarding properties of known drugs of abuse.

The Conditioned Place Preference Test: The apparatus for the conditioned place preference test consists of two large compartments (45 cm×45 cm×30 cm) made of wood with a plexiglass front wall. These two large compartments are distinctly different. Doors at the back of each large compartment lead to a smaller box (36 cm×18 cm×20 cm) box made of wood, painted grey, with a ceiling of wire mesh. The two large compartments differ in terms of shading (white vs black), level of illumination (the plexiglass door of the white compartment is covered with aluminum foil except for a window of 7 cm×7 cm), texture (the white compartment has a 3 cm thick floor board (40 cm×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), Pyridine-alkynyl Compound pre-treatment+carrier, carrier pre-treatment+morphine, Pyridine-alkynyl Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Pyridine-alkynyl Compound blocks the acquisition of morphine conditioned place preference (reward), there will be no difference in time spent in each side in rats pre-treated with a Pyridine-alkynyl Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Pyridine-alkynyl Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Pyridine-alkynyl Compounds pre-treatment on drug self-administration. On test day, rats are pre-treated with a Pyridine-alkynyl Compound or excipient and then are allowed to self-administer drug as usual. If the Pyridine-alkynyl Compound blocks the rewarding effects of morphine, rats pre-treated with the Pyridine-alkynyl Compound will show a lower rate of responding compared to their previous rate of responding and compared to excipient pre-treated rats. Data is analyzed as the change in number of drug infusions per testing session (number of infusions during test session−number of infusions during training session). The results would show that Pyridine-alkynyl Compounds are useful for treating or preventing an addictive disorder.

5.13 Example 13

Functional Assay for Characterizing mGluR1 Antagonistic Properties

Functional assays for the characterization of mGluR1 antagonistic properties are well known in the art. For example, the following procedure can be used.

A CHO-rat mGluR1 cell line is generated using cDNA encoding rat mGluR1 receptor (M. Masu and S. Nakanishi, *Nature* 349:760-765 (1991)). The cDNA encoding rat mGluR1 receptor can be obtained from, e.g., Prof. S. Nakanishi (Kyoto, Japan).

40,000 CHO-rat mGluR1 cells/well are plated into a COS-TAR 3409, black, clear bottom, 96 well, tissue culture treated plate (commercially available from Fisher Scientific of Chicago, Ill.) and are incubated in Dulbecco's Modified Eagle's Medium (DMEM, pH 7.4) supplemented with glutamine, 10% FBS, 1% Pen/Strep, and 500 μg/mL Geneticin for about 12 h. The CHO-rat mGluR1 cells are then washed and treated with OPTIMEM medium (commercially available from Invitrogen, Carlsbad, Calif.) and incubated for a time period ranging from 1 to 4 hours prior to loading the cells with the dye FLUO-4 (commercially available from Molecular Probes Inc., Eugene, Oreg.). After incubation, the cell plates are washed with loading buffer (127 mM NaCl, 5 mM KCl, 2 mM MgCl$_2$, 700 μM, NaH$_2$PO$_4$, 2 mM CaCl$_2$, 5 mM NaHCO$_3$, 8 mM HEPES, and 10 mM glucose, pH 7.4) and incubated with 3 μM FLUO-4 in 0.1 mL loading buffer for 90 min. The cells are then washed twice with 0.2 mL loading buffer, resuspended in 0.1 mL of loading buffer, and transferred to a FLIPR for measurement of calcium mobilization flux in the presence of glutamate and in the presence or absence of a Pyridine-alkynyl Compound.

To measure calcium mobilization flux, fluoresence is monitored for about 15 s to establish a baseline and DMSO solutions containing various concentrations of a Pyridine-alkynyl Compound ranging from about 50 μM to about 0.8 nM diluted in loading buffer (0.05 mL of a 4× dilution) are added to the cell plate and fluoresence is monitored for about 2 min. 0.05 mL of a 4× glutamate solution (agonist) is then added to each well to provide a final glutamate concentration in each well of 10 μM and fluoresence is monitored for about one additional min. The final DMSO concentration in the assay is 1%. In each experiment fluoresence is monitored as a function of time and the data is analyzed using a non-linear regression to determine the IC$_{50}$ value. In each experiment each data point is determined twice.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:
1. A compound of formula (I):

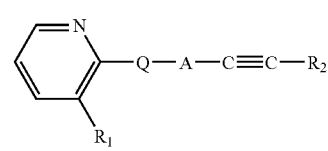

or a pharmaceutically acceptable salt thereof, wherein:
R$_1$ is -halo, —CH$_3$, —CF$_3$, —NO$_2$, —CN or —H;
Q is:

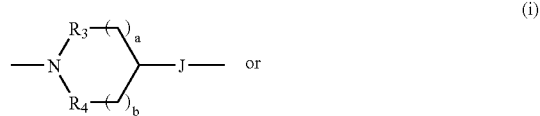

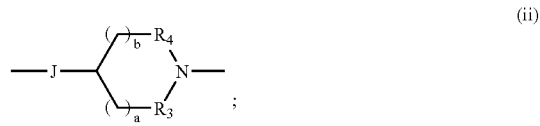

R$_3$ and R$_4$ are independently —CH$_2$—, —CH(CH$_3$)— or —C(O)—;
J is —N(H)— or —O—;
A is —C(O)— or —CH$_2$—;
R$_2$ is —(C$_1$-C$_6$)alkyl, —(C$_3$-C$_8$)cycloalkyl, -phenyl, -naphthyl, or —(C$_{14}$)aryl, each of which is unsubstituted or substituted with one or more R$_5$ groups;

$R_5$ is -halo, —$(C_1-C_6)$alkyl, —$(C_1-C_6)$alkoxy or —OC(halo)$_3$;

a is 0 and b is 1;

each halo is independently —F, —Cl, —Br or —I; and wherein the compound is optionally an optical isomer, a mixture of optical isomers, or a racemic mixture.

2. The compound of claim 1, wherein A is —C(O)—.

3. The compound of claim 1, wherein $R_1$ is —NO$_2$.

4. The compound of claim 2, wherein $R_1$ is —NO$_2$.

5. The compound of claim 4, wherein $R_2$ is -phenyl which is substituted with one or more $R_5$ groups.

6. The compound of claim 5, wherein J is N(H), and $R_3$ and $R_4$ are each —CH$_2$—.

7. The compound of claim 5 present as an optical isomer, wherein at least about 90 mol %, optionally at least about 95 mol %, of the compound is in the (S) form.

8. The compound of claim 5 present as an optical isomer, wherein at least about 90 mol %, optionally at least about 95 mol %, of the compound is in the (R) form.

9. The compound of claim 4, wherein $R_2$ is -phenyl which is unsubstituted.

10. The compound of claim 9, wherein J is N(H), and $R_3$ and $R_4$ are each —CH$_2$—.

11. The compound of claim 9 present as an optical isomer, wherein at least about 90 mol %, optionally at least about 95 mol %, of the compound is in the (S) form.

12. The compound of claim 9 present as an optical isomer, wherein at least about 90 mol %, optionally at least about 95 mol %, of the compound is in the (R) form.

13. The compound of claim 1, wherein at least one of $R_3$ or $R_4$ is —C(O)—.

14. The compound of claim 1, wherein A is —CH$_2$—.

15. The compound of claim 14, wherein $R_1$ is —NO$_2$ and $R_2$ is -phenyl which is unsubstituted or substituted with one or more $R_5$ groups.

16. A compound of formula:

, or or a pharmaceutically acceptable salt thereof.

17. A composition comprising an effective amount of a compound or a pharmaceutically acceptable salt of the compound of claim 1 and a pharmaceutically acceptable carrier or excipient.

18. A composition comprising an effective amount of a compound or a pharmaceutically acceptable salt of the compound of claim 4 and a pharmaceutically acceptable carrier or excipient.

19. A composition comprising an effective amount of a compound or a pharmaceutically acceptable salt of the compound of claim 15 and a pharmaceutically acceptable carrier or excipient.

20. The compound of claim 5, wherein J is O, and $R_3$ and $R_4$ are each —CH$_2$—.

21. The compound of claim 9, wherein J is O, and $R_3$ and $R_4$ are each —CH$_2$—.

22. The compound of claim 2, wherein $R_1$ is —CN.

23. The compound of claim 22, wherein $R_2$ is -phenyl which is substituted with one or more $R_5$ groups.

24. The compound of claim 23, wherein J is N(H), and $R_3$ and $R_4$ are each —CH$_2$—.

25. The compound of claim 22, wherein $R_2$ is -phenyl which is unsubstituted.

26. The compound of claim 25, wherein J is N(H), and $R_3$ and $R_4$ are each —CH$_2$—.

27. The compound of claim 15, wherein J is N(H), and $R_3$ and $R_4$ are each —CH$_2$—.

* * * * *